US011104740B2

(12) United States Patent
Deckert et al.

(10) Patent No.: US 11,104,740 B2
(45) Date of Patent: Aug. 31, 2021

(54) ANTIBODIES AND ASSAYS FOR DETECTION OF CD37

(71) Applicant: DEBIOPHARM INTERNATIONAL, S.A., Lausanne (CH)

(72) Inventors: Jutta Deckert, Lexington, MA (US); Daniel Tavares, Natick, MA (US); Lingyun Rui, Weston, MA (US); Sven Loebrich, Waltham, MA (US); Meghan Puopolo, Burlington, MA (US)

(73) Assignee: DEBIOPHARM INTERNATIONAL, S.A., Lausanne (CH)

(*) Notice: Subject to any disclaimer, the term of this patent is extended or adjusted under 35 U.S.C. 154(b) by 546 days.

(21) Appl. No.: 15/756,345

(22) PCT Filed: Aug. 26, 2016

(86) PCT No.: PCT/US2016/048887
§ 371 (c)(1),
(2) Date: Feb. 28, 2018

(87) PCT Pub. No.: WO2017/040247
PCT Pub. Date: Mar. 9, 2017

(65) Prior Publication Data
US 2018/0244795 A1  Aug. 30, 2018

Related U.S. Application Data

(60) Provisional application No. 62/212,183, filed on Aug. 31, 2015, provisional application No. 62/211,455, filed on Aug. 28, 2015.

(51) Int. Cl.
C07K 16/28 (2006.01)
C07K 16/30 (2006.01)
G01N 33/574 (2006.01)

(52) U.S. Cl.
CPC .......... *C07K 16/2896* (2013.01); *C07K 16/30* (2013.01); *G01N 33/574* (2013.01); *C07K 2317/21* (2013.01); *C07K 2317/24* (2013.01); *C07K 2317/54* (2013.01); *C07K 2317/55* (2013.01); *C07K 2317/56* (2013.01); *C07K 2317/565* (2013.01); *C07K 2317/569* (2013.01); *C07K 2317/622* (2013.01); *C07K 2317/624* (2013.01); *C07K 2317/626* (2013.01); *C07K 2317/92* (2013.01); *G01N 2333/70596* (2013.01)

(58) Field of Classification Search
None
See application file for complete search history.

(56) References Cited

U.S. PATENT DOCUMENTS

| 5,122,368 A | 6/1992 | Greenfield et al. |
|---|---|---|
| 5,595,756 A | 1/1997 | Bally et al. |
| 7,303,749 B1 | 12/2007 | Chari |
| 7,585,491 B2 | 9/2009 | Govindan |
| 7,601,354 B2 | 10/2009 | Chari |
| 7,989,598 B2 | 8/2011 | Steeves et al. |
| 8,088,387 B2 | 1/2012 | Steeves et al. |
| 8,765,917 B2 | 7/2014 | Deckert et al. |
| 9,346,887 B2 | 5/2016 | Deckert et al. |
| 9,447,189 B2 | 9/2016 | Deckert et al. |
| 10,202,460 B2 | 2/2019 | Deckert et al. |
| 10,556,958 B2 | 2/2020 | Deckert et al. |
| 2003/0114398 A1 | 6/2003 | Chatterjee et al. |
| 2004/0166115 A1 | 8/2004 | Griffiths et al. |
| 2005/0136049 A1 | 6/2005 | Ledbetter et al. |
| 2005/0287538 A1 | 12/2005 | Cheung et al. |
| 2006/0039913 A1 | 2/2006 | Das et al. |
| 2006/0233822 A1 | 10/2006 | Xia et al. |
| 2006/0263349 A1 | 11/2006 | McCutcheon et al. |
| 2007/0009519 A1 | 1/2007 | Hariharan et al. |
| 2007/0059306 A1 | 3/2007 | Grosmaire et al. |
| 2007/0237779 A1 | 11/2007 | Ledbetter et al. |
| 2007/0270585 A1 | 11/2007 | Chari et al. |
| 2008/0075726 A1 | 3/2008 | Smith et al. |
| 2008/0226626 A1 | 9/2008 | Hariharan et al. |
| 2008/0227198 A1 | 9/2008 | Hariharan et al. |
| 2008/0279850 A1 | 11/2008 | Brady et al. |
| 2009/0041783 A1 | 2/2009 | Takayama et al. |
| 2009/0136516 A1 | 5/2009 | Tedder et al. |
| 2009/0148447 A1 | 6/2009 | Ledbetter et al. |
| 2009/0175867 A1 | 7/2009 | Thompson et al. |
| 2009/0269336 A1 | 10/2009 | Hong et al. |
| 2009/0274692 A1 | 11/2009 | Tan et al. |
| 2009/0274713 A1 | 11/2009 | Chari et al. |
| 2010/0135900 A1 | 6/2010 | Cerveny et al. |

(Continued)

FOREIGN PATENT DOCUMENTS

| CN | 1446104 A | 10/2003 |
|---|---|---|
| CN | 1494433 A | 5/2004 |

(Continued)

OTHER PUBLICATIONS

Ackler, S., et al., "The Bcl-2 Inhibitor ABT-263 Enhances the Response of Multiple Chemotherapeutic Regimens in Hematologic Tumors in Vivo," Cancer Chemotherapy and Pharmacology 66(5):869-880, Springer Verlag, Germany (2010).

Algate, P., et al., "TRU-016, An Anti-CD37 SMIP (TM) Biologic, in combination with Other therapeutic Drugs in Models of Non-Hodgkin's Lymphoma," Blood 116(21):3931, American Society of Hematology, United States (Nov. 2010), 5 pages.

(Continued)

*Primary Examiner* — Brad Duffy

(74) *Attorney, Agent, or Firm* — Sterne, Kessler, Goldstein & Fox P.L.L.C.

(57) ABSTRACT

The invention generally relates to antibodies that bind to human CD37 and diagnostic assays for CD37-based therapies.

19 Claims, 10 Drawing Sheets

Specification includes a Sequence Listing.

(56) References Cited

U.S. PATENT DOCUMENTS

| | | | |
|---|---|---|---|
| 2010/0189722 | A1 | 7/2010 | Heider et al. |
| 2010/0034820 | A1 | 11/2010 | Ledbetter et al. |
| 2011/0256056 | A1 | 10/2011 | Alper et al. |
| 2011/0256153 | A1 | 10/2011 | Deckert et al. |
| 2012/0020963 | A1 | 1/2012 | Banchereau et al. |
| 2012/0020983 | A9 | 1/2012 | Braun et al. |
| 2012/0276119 | A1 | 11/2012 | Deckert et al. |
| 2013/0058947 | A1 | 3/2013 | Stull et al. |
| 2013/0295104 | A1 | 11/2013 | Deckert et al. |
| 2014/0120083 | A1 | 5/2014 | Stern et al. |
| 2014/0170063 | A1 | 6/2014 | Govindan et al. |
| 2014/0348745 | A1 | 11/2014 | Larsen et al. |
| 2015/0093397 | A1 | 4/2015 | Carrigan |
| 2015/0343077 | A1 | 12/2015 | Deckert et al. |
| 2016/0326258 | A1 | 11/2016 | Deckert et al. |
| 2016/0340438 | A1 | 11/2016 | Deckert et al. |
| 2017/0000900 | A1 | 1/2017 | Romanelli et al. |
| 2019/0183788 | A1 | 6/2019 | Romanelli et al. |
| 2019/0218303 | A1 | 7/2019 | Deckert et al. |
| 2020/0054763 | A1 | 2/2020 | Bertoni et al. |
| 2020/0270361 | A1 | 8/2020 | Deckert et al. |
| 2020/0330604 | A1 | 10/2020 | Li et al. |

FOREIGN PATENT DOCUMENTS

| | | | |
|---|---|---|---|
| CN | 1568198 | A | 1/2005 |
| EP | 0 328 147 | B1 | 5/1994 |
| JP | 2006513203 | A | 4/2006 |
| JP | 2016536298 | A | 11/2016 |
| WO | WO 01/24763 | A2 | 4/2001 |
| WO | WO-0204021 | A1 | 1/2002 |
| WO | WO 2002/060485 | A2 | 8/2002 |
| WO | WO-02060484 | A1 | 8/2002 |
| WO | WO 2002/102972 | A2 | 12/2002 |
| WO | WO-03048306 | A2 | 6/2003 |
| WO | WO 03/083069 | A2 | 10/2003 |
| WO | WO-2004058298 | A1 | 7/2004 |
| WO | WO 2005/017148 | A1 | 2/2005 |
| WO | WO 2005/037989 | A2 | 4/2005 |
| WO | WO 2005/037992 | A2 | 4/2005 |
| WO | WO-2006074397 | A2 | 7/2006 |
| WO | WO 2006/133450 | A2 | 12/2006 |
| WO | WO 2007/014278 | A2 | 2/2007 |
| WO | WO-2007077173 | A1 | 7/2007 |
| WO | WO 2007/146968 | A2 | 12/2007 |
| WO | WO-2007140371 | A2 | 12/2007 |
| WO | WO 2008/052030 | A2 | 5/2008 |
| WO | WO 2008/119567 | A2 | 10/2008 |
| WO | WO 2009/019312 | A2 | 2/2009 |
| WO | WO 2009/065576 | A1 | 5/2009 |
| WO | WO 2009/085576 | A2 | 7/2009 |
| WO | WO 2009/126858 | A2 | 10/2009 |
| WO | WO 2009/126944 | A1 | 10/2009 |
| WO | WO 2009/134977 | A1 | 11/2009 |
| WO | WO 2010/008726 | A1 | 1/2010 |
| WO | WO 2010/009124 | A2 | 1/2010 |
| WO | WO-2010126551 | A1 | 11/2010 |
| WO | WO 2011/090754 | A1 | 7/2011 |
| WO | WO 2011/090762 | A1 | 7/2011 |
| WO | WO 2011/100398 | A1 | 8/2011 |
| WO | WO 2011/100403 | A1 | 8/2011 |
| WO | WO 2011/112978 | A1 | 9/2011 |
| WO | WO 2012/135740 | A2 | 10/2012 |
| WO | WO 2013/149171 | A2 | 10/2013 |
| WO | WO-2013171289 | A1 | 11/2013 |
| WO | WO 2014/143807 | A2 | 9/2014 |
| WO | WO-2014195460 | A1 | 12/2014 |
| WO | WO 2015/038777 | A1 | 3/2015 |
| WO | WO-2015067586 | A2 | 5/2015 |
| WO | WO 2015/116729 | A1 | 8/2015 |
| WO | WO-2015175533 | A2 | 11/2015 |
| WO | WO 2016/200676 | A1 | 12/2016 |
| WO | WO 2017/040247 | A1 | 3/2017 |
| WO | WO-2018083633 | A1 | 5/2018 |
| WO | WO-2019229677 | A1 | 12/2019 |

OTHER PUBLICATIONS

Alley, S.C., et al., "Antibody-drug Conjugates: Targeted Drug Delivery for Cancer," Current Opinion in Chemical Biology 14(4):529-537, Elsevier, England (2010).

Awan, F., et al., "Phase 1 Study of TRU-016, an Anti-CD37 SMIP Protein in Naive and Relapsed and/or Refractory CLL Patients," ASH Annual Meeting 642: Abstract#1792 poster, p. 1, United States (Nov. 2011). Accessed at: https://ash.confex.com/ash/2011/webprogram/Paper39421.html on Jul. 20, 2015.

Wang, L., et al., "Structural Characterization of the Maytansinoid-Monoclonal Antibody Immunoconjugate, huN901-DM1, by mass spectrometry," Protein Science, 14(9):2436-2446, Cold Spring Harbor Laboratory Press, United States (Sep. 2005).

Tutt, A., et al., "Trispecific F(ab')$_3$ Derivatives that use Cooperative Signaling via the TCR/CD3 Complex and CD2 to Activate and Redirect Resting Cytotoxic T Cells," The Journal of Immunology 147:60-69, The American Association of Immunologists, United States (Jul. 1991).

Chen, R., et al., "A Phase II Study of Vorinostat and Rituximab for Treatment of Newly Diagnosed and Relapsed/refractory Indolent Non-hodgkin Lymphoma," Haematologica 100(3):357-362, Ferrata Storti Foundation, Italy (Mar. 2015).

Colman, P.M., "Effects of Amino Acid Sequence Changes on Antibody-antigen Interactions," Research in Immunology 145(1):33-36, Elsevier, France (Jan. 1994).

Deckert, J., et al, "IMGN529, a Novel Antibody-Drug Conjugate (ADC) Targeting CD37 Shows Synergistic Activity with Rituximab in Non-Hodgkin Lymphoma (NHL) Models," poster# 1548. 1 page, 57th ASH Annual Meeting and Exposition, Dec. 6-9, 2014, San Francisco, United States.

Deckert, J., et al.,"Preclinical Mechanistic Studies Investigating Neutrophil and Lymphoid Cell Depletion by IMGN529, a CD37-Targeting Antibody-Drug Conjugate (ADC)," poster# 3119, 2pages, 57th ASH Annual Meeting and Exposition, Dec. 6-9, 2014, San Francisco, United States.

Deckert, J., et al., "IMGN529, a Novel Antibody-Drug Conjugate (ADC) Targeting CD37 Shows Synergistic Activity with Rituximab in Non-Hodgkin Lymphoma (NHL) Models," Blood 126(23):1548, 4 pages American Society of Hematology, United States (Dec. 2015).

Deckert, J., et al., "Preclinical Mechanistic Studies Investigating Neutrophil and Lymphoid Cell Depletion by IMGN529, a CD37-Targeting Antibody-Drug Conjugate (ADC)," 56th ASH Annual Meeting and Exposition: Abstract# 3119, 2 pages, United States (Dec. 2014) Accessed at https://ash.confex.com/ash/2014/webprogram/Paper70777.html on Aug. 26, 2015.

Deckert, J., et al., "Preclinical Mechanistic Studies Investigating Neutrophil and Lymphoid Cell Depletion by IMGN529, a CD37-Targeting Antibody-Drug Conjugate (ADC)," 56th ASH Annual Meeting and Exposition: Poster #3119, 1 page, Abstract# 3119, Accessed at http://www.immunogen.com/documents/Publications/IMGN529%20preclinical%20ASH%2012-2014.pdf on Aug. 26, 2015.

Ducry, L., et al., "Antibody-Drug Conjugates: Linking Cytotoxic Payloads to Monoclonal Antibodies," Bioconjugate Chem. 21:5-13, American Chemical Society, United States (2009).

Epstein, A.L., et al., "Two New Monoclonal Antibodies, Lym-1 and Lym-2, Reactive With Human B-lymphocytes and Derived Tumors, With Immunodiagnostic and Immunotherapeutic Potential," Cancer Research 47(3):830-840, American Association for Cancer Research, United States (Feb. 1987).

Epstein, A.L., et al., "Two New Monoclonal Antibodies (LN-1, LN-2) Reactive in B5 Formalin-fixed, Paraffin-embedded Tissues with Follicular Center and Mantle Zone Human B Lymphocytes and Derived Tumors," Journal of Immunology 133(2):1028-1036, American Association of Immunologists, United States (1984).

Eugenio, G., et al., Identification of anti-lymphoma biomarkers of response to the anti-CD37 antibody drug conjugate (ADC) IMGN529, presented at 58th Annual Meeting and Exposition of the American Society of Hematology 128, 1 page (Dec. 2016).

Zenz, T., et al., "Exceptional in Vitro Activity of CD37 Antibodies in CLL," Blood 116(21): 1021-1022, 2010 ASH Annual Meeting

(56) References Cited

OTHER PUBLICATIONS

Abstracts (Abstract 2460), American Society of Hematology, United States (2010), accessed at https://ashconfex.com/ash/2010/webprogram/Paper2940I.html, accessed on Apr. 4, 2016.

Gershoni, J.M., et al., "Epitope Mapping: the First Step in Developing Epitope-based Vaccines," BioDrugs 21(3):145-156, Springer International, New Zealand (2007).

Gopal, A., et al., "Phase 1b Study of otlertuzumab (TRU-016), an Anti-CD37 monospecific ADAPTIR™ therapeutic protein, in Combination with Rituximab and Bendamustine in Relapsed Indolent Lymphoma patients," Investigational New Drugs Presented at ASH annual meeting 2012, 13 pages.

Gross, J., "Evaluation of Otlertuzumab (TRU-016), an Anti-CD37 ADAPTIR™ Therapeutic in Preclinical Combination Studies with Kinase Inhibitors and a Next Generation Anti-CD20 Mab in Vitro and in Animal Models of Non-Hodgkin's Lymphoma," Blood 124(21):3333, 2 pages, American Society of Hematology, United States (2014).

Hicks, S.W., et al., "The Antitumor Activity of IMGN529, a CD37-targeting Antibody-drug Conjugate, Is Potentiated by Rituximab in Non-Hodgkin Lymphoma Models," Neoplasia 19(9):661-671, Neoplasia Press, United States (Sep. 2017).

Konig, A., et al., "Basic Fibroblast Growth Factor (bFGF) Upregulates the Expression of bcl-2 in B Cell Chronic Lymphocytic Leukemia Cell Lines Resulting in Delaying Apoptosis," Leukemia 11(2):258-265, Nature Publishing Group, England (1997).

Lai, K.C., et al., "The CD37-targeting ADC IMGN529 Combines the Potent Anti-cancer Activity of K7153A Antibody with Efficient Maytansinoid Delivery," AACR-EORTC-NCI 2011, Poster Abstract #6209, p. 1, United States (Nov. 2011).Accessed at: http://mct.aacrjournals.org/content/10/11_Supplement/B209.short on Jul. 20, 2015.

Stathis, A., et al., "Safety, Tolerability, and Preliminary Activity of IMGN529, a CD37-Targeted Antibody-Drug Conjugate, in Patients with Relapsed or Refractory B-Cell Non-Hodgkin Lymphoma: a Dose-Escalation, Phase I Study," Invest New Drugs, 36(5):869-876, Springer, United States (Oct. 2018).

NCT01534715, "IMGN529 in Treating Patients with Relapsed or Refractory Non-Hodgkin's Lymphoma," retrieved from https://clinical.gov/archive/NCT01534715/2012_02_16, retrieved on Sep. 6, 2016, 2 pages.

Oki, Y., et al., "Pegylated Liposomal Doxorubicin Replacing Conventional Doxorubicin in Standard R-CHOP Chemotherapy for Elderly Patients With Diffuse Large B-cell Lymphoma: an Open Label, Single Arm, Phase II Trial," Clinical Lymphoma, Myeloma & Leukemia 15:152-158, Elsevier, United States (Mar. 2015).

Paul, W.E., "Immunogenicity and Antigen Structure," in Fundamental Immunology, Third Edition, p. 242, Raven Press, United States (1993).

Rudolph, C., et al., "Molecular Cytogenetic Characterization of the Mantle Cell Lymphoma Cell Line GRANTA-519," Cancer Genetics and Cytogenetics 153(2):144-150, Elsevier, United States (2004).

Smolewski, P., et al., "Pro-apoptotic Effect of an Anti-cd37 Scfv-fc Fusion Protein, in Combination With the Anti-cd20 Antibody, Ofatumumab, on Tumour Cells From B-cell Malignancies," European Journal of Cancer 50(15):2677-2684, Elsevier, Netherlands (Oct. 2014).

Stathis, A. et al., "Preliminary Findings from a Phase I, Multicenter, Open-label Study of the anti-CD37 Antibody-Drug Conjugate (ADC), IMGN529, in Adult Patients with Relapsed or Refractory Non-Hodgkin Lymphoma (NHL)," 2014 ASCO Annual Meeting, Poster, Abstract No. 8526, United States (May 2014), 1 page Accessed at http://www.immunogen.com/documents/Publications/IMGN529%20first%20clin%20ASCO%202014.pdf on Aug. 26, 2015.

Stathis, A. et al., "A Phase I Study of IMGN529, An Antibody-Drug Conjugate (ADC) Targeting CD37, in Adult Patients With Relapsed or Refractory Non-Hodgkin Lymphoma (NHL)," 56th ASH Annual Meeting and Exposition: Abstract #1760, United States (Dec. 2014), 1 page Accessed at https://ash.confex.com/ash/2014/webprogram/Paper70219.html, on Aug. 26, 2015.

Stathis, A. et al., "A Phase I Study of IMGN529, An Antibody-Drug Conjugate (ADC) Targeting CD37, in Adult Patients With Relapsed or Refractory Non-Hodgkin Lymphoma (NHL)," Abstract #1760, 2014 ASH Annual Meeting, San Francisco, California, United States (Dec. 2014), 2 pages, accessed at http://www.immunogen.com/documents/Publications/IMGN529_Phl_ASH12-2014.pdf, accessed on Aug. 26, 2015.

Angelisová, P., et al., "Association of four antigens of the tetraspans family (CD37, CD53, TAPA-1, and R2/C33) with MHC class II glycoproteins," Immunogenetics 39:249-256, Springer-Verlag, Germany (1994).

Bernstein, I.D., et al., "High Dose Radiolabeled Antibody Therapy of Lymphoma," Cancer Research (Suppl.) 50:1017s-1021s, American Association for Cancer Research, United States (1990).

Braslawsky, G.R., et al., "Antitumor Activity of Adriamycin (Hydrazone-linked) Inhinunoconjugates Compared with Free Adriamycin and Specificity of Tumor Cell Killing," Cancer Research 50:6608-6614, American Association for Cancer Research, United States (1990).

Deckert, J., et al., "IMGN529: A therapeutic maytansinoid conjugate of an anti-CD37 antibody with multiple mechanisms of action for B-cell lymphoma and leukemia," AACR Poster Abstract #2, 1 page, (2011).

Deckert, J., et al., "IMGN529: An Anti-CD37 Antibody-Maytansinoid Conjugate with Multiple Mechanisms of Actions for B-Cell Malignancies," Poster #306, Keystone Symposis—B Cells: New Insights into Normal versus Dysregulated Function, Apr. 12-16, 2011, ImmunoGen, Inc., United States.

Deckert, J., et al., "Potent B-Cell Depletion by IMGN529, a CD37-Targeting Antibody-Maytansinoid Conjugate for the Treatment of B-Cell Malignancies," ASH Poster Abstract #3726:1-2 (2011).

Dijoseph, J.F., et al. "CD20-specific antibody-targeted chemotherapy of non-Hodgkin's B-cell lymphoma using calichearnicin-conjugated rituximab," Cancer Immunol Immunother 56:1107-1117, Springer-Verlag, Germany (2007).

Greenfield, R.S., et al., "Evaluation in Vitro of Adriamycin Immunoconjugates Synthesized Using an Acid-sensitive Hydrazone Linker," Cancer Research 50:6600-6607, American Association for Cancer Research, United States (1990).

International Search Report with Written Opinion for International Application No. PCT/US11/28172, International Searching Authority, United States, dated Jul. 13, 2011, 10 pages.

Kaminski, M.S., et al. "Imaging, Dosimetry, and Radioinununotherapy With Iodine 131-Labeled Anti-CD37 Antibody in B-Cell Lymphoma," Journal of Clinical Oncology 10(11):1696-1711, American Society of Clinical Oncology, United States (1992).

Knobeloch, K-P., et al., "Targeted Inactivation of the Tetraspanin CD37 Impairs T-Cell-Dependent B-Cell Response under Suboptimal Costimulatory Conditions," Molecular and Cellular Biology 20(15):5363-5369, American Society for Microbiology, United States (2000).

Lai, K.C., et al., "The CD37-targeting ADC IMGN529 combines the potent anti-cancer activity of K7153A antibody with efficient maytansinoid delivery," Poster Abstract #B209, AACR-EORTC-NCI 2011, ImmunoGen, Inc., United States (2011).

Lai, K.C., et al., "The CD37-targeting ADC IMGN529 combines the potent anti-cancer activity of K7153A antibody with efficient maytansinoid delivery," Oasis, The Online Abstract Submission System, Abstract 11-A-226-AACR:1-2, United States (2011).

Link, M.P., et al., "A Unique Antigen on Mature B Cells Defined by a Monoclonal Antibody," The Journal of Immunology 137(9):3013-3018, The American Association of Immunologists, United States (1986).

Maecker, H.T., et al., "The tetraspanin superfamily: molecular facilitators," FASEB J. 11:428-442, The Federation of American Societies for Experimental Biology, United States (1997).

Meyer-Wentrup, F., et al., "Dectin-1 Interaction with Tetraspanin CD37 Inhibits IL-6 Production," The Journal of Immunology 178:154-162, The American Association of Immunologists, Inc., United States (2007).

Moore, K., et al., "Use of the Monoclonal Antibody WR17, Identifying the CD37 40-45 Kd Antigen Complex, in the Diagnosis of

(56) References Cited

OTHER PUBLICATIONS

B-Lymphoid Malignancy," *Journal of Pathology* 152:13-21, John Wiley & Sons, Ltd., England (1987).

Park, P.U., et al., "Antibody and linker selection for the anti-CD37 antibody-maytansinoid conjugate IMGN529 for the treatment of B-cell malignancies," *Experimental and Molecular Therapeutics session*, Abstract #2830:1-24, AACR Annual Meeting 2011, ImmunoGen, Inc. (2011).

Pinkas, J., "Antibody Maytansinoid Conjugates for the Treatment of Cancer," Protein Therapeutics Forum 2012:1-23, ImmunoGen, Inc., United States (2012).

Polson, A.G., et al., "Antibody-Drug Conjugates for the Treatment of Non-Hodgkin's Lymphoma: Target and Linker-Drug Selection," *Cancer Res* 69(6):2358-2364, American Association for Cancer Research, United States (2009).

Press, O.W., et al., "Endocytosis and Degradation of Monoclonal Antibodies Targeting Human B-Cell Malignancies," *Cancer Research* 49:4906-4912, American Association for Cancer Research, United States (1989).

Press, O.W., et al., "Radiolabeled-Antibody Therapy of B-Cell Lymphoma with Autologous Bone Marrow Support," *N Engl J Med* 329(17):1219-1224, Massachusetts Medical Society, United States (1993).

Press, O.W., et al., "Retention of B-Cell-Specific Monoclonal Antibodies by Human Lymphoma Cells," *Blood* 83(5):1390-1397, The American Society of Hematology (1994).

Press, O.W., et al., "Treatment of Refractory Non-Hodgkin's Lymphoma With Radiolabeled MB-1 (Anti-CD37) Antibody," *J Clin Oncol* 7(8):1027-1038, American Society of Clinical Oncology, United States (1989).

Rops, A.L., et al., "The Tetraspanin CD37 Protects Against Glomeiular IgA Deposition and Renal Pathology," *Am J Pathol* 176:2188-2197, American Society for Investigative Pathology (May 2010).

Schwartz-Albiez, R., et al., "The B Cell-Associated CD37 Antigen (gp40-52): Structure and Subcellular Expression of an Extensively Glycosylated Glycoprotein," *The Journal of Immunology* 140(3):905-914, The American Association of Immunologists, United States (1988).

Sheng, K-C., et al., "Tetraspanins CD37 and CD151 differentially regulate Ag presentation and T-cell co-stimulation by DC," *Eur. J. Immunol.* 39:50-55, Wiley-VCH Verlag GmbH & Co. KGaA, Germany (2009).

Van Spriel, A.B., et al., "A Regulatory Role for CD37 in T Cell Proliferation," *The Journal of Immunology* 172:2953-2961, The American Association of Immunologists, United States (2004).

Van Spriel, A.B., et al., "The Tetraspanin Protein CD37 Regulates IgA Responses and Anti-Fungal Immunity," *PLoS Pathogens* 5(3) e1000338:1-11, Public Library of Science, United States (2009).

Tedder, T.F., et al., "Structure of the Gene Encoding the Human B Lymphocyte Differentiation Antigen CD20 (B1)," *The Journal of Immunology* 142(7):2560-2568, The American Association of Immunologists, United States (1989).

Zhao, X., et al., "Targeting CD37-positive lymphoid malignancies with a novel engineered small modular immunopharmaceutical," *Blood* 110(7):2569-2577, The American Society of Hematology, United States (2007).

Awan, F., et al., "Phase 1 Study of TRU-016, an Anti-CD37 SMIP Protein in Naïve and Relapsed and/or Refractory CLL Patients," Poster (2011).

Awan, F.T, et al., "Phase 1 Study of TRU-016, an Anti-CD37 SMIP™ Protein in Naïve and Relapsed and/or Refractory CLL Patients," *Blood (ASH Annual Meeting Abstracts)* 2011 118:Abstract 1792 (2011).

Barrena, S., et al., "Aberrant expression of tetraspanin molecules in B-cell chronic lymphoproliferative disorders and its correlation with normal B-cell maturation," *Leukemia* 19:1376-1383, Nature Publishing Group, England (2005).

Blanc, V., et al., "SAR3419: An Anti-CD19-Maytansinoid Immunoconjugate for the Treatment of B-Cell Malignancies," *Clin Cancer Res* 17(20):6448-6458, American Association for Cancer Research, United States (2011).

Heider, K-H., et al., "A novel Fc-engineered monoclonal antibody to CD37 with enhanced ADCC and high proapoptotic activity for treatment of B-cell malignancies," *Blood* 118(15):4159-4168, The American Society of Hematology, United States (2011).

Lambert, J.M., "Antibody-Maytansinoid Conjugates: A New Strategy for the Treatment of Cancer," *Drugs of the Future* 35(6):471-480, Prous Science, S.A.U., Spain (Jun. 2010).

Pagel, J.M, et al., "Phase 1 Study of TRU-016, An Anti-CD37 SMIP™ Protein in Relapsed and/or Refractory NHL Patients," *Blood (ASH Annual Meeting Abstracts)* 2011 118(21):Abstract 1636 (2011).

Roguska, M.A., et al., "A comparison of two murine monoclonal antibodies humanized by CDR-grafting and variable domain resurfacing," *Protein Engineering* 9(10):895-904, Oxford University Press, England (1996).

Roguska, M.A., et al., "Humanization of murine monoclonal antibodies through variable domain resurfacing," *Proc. Natl. Acad. Sci. USA* 91:969-973, National Academy of Sciences, United States (1994).

Teicher, B.A. and Chari, R.V.J., "Antibody Conjugate Therapeutics: Challenges and Potential," *Clin Cancer Res* 17(20):6389-6397, American Association for Cancer Research, United States (2011).

Dahle, J., et al., "Evaluating Antigen Targeting and Anti-tumor Activity of a New Anti-CD37 Radioimmunoconjugate Against Non-Hodgkin's Lymphoma," *Anticancer Research* 33:85-96, International Institute of Anticancer Research, Greece (2013).

Lapalombella, R., et al., "Tetraspanin CD37 Directly Mediates Transduction of Survival and Apoptotic Signals," *Cancer Cell* 21:694-708, Elsevier Inc., United States (2012).

Zhao, X.B., et al., "Novel Anti-CD37 Small Modular Immunopharmaceutical (SMP) Induces B-Cell-Specific, Caspase-Independent Apoptosis in Human CLIJ Cells," *Blood* 104, Abstract 2515, ASII Annual Meeting, American Society of Hematology, United States (2004).

International Search Report with Written Opinion for International Application No. PCT/US2016/048887, International Searching Authority, United States, dated Nov. 28, 2016, 8 pages.

Preissuance Submission by Third Party under 37 C.F.R. § 1.290, filed in U.S. Appl. No. 13/045,693, filed Mar. 11, 2011.

Kovtun, Y., et al. "Antibody-Maytansinoid Conjugates Designed to Bypass Multidrug Resistance," *Cancer Research* 70(6):2528-2537, American Association for Cancer Research, United States (Mar. 2010).

Cragg, M.S., et al., "Complement-mediated lysis by anti-CD20 mAb correlates with segregation into lipid rafts," *Blood* 101(3):1045-1052, American Society of Hematology, United States (2003).

Business Wire, "ImmunoGen, Inc. Announces Presentations at the 102nd Annual Meeting of the American Associated for Cancer Research," May 30, 2011, accessed at http://files.shareholder.comjdownloads/ABEA-5VU3S1/0x0x500536/b6f7f6a6-1853-4476-93cf-2f2f895241d7/IMGN_News_2011_3_30_General_Releases.pdf, accessed on Dec. 8, 2014.

Beckwith, K.A., et al., "The CD37-targeted antibody-drug conjugate IMGN529 is highly active against human CLL and in a novel CD37 transgenic murine leukemia model," *Leukemia* 28(7):1501-1510, Nature Publishing Group, England (Jul. 2014).

Yu, B., et al., "Targeted drug delivery and cross-linking induced apoptosis with anti-CD37 based dual-ligand immunoliposomes in B chronic lymphocytic leukemia cells," Biomaterials 34(26):6185-6193, Elsevier Science, Netherlands (2013).

Deckert, J., et al., "A novel anti-CD37 antibody-drug conjugate with multiple anti-tumor mechanisms for the treatment of B-cell malignancies," *Blood* 122(20):3500-3510 American Society of Hematology, United States (2013).

Harris, C.L., et al., "Tumour cell killing using chemically engineered antibody constructs specific for tumour cells and the complement inhibitor CD59," *Clinical & Experimental Immunology* 107(2):364-371, Blackwell Publishing, England (1997).

(56) References Cited

OTHER PUBLICATIONS

Altschuler, E.P., et al., "Method for obtaining recombinant antibodies and for improving affinities thereof", *Uspehi biologicheskoi himii* 50: 203-258, Pleiades Publishing Ltd., Russia (Dec. 2010).
Altschuler, E.P., et al., "Generation of Recombinant Antibodies and Means for Increasing Their Affinity," *Biochemistry (Moscow)* 75(13):1584-1605, Pleiades Publishing, Ltd , Russia (Dec. 2010).
Zhao, X., "Targeting CD37 and folate receptor for cancer therapy: strategies based on engineered proteins and liposomes," Europe PubMed Central, accessed at http://europepmc.org/theses/ETH/6183, accessed on Dec. 9, 2014 (2007) [Thesis 6183], 314 pages.
Preissuance Submission by Third Party under 37 C.F.R. § 1.290, filed in U.S. Appl. No. 13/796,768, filed Mar. 12, 2013.
Preissuance Submission by Third Party under 37 C.F.R. § 1.290, filed in U.S. Appl. No. 13/436,528, filed Mar. 30, 2012.
De Pascalis, R., et al., "Grafting of 'Abbreviated' Complementarity-Determining Regions Containing Specificity-Determining Residues Essential for Ligand Contact to Engineer a Less Immunogenic Humanized Monoclonal Antibody," Journal of Immunology 169(6):3076-3084, The American Association of Immunologists, United States (2002).
International Preliminary Report on Patentability for International Application No. PCT/US2012/031648, The International Bureau of WIPO, Switzerland, dated Oct. 2, 2013, pp. 1-9.
International Search Report and Written Opinion for International Application No. PCT/US2013/034646, Commissioner for Patents, United States, dated Sep. 16, 2013, pp. 1-15.
Maccallum, R.M., et al., "Antibody-Antigen Interactions: Contact Analysis and Binding Site Topography," Journal of Molecular Biology 262(5):732-745, Elsevier, England (1996).
Supplementary European Search Report for Application No. EP11754195, dated Sep. 10, 2013, pp. 1-7.
Zhao, X.B., et al., "Novel Anti-CD37 Small Modular Immunopharmaceutical (SMIP) Induces B-Cell-Specific, Caspase-Independent Apoptosis in Human CLL Cells," Blood 104, Abstract 2515, p. 1 , ASII Annual Meeting, American Society of Hematology, United States (2004). Accessed at http://abstracts.hematologylibrary.org/cgi/content/short/104/11/2515 on Jul. 16, 2015.
Zhao Xiaoxian et al: "CD37 Is a Potential Therapeutic Target for B-Cell Non-Hodgkin Lymphoma.", Blood, 116(21), pp. 1277-1278, American Society of Hematology, United States (Nov. 2011); 52nd Annual Meeting of the American-Society-Of Hematology(Ash); Orlando, FL, USA; Dec. 4-7, 2010 Accessed at https://ash.confex.com/ash/2010/webprogram/Paper28315.html, on Nov. 13, 2015.
Extended European Search Report and written opinion for EP Application No. 13 77 0074, The Hague, The Netherlands, completed on Oct. 20, 2015, pp. 1-9.
International Search Report and Written Opinion for International Application No. PCT/US15/30371, Commissioner for Patents, United States, dated Nov. 2, 2015, pp. 1-10.
Robak T. et. al., TRU-016, "A humanized anti-CD37 IgG fusion protein for the potential treatment of B-cell malignancies", Curr Opin Investig Drugs. 2009. V.10. No. 12, p. 1383-1390, Current Drugs Ltd. England (2009).
Office Action dated Aug. 11, 2015 in Russian Patent Application No. 2012139045/10 (063108), filed Mar. 11, 2011, Applicant: Immunogen, Inc., US.
Morris, G.E., "Epitope Mapping of Protein Antigens by Competition Elisa," *The Protein Protocols Handbook* 1:595-600, Humana Press, United States (1996).
Marken, J., et al., "Membrane Topology of the L6 Antigen and Identification of the Protein Epitope Recognized by the L6 Monoclonal Antibody," *Journal of Biological Chemistry* 269: 7397-401, The American Society for Biochemistry and Molecular Biology, Inc., United States (1994).
International Preliminary Report on Patentability for International Application No. PCT/US2016/048887, International Searching Authority, United States, dated Nov. 29, 2016, 5 pages.

International Search Report and Written Opinion for International Application No. PCT/US16/035558, Commissioner for Patents, United States, dated Sep. 7, 2016, pp. 1-11.
Beers, S.A., et al., "Type II (Tositumomab) Anti-CD20 Monoclonal Antibody Out Performs Type I (Rituximab-Like) Reagents in B-Cell Depletion Regardless of Complement Activation," *Blood* 112(10):4170-4177, American Society of Hematology, United States (2008).
Bissery, M., et al., "Experimental Antitumor Activity of Taxotere (RP 56976, NSC 628503), a Taxol Analogue," *Cancer Research* 51(18):4845-4852, American Association for Cancer Research, United States (1991).
Boross, P. and Leusen, J.H., "Mechanisms of Action of CD20 Antibodies," *American Journal of Cancer Research* 2(6):676-690, e-Century Publishing Corporation, United States (2012).
Cheson, B.D., et al., "Revised Response Criteria for Malignant Lymphoma," *Journal of Clinical Oncology* 25(5):579-586, American Society of Clinical Oncology, United States (2007).
Friedberg, J.W., "Double-Hit Diffuse Large B-cell Lymphoma," *Journal of Clinical Oncology* 30(28):3439-3443, American Society of Clinical Oncology, United States (2012).
Green, T.M., et al., "Immunohistochemical Double-Hit Score Is a Strong Predictor of Outcome in Patients with Diffuse Large B-cell Lymphoma Treated with Rituximab Plus Cyclophosphamide, Doxorubicin, Vincristine, and Prednisone," *Journal of Clinical Oncology* 30(28):3460-3467, American Society of Clinical Oncology, United States (2012).
Hu, S., et al., "MYC/BCL2 Protein Coexpression Contributes to the Inferior Survival of Activated B-Cell Subtype of Diffuse Large B-Cell Lymphoma and Demonstrates High-Risk Gene Expression Signatures: a Report from the International DLBCL Rituximab-CHOP Consortium Program," *Blood* 121(20):4021-4031, American Society of Hematology, United States (2013).
Lai, K.C., et al., "Evaluation of Targets for Maytansinoid Adc Therapy Using a Novel Radiochemical Assay," *Pharmaceutical Research* 32(11):3593-3603, Kluwer Academic, United States (Nov. 2015).
Lim, S.H., et al., "Anti-CD20 Monoclonal Antibodies: Historical and Future Perspectives," *Haematologica* 95(1):135-143, Ferrata Storti Foundation, Italy (Jan. 2010).
Pers, J.O., et al., "Anti-CD20 Antibody-Mediated Apoptosis of B Cells Is a Lipid Raft-Dependent Process," *Annals of the Rheumatic Diseases* 70(Suppl 2):A73, BMJ Publishing Group Ltd (Feb. 2011).
Robak, T. and Robak, E., "New Anti-CD20 Monoclonal Antibodies for the Treatment of B-cell Lymphoid Malignancies," *BioDrugs* 25(1):13-25, Springer International, New Zealand (Feb. 2011).
Tomayko. M.M. and Reynolds, C.P., "Determination of Subcutaneous Tumor Size in Athymic (Nude) Mice," *Cancer Chemotherapy and Pharmacology* 24(3):148-154, Springer Verlag, Germany (1989).
Smith et al., "2006 update of recommendations for the use of white blood cell growth factors: an evidence-based clinical practice guideline," *J. Clin. Oncol.* 24: 3187-3205, American Society of Clinical Oncology, United States (2006).
Romanelli, A., et al., Novel CD37-Targeting Antibody-Drug Conjugate (ADC), IMGN529, Has Synergistic Activity in Combination with Rituximab in Non-Hodgkin Lymphoma (NHL) Models, presented at 13th International Conference on Malignant Lymphoma, Jun. 17-20, 2015, 1 page.
Deckert, et al., IMGN529, a Novel Antibody-Drug Conjugate (ADC) Targeting CD37 Shows Synergistic Activity with Rituximab in Non-Hodgkin Lymphoma (NHL) Models, poster # 1548, 1 page, 57th ASH Annual Meeting and Exposition, Dec. 5, 2015, Orlando, United States.
Co, M.S., et al., "Chimeric and Humanized antibodies with specificity for the CD33 antigen," *Journal of immunology* 148(4):1149-1154, American Association of Immunologists, United States (1992).
Tedoldi, S., et al., "Selective loss of B-cell phenotype in lymphocyte predominant Hodgkin Lymphoma," Journal of Pathology 213:429-440, Pathological Society of Great Britain and Ireland, Britain (2017).
Office Action dated Jan. 21, 2016 in U.S. Appl. No. 13/436,528, inventors Deckert, J., et al., filed Mar. 30, 2012, 8 pages.
Office Action dated Sep. 8, 2015 in U.S. Appl. No. 13/436,528, inventors Deckert, J., et al., filed Mar. 30, 2012, 8 pages.

(56) References Cited

OTHER PUBLICATIONS

Office Action dated Mar. 30, 2015 in U.S. Appl. No. 13/436,528, inventors Deckert, J., et al., filed Mar. 30, 2012, 10 pages.
Office Action dated Mar. 7, 2014 in U.S. Appl. No. 13/436,528, inventors Deckert, J., et al., filed Mar. 30, 2012, 14 pages.
Office Action dated Dec. 11, 2015 in U.S. Appl. No. 13/796,768, inventors Deckert, J., et al., filed Mar. 12, 2013, 8 pages.
Office Action dated Sep. 3, 2015 in U.S. Appl. No. 13/796,768, inventors Decked, J., et al., filed Mar. 12, 2013, 11 pages.
International Search Report with Written Opinion for International Application No. PCT/IB2017/056841, International Searching Authority, Netherlands, dated Feb. 2, 2018, 14 pages.
International Preliminary Report on Patentability for International Application No. PCT/US16/035558, International Search Authority, Switzerland, dated Dec. 12, 2017, 8 pages.
Smith, S.M., et al., "The Impact of MYC expression in Lymphoma biology: Beyond Burkitt lymphoma," Blood Cells, Molecules, and Diseases 45:317-323, Elsevier, Netherlands (Dec. 2010).
Poosarla, V., et al., "Computational De Novo Design of Antibodies Binding to a Peptide with High Affinity," Biotechnology and Bioengineering 114(6):1331-1342, Wiley Periodicals, United States (2007).
Office Action dated May 29, 2018 in U.S. Appl. No. 15/171,732, inventors Romanelli, A., et al., filed Jun. 2, 2016, 29 pages.
Office Action dated Oct. 25, 2017 in U.S. Appl. No. 15/171,732, inventors Romanelli, A., et al., filed Jun. 2, 2016, 24 pages.
Office action dated Jul. 2, 2018, U.S. Appl. No. 15/233,423, inventors Deckert, J., et a., filed Aug. 10, 2016, 9 pages.
Goel, M., et al., "Plasticity within the Antigen-Combining Site May Manifest as Molecular Mimicry in the Humoral Immune Response," J. Immunol 173:7358-7367, American Association of immunologists, United States (2004).
Khan, T., et al., "Adjustable Locks and Flexibile Keys: Plasticity of Epitope-Paratope Interactions in germline Antibodies," J Imrnunol. 192:5398-5405, American Association of immunologists, United States (2014).
Rudikoff, S., et al., "Single Amino Acid Substitution Altering Antigen-Binding Specificity," Proc. Natl. Acad. Sci 79:1979-1983, United States National Academy of Sciences,United States (1982).
Mariuzza, R.A., et al., "The Structural Basis of Antigen-Antibody Recognition," *Ann. Rev. Biophys. Chem* 16:139-159, Annual Reviews, United States (1987).
Lippincott-Schwartz (Current Protocols in Cell Biology) pp. 16.0.1-16.0.2, (2002).
Gussow, D., et al., "Humanization of Monoclonal Antibodies," *Methods in Enzymology* 203:99-121, Elsevier, Netherlands (1991).
Wang, Z., et al., "Universal PCR amplification of mouse immunoglobulin gene variable regions: the design of degenerate primers and an assessment of the effect of DNA polymerase 3' to 5' exonuclease activity," *Journal of Immunological methods* 233:167-177, Elsevier, Netherlands (200).
Daniel, C., et al., "Mapping of Linear Antigenic Sites on the S Glycoprotein of a Neurotropic Murine Coronavirus with Synthetic Peptides: A combination of Nine Prediction Algorithms Fails to Identify Relevant Epitopes and Peptide Immunogenicity is Drastically Influenced by the Nature of the Protein Carrier," *Virology* 202: 540-549, Elsevier, Netherlands (1994).
Greenspan, N.S., et al., "Defining epitopes: It's not as easy as it seems," *Nature Biotechnology* 17: 936-937, Nature America Inc., United States (1999).
Angeletti, R.H., "Design of Useful Peptide Antigens," *Journal of Biomolecular Techniques* 10(1):2-10, Association of Biomolecular Resource Facilities, United States (1999).
International Search Report and Written Opinion for International Application No. PCT/US2012/031648, The International Bureau of WIPO, Switzerland, dated Oct. 2, 2013, 16 pages.
Heppner, G.H., et al., "Tumor heterogeneity: biological implications and therapeutic consequences," Cancer Metastasis Reviews 2:5-23, Martinus Nijhoff Publishers, Netherlands (1983).
Jain, R.K., "Barriers to Drug Delivery in Solid Tumors," Scientific American: 271:58-65, Scientific American Inc., United States (Jul. 1994).

| Antibody | Concentration | hCD37-Fc-LAGA | | hCD37-ECD-Fc | | hCD37-LEL | |
|---|---|---|---|---|---|---|---|
| | | native | denatured | native | denatured | native | denatured |
| 1B11 | supernatant | 3.0 | 3.1 | 3.0 | 3.1 | 3.0 | 1.7 |
| Leica NCL-CD37 | 10 µg/mL | 2.8 | 3.2 | 2.7 | 3.1 | 3.0 | 2.8 |
| | 5 µg/mL | 2.6 | 3.1 | 2.4 | 3.1 | 3.0 | 2.0 |
| | 2.5 µg/mL | 2.4 | 3.1 | 2.2 | 3.1 | 3.0 | 1.8 |

FIG. 1A

| Antibody | Concentration | hCD37-Fc-LAGA | | hCD37-LEL | |
|---|---|---|---|---|---|
| | | Native | Denatured-Reduced | Native | Denatured-Reduced |
| 1B11-2 | supernatant | 3.3 | 3.3 | 3.2 | 3.3 |
| 1B11-20 | supernatant | 3.2 | 3.2 | 3.2 | 3.2 |
| Leica NCL-CD37 | 10 µg/mL | 2.9 | 3.3 | 2.7 | 3.3 |
| | 5 µg/mL | 2.5 | 3.2 | 2.4 | 3.2 |
| | 2.5 µg/mL | 2.1 | 3.2 | 2.0 | 3.2 |

FIG. 1B

ANTIBODIES AND ASSAYS FOR DETECTION OF CD37

CROSS REFERENCE TO RELATED APPLICATIONS

This application is a national phase entry of International Application No. PCT/US2016/048887, filed Aug. 26, 2016, which claims the priority benefit of U.S. Provisional Application No. 62/211,455, filed Aug. 28, 2015, and U.S. Provisional Application No. 62/212,183, filed Aug. 31, 2015, each of which is hereby incorporated by reference herein in its entirety.

REFERENCE TO A SEQUENCE LISTING SUBMITTED ELECTRONICALLY VIA EFS-WEB

The content of the electronically submitted sequence listing (Name: 4018_00300002_ST25.txt; Size: 43,346 bytes; and Date of Creation: Feb. 24, 2018) is herein incorporated by reference in its entirety.

FIELD OF THE INVENTION

The field of this invention generally relates to diagnostic assays and kits for CD37-based therapies and antibodies that bind to human CD37.

BACKGROUND OF THE INVENTION

Cancer is one of the leading causes of death in the developed world, with over one million people diagnosed with cancer and 500,000 deaths per year in the United States alone. Overall it is estimated that more than 1 in 3 people will develop some form of cancer during their lifetime.

Leukocyte antigen CD37 ("CD37"), also known as GP52-40, tetraspanin-26, or TSPAN26, is a transmembrane protein of the tetraspanin superfamily (Maecker et al., 1997 FASEB J. 11:428-442). It is a heavily glycosylated protein with four transmembrane domains that is expressed on B cells during the pre-B to peripheral mature B-cell stages, but is absent on terminal differentiation to plasma cells. (Link et al., 1987, J Pathol. 152:12-21). The CD37 antigen is only weakly expressed on T-cells, myeloid cells and granulocytes (Schwartz-Albiez et al. 1988, J. Immunol. 140(3)905-914). However, CD37 is also expressed on malignant B-cells such as those founding non-Hodgkin's lymphoma (NHL) and chronic lymphoid leukemia (CLL) (Moore et al. 1986, J Immunol. 137(9):3013-8). This expression profile suggests that CD37 represents a promising therapeutic target for B-cell malignancies that express CD37. However, in order for these therapies to be maximally effective, it is necessary to be able to detect a dynamic range of CD37 with sensitivity and specificity.

BRIEF SUMMARY OF THE INVENTION

Anti-CD37 antibodies and antigen-binding fragments thereof as well as methods for detecting CD37, diagnosing CD37-mediated diseases and disorders (such as cancer), monitoring the efficacy of anti-CD37 therapies, and stratifying patients are all provided herein. The anti-CD37 antibodies and antigen-binding fragments thereof are particularly advantageous in that they allow for more specific and defined staining as well as staining without nuclear background. The CD37 antibodies and antigen-binding fragments thereof can bind to an epitope that includes one or more amino acids 110-137 of CD37. The CD37 antibodies and antigen-binding fragments thereof can also bind to a polypeptide comprising amino acids 107-242 of CD37 (SEQ ID NO:20) and/or to a polypeptide comprising amino acids 107-235 of CD37 (SEQ ID NO:19), but do not bind to a polypeptide consisting of amino acids 138-235 of CD37.

In one embodiment, an antibody or antigen-binding fragment thereof provided herein specifically binds to the same CD37 epitope as an antibody comprising the polypeptide of SEQ ID NO:9 and the polypeptide of SEQ ID NO:10.

In another embodiment, an antibody or antigen-binding fragment thereof provided herein specifically binds to CD37, and competitively inhibits binding to CD37 of an antibody comprising the polypeptide of SEQ ID NO:9 and the polypeptide of SEQ ID NO:10.

In another embodiment, the an antibody or antigen-binding fragment thereof provided herein comprises the heavy chain variable region CDR1, CDR2, and CDR3 sequences of SEQ ID NOs: 3-5, respectively, and the light chain variable region CDR1, CDR2, and CDR3 sequences of SEQ ID NOs: 6-8, respectively.

In another embodiment, an antibody or antigen-binding fragment thereof provided herein specifically binds to CD37, and the antibody or fragment thereof comprises the heavy chain variable region CDR1, CDR2, and CDR3 sequences of SEQ ID NOs: 3-5 and the light chain variable region CDR1, CDR2, and CDR3 sequences of SEQ ID NOs: 6-8, respectively.

In another embodiment, the an antibody or antigen-binding fragment thereof provided herein comprises polypeptide sequences that are at least 90% identical to the polypeptide sequences of SEQ ID NOs:9 and 10. In another embodiment, the polypeptide sequences are at least 95% identical to the polypeptide sequences of SEQ ID NOs:9 and 10. In another embodiment, the polypeptide sequences are at least 99% identical to the polypeptide sequences of SEQ ID NOs:9 and 10. In another embodiment, the polypeptide sequences comprise the amino acids of sequences of SEQ ID NOs:9 and 10.

In another embodiment, an antibody or antigen-binding fragment thereof provided herein specifically binds to CD37, wherein the antibody or fragment thereof comprises a heavy chain variable region comprising SEQ ID NO:9.

In another embodiment, an antibody or antigen-binding fragment thereof provided herein specifically binds to CD37, wherein the antibody or fragment thereof comprises a heavy chain variable region comprising SEQ ID NO:10.

In another embodiment, an antibody or antigen-binding fragment thereof provided herein is recombinantly produced. In another embodiment, the antibody or antigen-binding fragment thereof is murine, non-human, humanized, chimeric, or human. In another embodiment, the antibody or antigen-binding fragment thereof is resurfaced. In another embodiment, the antibody or antigen-binding fragment thereof is a full length antibody. In another embodiment, the antibody or antigen-binding fragment thereof is an antigen-binding fragment. In another embodiment, the antibody or antigen-binding fragment thereof comprises a Fab, Fab', F(ab')2, Fd, single chain Fv or scFv, disulfide linked Fv, V-NAR domain, IgNar, intrabody, IgGΔCH2, minibody, F(ab')3, tetrabody, triabody, diabody, single-domain antibody, DVD-Ig, Fcab, mAb2, (scFv)2, or scFv-Fc. In another embodiment, the antibody or antigen-binding fragment thereof comprises a Fab, Fab', F(ab')2, single chain Fv or scFv, disulfide linked Fv, intrabody, IgGΔCH2, minibody, F(ab')3, tetrabody, triabody, diabody, DVD-Ig, mAb2, (scFv)2, or scFv-Fc.

In another embodiment, the antibody or antigen-binding fragment is produced by a cell. In another embodiment, the cell is isolated. In another embodiment, a method of making an antibody or antigen-binding fragment thereof is provided herein, wherein the method comprises (a) culturing the cell; and (b) isolating the antibody or antigen-binding fragment thereof from the cultured cell.

In another embodiment, the antibody or antigen-binding fragment thereof binds to a human CD37 with a Kd of about 0.5 to about 10 nM. In another embodiment, the antibody or antigen-binding fragment thereof binds to a human CD37 with a Kd of about 1.0 nM or better.

In another embodiment, the an antibody or antigen-binding fragment thereof which binds to a polypeptide comprising, consisting essentially of, or consisting of amino acids 107-242 of CD37 (SEQ ID NO:20). In another embodiment, the antibody or antigen-binding fragment thereof binds to a polypeptide comprising, consisting essentially of, or consisting of amino acids 107-235 of CD37 (SEQ ID NO:19). In another embodiment, the antibody or antigen-binding fragment thereof binds to the sequence set forth in SEQ ID NO:15. In another embodiment, the antibody or antigen-binding fragment thereof binds to the sequence set forth in SEQ ID NO:16. In another embodiment, the antibody or antigen-binding fragment thereof binds to the sequence set forth in SEQ ID NO:17. In another embodiment, the antibody or antigen-binding fragment thereof binds to a polypeptide comprising amino acids 107-242 of CD37 (SEQ ID NO:20) but does not bind to a polypeptide consisting of amino acids 138-235 of CD37. In another embodiment, the antibody or antigen-binding fragment thereof binds to a polypeptide comprising amino acids 107-235 of CD37 (SEQ ID NO:19) but does not bind to a polypeptide consisting of amino acids 138-235 of CD37.

In another embodiment, an antibody or antigen-binding fragment provided herein binds to a polypeptide of SEQ ID NO:15, but does not bind to a polypeptide of SEQ ID NO:18. In another embodiment, the antibody or antigen-binding fragment thereof binds to a polypeptide of SEQ ID NO:16, but does not bind to a polypeptide of SEQ ID NO:18. In another embodiment, the antibody or antigen-binding fragment thereof binds to a polypeptide of SEQ ID NO:17, but does not bind to a polypeptide of SEQ ID NO:18. In another embodiment, the antibody or antigen-binding fragment thereof binds to at least one amino acid in amino acids 110-137 of CD37.

In another embodiment, the binding affinity of the antibody or antigen-binding fragment thereof is measured by flow cytometry, Biacore, ELISA, or radioimmunoassay.

In another embodiment, the antibody or antigen-binding fragment thereof is detectably labeled. In another embodiment, the label is selected from the group consisting of an immunofluorescent label, a chemiluminescent label, a phosphorescent label, an enzyme label, a radiolabel, avidin/biotin, a colloidal gold particle, a colored particle, and a magnetic particle.

In another embodiment, a composition is provided herein, wherein the composition comprises the antibody or antigen-binding fragment thereof and a buffer selected from the group consisting of: an IHC buffer, an ELISA buffer, and a FACS buffer.

In another embodiment, a method of detecting CD37 expression in a sample is provided herein, wherein the method comprises contacting the sample with an antibody or antigen-binding fragment thereof or a composition provided herein. In another embodiment, the antibody or antigen-binding fragment thereof is detectably labeled. In another embodiment, the label is selected from the group consisting of an immunofluorescent label, a chemiluminescent label, a phosphorescent label, an enzyme label, a radiolabel, avidin/biotin, a colloidal gold particle, a colored particle, and a magnetic particle. In another embodiment, the label is an enzyme label.

In another embodiment, the CD37 expression is determined by radioimmunoassay, Western blot assay, cytometry, immunofluorescent assay, enzyme immunoassay, immunoprecipitation assay, chemiluminescent assay, or immunohistochemical assay. In another embodiment, the CD37 expression is determined by immunohistochemical assay.

In another embodiment, a method for increasing the efficacy of cancer therapy with a therapeutically active agent comprising an anti-CD37 antibody or antigen-binding fragment thereof is provided herein, wherein said method comprises administering the therapeutically active agent to a subject having cancer, wherein increased expression of CD37 has been detected in a cancerous sample from the subject using an antibody or antigen-binding fragment thereof or a composition provided herein.

In another embodiment, a method for identifying a cancer as likely to respond to a therapeutically active agent comprising an anti-CD37 antibody or antigen-binding fragment thereof, is provided, wherein the method comprises: (a) contacting a biological sample comprising cells from the cancer with an antibody or antigen-binding fragment thereof or a composition; (b) detecting binding of the antibody or antigen-binding fragment thereof to CD37 in the biological sample of (a); (c) assigning a score to the binding of step (b), wherein the score is assigned based on comparison to one or more reference samples; and (d) comparing the score in step (c) to the score of a reference tissue or cell, wherein a score for the cancer CD37 level that is greater than the score for a normal or low CD37 expressing reference sample or a score for the cancer CD37 level that is equal to or greater than the score for a high CD37 expressing reference sample identifies the cancer as likely to respond to an anti-CD37 antibody.

In another embodiment, a method of treating a patient having cancer is provided herein, wherein the method comprises: (a) determining a CD37 expression score from a detection of CD37 expression in a cancerous sample obtained from the patient, wherein the detection is performed using an antibody or antigen-binding fragment thereof or a composition; and (b) administering a therapeutically active agent comprising an anti-CD37 antibody or antigen-binding fragment thereof to the patient if the score indicates the patient will benefit from administration of the therapeutically active agent.

In another embodiment, a method of treating a patient having cancer comprises: (a) determining a CD37 expression score from a detection of CD37 expression in a cancerous sample obtained from the patient, wherein the detection is performed using an antibody or antigen-binding fragment thereof or a composition; and (b) instructing a healthcare provider to administer a therapeutically active agent comprising an anti-CD37 antibody or antigen-binding fragment thereof to the patient if the score indicates the patient will benefit from administration of the therapeutically active agent.

In another embodiment, a method of treating a patient having cancer comprises: (a) submitting a cancerous sample taken from a patient having cancer for determining a CD37 expression score from a detection of CD37 expression using an antibody or antigen-binding fragment thereof or a composition; and (b) administering a therapeutically active agent comprising an anti-CD37 antibody or antigen-binding fragment thereof to the patient if the score indicates the patient will benefit from administration of the therapeutically active agent.

In another embodiment, a method of treating a patient having cancer comprises: (a) detecting CD37 expression in a cancerous sample obtained from the patient, wherein the detection is performed using an antibody or antigen-binding fragment thereof or a composition; (b) determining a CD37 expression score for the cancerous sample; and (c) administering a therapeutically active agent comprising an anti-CD37 antibody or antigen-binding fragment thereof to the patient if the score indicates the patient will benefit from administration of the therapeutically active agent.

In another embodiment, a method of identifying a cancer as sensitive to treatment with an anti-CD37 active agent comprises: (a) detecting the level of CD37 expression in a cancerous sample from the cancer using an antibody or antigen-binding fragment thereof or a composition, wherein the detecting comprises the use of a method that distinguishes between staining intensity or staining uniformity in a CD37 expressing cancerous sample as compared to staining intensity or staining uniformity in one or more reference samples; (b) determining a CD37 staining intensity or staining uniformity score for the cancerous sample; and (c) comparing the CD37 staining intensity or staining uniformity score determined in step (b) to a relative value determined by measuring CD37 protein expression in at least one reference sample, wherein the at least one reference sample is a tissue, cell, or cell pellet sample which is not sensitive to treatment with a therapeutically active agent comprising an anti-CD37 antibody or antigen-binding fragment thereof and wherein a CD37 staining intensity score for the cancerous sample determined in step (b) that is higher than the relative value identifies the cancer as being sensitive to treatment with the therapeutically active agent.

In another embodiment, a method of identifying a cancer as sensitive to treatment with a therapeutically active agent comprising an anti-CD37 antibody or antigen-binding fragment thereof, comprises: (a) detecting the level of CD37 expression in a cancerous sample from the cancer using an antibody or antigen-binding fragment thereof or a composition, wherein the detecting comprises the use of a method that distinguishes between staining intensity or staining uniformity in a CD37 expressing cancerous sample as compared to staining intensity or staining uniformity in one or more reference samples; (b) determining a CD37 staining intensity or staining uniformity score for the cancerous sample; and (c) comparing the CD37 staining intensity or staining uniformity score determined in step (b) to a relative value determined by measuring CD37 protein expression in at least one reference sample, wherein the at least one reference sample is a tissue, cell, or cell pellet sample which is sensitive to treatment with a therapeutically active agent comprising an anti-CD37 antibody or antigen-binding fragment thereof and wherein a CD37 staining intensity score for the cancerous sample determined in step (b) that is greater than or equal to the relative value identifies the cancer as being sensitive to treatment with the therapeutically active agent.

In another embodiment, the method which further comprises administering a therapeutically active agent comprising an anti-CD37 antibody or antigen-binding fragment thereof to the subject from whom the cancerous sample or biological sample was obtained. In another embodiment, the patient's CD37 level is detected in a cancerous sample or biological sample obtained from the patient. In another embodiment, the cancerous sample or biological sample is a fluidic extract, blood, plasma, serum, spinal fluid, lymph fluid, or a splenic preparation. In another embodiment, the detecting is by immunohistochemistry (IHC). In another embodiment, the IHC is calibrated IHC that can distinguish different levels of CD37 expression. In another embodiment, the IHC produces a range of staining intensity for samples having low CD37 expression, moderate CD37 expression, or high CD37 expression. In another embodiment, the IHC distinguishes between staining intensity and staining uniformity in a CD37 expressing cancerous sample or biological sample as compared to a reference sample. In another embodiment, the IHC is performed manually. In another embodiment, the IHC is performed using an automated system. In another embodiment, a CD37 score is determined from the IHC. In another embodiment, the detecting is by enzyme linked immunosorbent assay (ELISA). In another embodiment, the reference sample is a positive reference sample or a negative reference sample. In another embodiment, the reference sample comprises cells, cell pellets, or tissue.

In another embodiment, the antibody or antigen-binding fragment thereof further comprises a detection reagent selected from the group consisting of: an immunofluorescent label, a chemiluminescent label, a phosphorescent label, an enzyme, a radiolabel, avidin/biotin, a colloidal gold particle, a colored particle, and a magnetic particle. In another embodiment, the detection reagent is an enzyme.

In another embodiment, the cancer is a CD37 positive cancer. In another embodiment, the cancer is a leukemia or a lymphoma. In another embodiment, the cancer is selected from the group consisting of wherein the cancer is selected from the group consisting of B cell lymphomas, NHL, precursor B cell lymphoblastic leukemia/lymphoma and mature B cell neoplasms, B cell chronic lymphocytic leukemia (CLL)/small lymphocytic lymphoma (SLL), B cell prolymphocytic leukemia, lymphoplasmacytic lymphoma, mantle cell lymphoma (MCL), follicular lymphoma (FL), low grade, intermediate-grade and high-grade (FL), cutaneous follicle center lymphoma, marginal zone B cell lymphoma, MALT type marginal zone B cell lymphoma, nodal marginal zone B cell lymphoma, splenic type marginal zone B cell lymphoma, hairy cell leukemia, diffuse large B cell lymphoma (DLBCL), Burkitt's lymphoma, plasmacytoma, plasma cell myeloma, post-transplant lymphoproliferative disorder, Waldenstrom's macroglobulinemia, and anaplastic large-cell lymphoma (ALCL). In another embodiment, the CD37 positive cancer is diffuse large B-cell lymphoma, follicular lymphoma, or mantle cell lymphoma.

In another embodiment, the CD37 expression is detected using at least one additional anti-CD37 antibody or antigen-binding fragment thereof. In another embodiment, the CD37 expression is measured using two anti-CD37 antibodies or antigen-binding fragments thereof. In another embodiment, the at least one additional antibody or antigen-binding fragment thereof comprises a detection agent. In another embodiment, the detection agent is a chromogenic detection agent, a fluorogenic detection agent, an enzymatic detection agent, or an electrochemiluminescent detection agent. In another embodiment, the detection agent is horseradish peroxidase (HRP).

In another embodiment, the at least one additional antibody or antigen-binding fragment thereof is bound to a solid support. In another embodiment, the at least one additional antibody or antigen-binding fragment thereof is bound to a microtiter plate.

In another embodiment, the ELISA is a sandwich ELISA.

In another embodiment, the therapeutically active agent comprises the CD37 antibody huCD37-3. In another embodiment, the therapeutically active agent is an antibody maytansinoid conjugate comprising the CD37 antibody huCD37-3, the maytansinoid DM1, and the non-cleavable SMCC linker (IMGN529).

In another embodiment, a combination diagnostic and pharmaceutical kit is provided herein, wherein the kit comprises an antibody or antigen-binding fragment thereof or composition provided herein for use in diagnosis and a therapeutically active agent comprising an anti-CD37 antibody or antigen-binding fragment thereof for use in therapy.

In another embodiment, the detection antibody is able to detect CD37 expression by IHC. In another embodiment, the detection antibody is able to detect CD37 expression by ELISA.

In another embodiment, the anti-CD37 antibody in the therapeutically active agent is conjugated to a cytotoxin.

In another embodiment, a diagnostic kit provided herein comprises an antibody, antigen-binding fragment thereof provided herein, a reagent for IHC, and one or more standardized reference samples, wherein the standardized reference samples comprise cells, cell pellets, or formalin fixed paraffin embedded tissue samples, and wherein the one or more standardized referenced samples are from non-CD37 expressing, low-CD37 expressing, or high CD37 expressing cells, cell pellets, or tissues.

BRIEF DESCRIPTION OF THE DRAWINGS/FIGURES

FIGS. 1A and 1B provide ELISA screening results for antibodies produced by immunization of mice with hCD37-LEL (Large Extracellular Loop) protein (SEQ ID NO:15), which contains amino acids 107 to 242 of human CD37 fused to a His-tag. FIG. 1A shows that supernatant from hybridoma clone 1B11 binds to multiple versions of the CD37 antigen, hCD37-LEL, hCD37-Fc-LAGA (LAGA refers to the Fc mutations G236A and P238A), SEQ ID NO:17, containing amino acids 107 to 235 of human CD37 fused to human IgG1 Fc-domain), and hCD37-ECD-Fc (Extra Cellular Domain, SEQ ID NO:16, containing amino acids 107 to 235 of human CD37 fused to murine IgG2a Fc-domain), under both native and denaturing conditions. FIG. 1B shows that supernatant from two hybridoma subclones, 1B11-2 and 1B11-20, bind to hCD37-Fc-LAGA and hCD37-LEL under both native and denaturing conditions.

Figure 5:
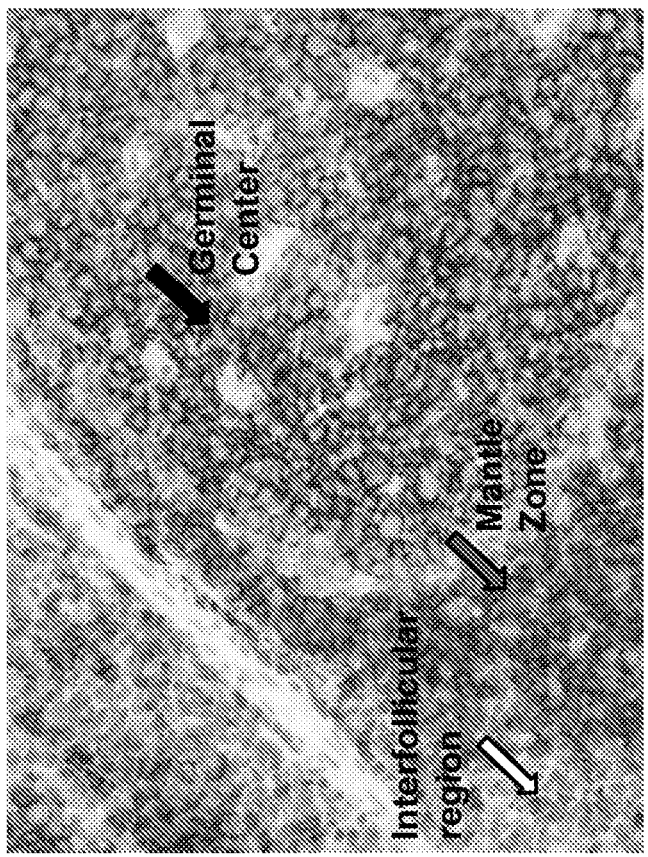
Figure 5:
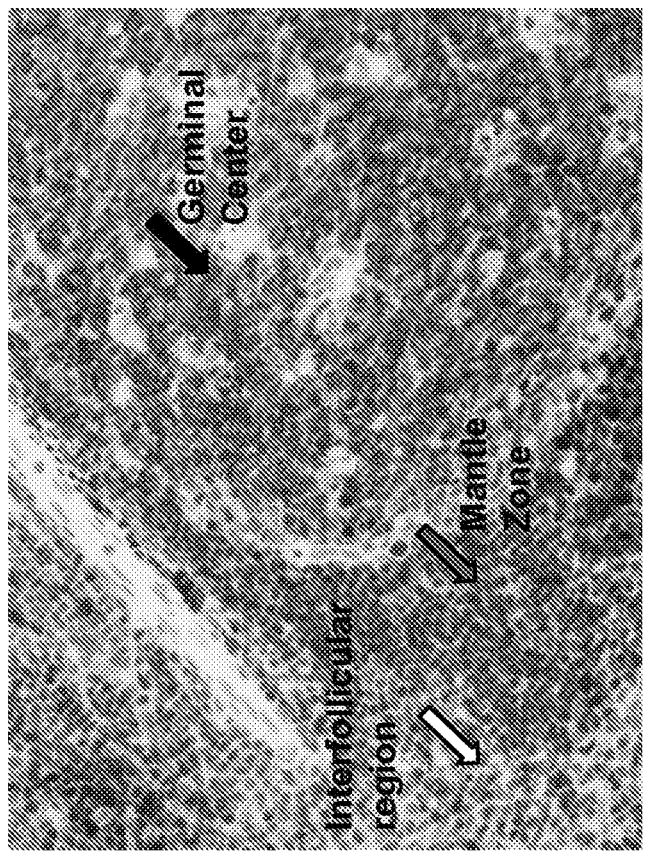

FIG. 5 shows immunohistochemical images of human normal tonsil stained with either NCL-CD37 Mouse mAb (left) or CD37 1B11-2 Mouse mAb (right). The arrows indicate the germinal centers, the mantle zones (both of which are CD37 positive), and the intermolecular regions (CD37 negative), respectively. Black arrows indicate the germinal centers; gray arrows mantle zone (both of which are CD37 positive); and open arrows indicate the interfollicular regions (which are negative for CD37). Nuclear staining is present in both the germinal center and the mantel zone using the NCL-CD37 antibody. No nuclear staining is present using the 1B11-2 antibody.

Figure 6:
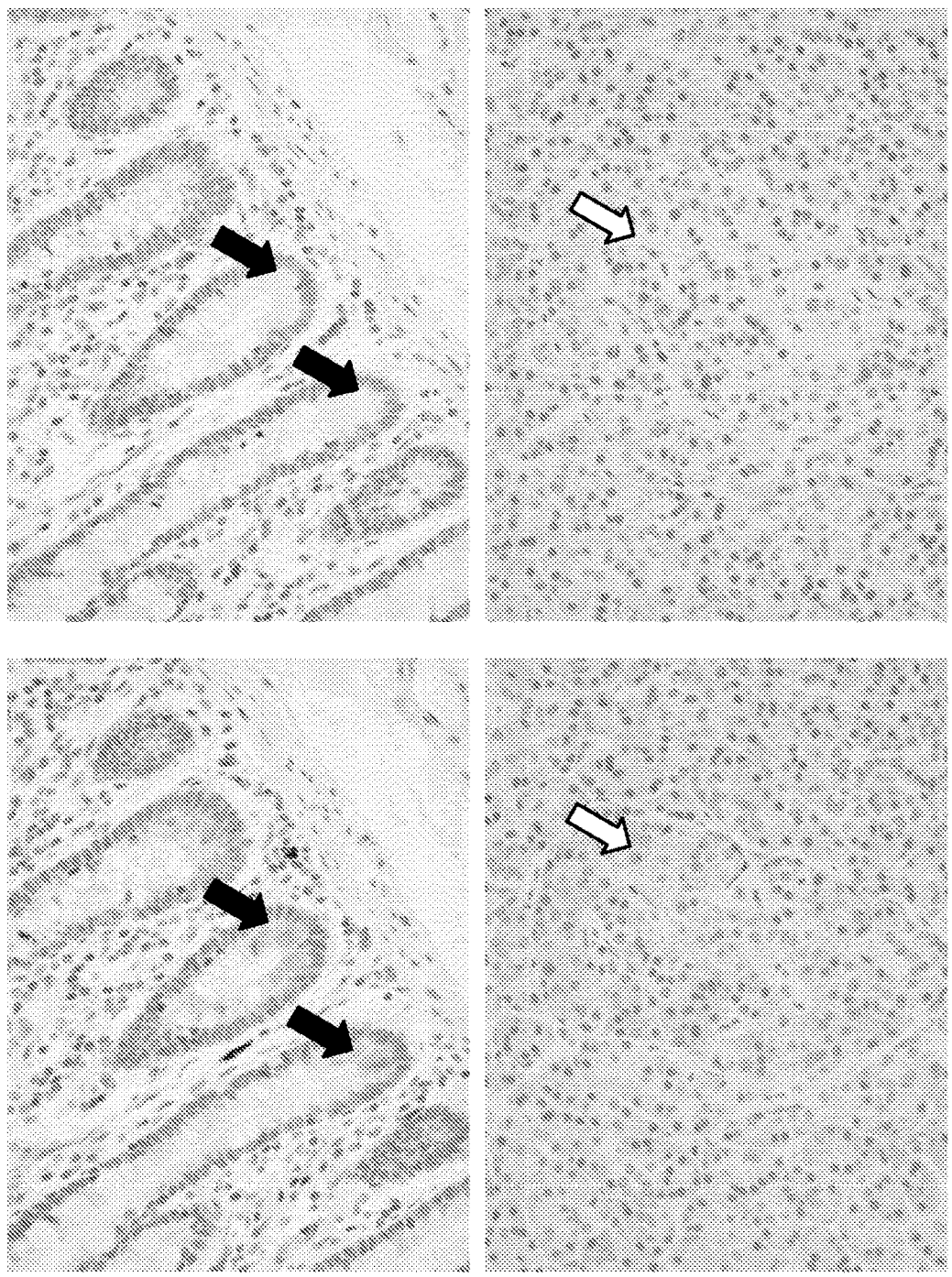

FIG. 6 shows immunohistochemical images of human normal small intestine (upper panel) and human normal pancreas (lower panel) using either NCL-CD37 Mouse monoclonal antibody (mAb) (left panel) or 1B11-2 Mouse mAb (right panel). Arrows in the left panels denote cytoplasmic blush in paneth cells (upper panel, indicated with black arrows) and islet cells (lower panel, indicated with open arrows) obtained using the NCL-CD37 Mouse mAb. Arrows in the right panels demonstrates that this staining is not observed in corresponding locations using the 1B11-2 antibody.

Figure 7:
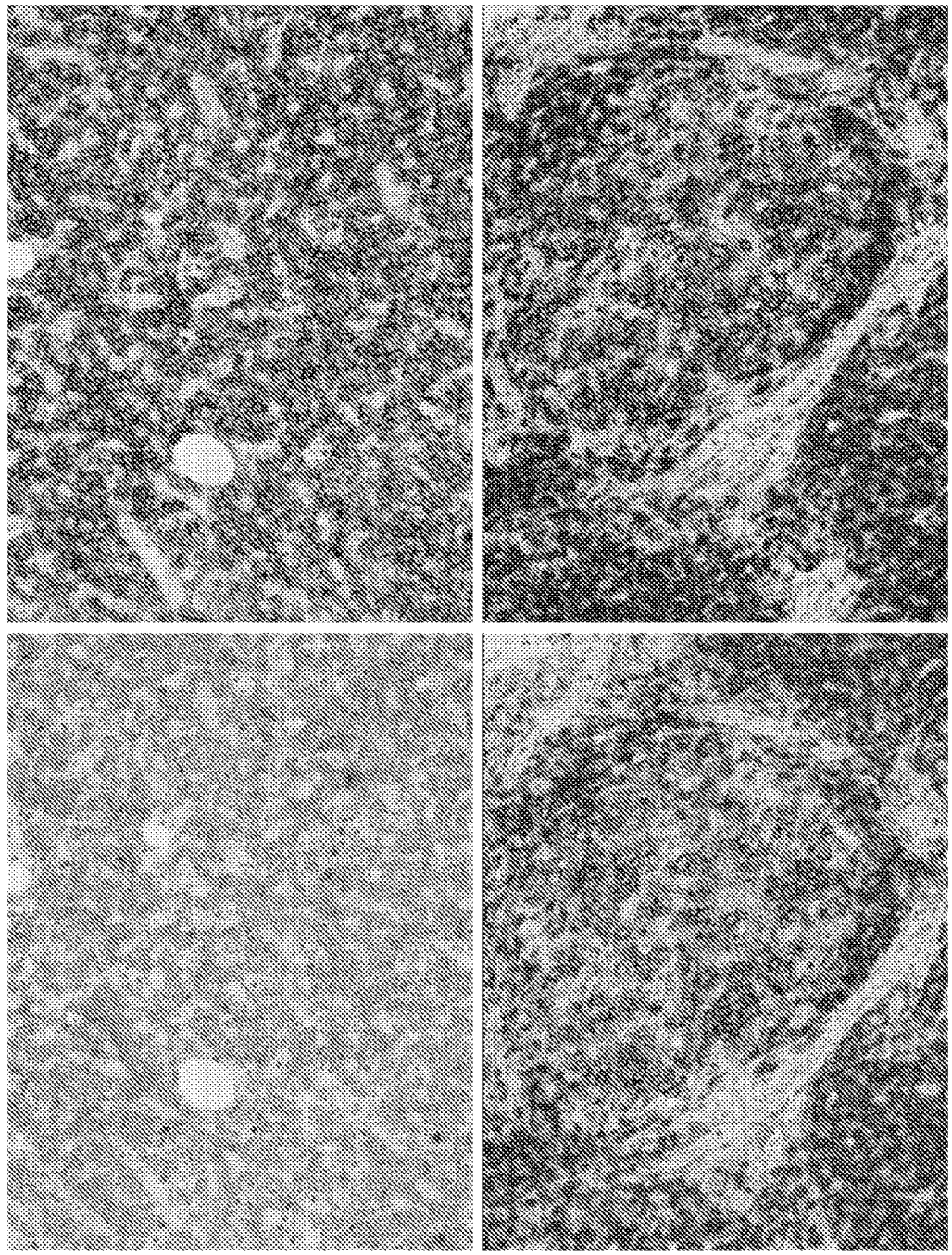

FIG. 7 shows immunohistochemical images of diffuse large B cell lymphoma patient tissue (upper panel) and follicular lymphoma patient tissue (lower panel) stained with either NCL-CD37 Mouse mAb (left panel) or 1B11-2 Mouse mAb (right panel). Stronger, more crisp staining is visible in both cancer types using the 1B11-2 Mouse mAb.

Figure 8:
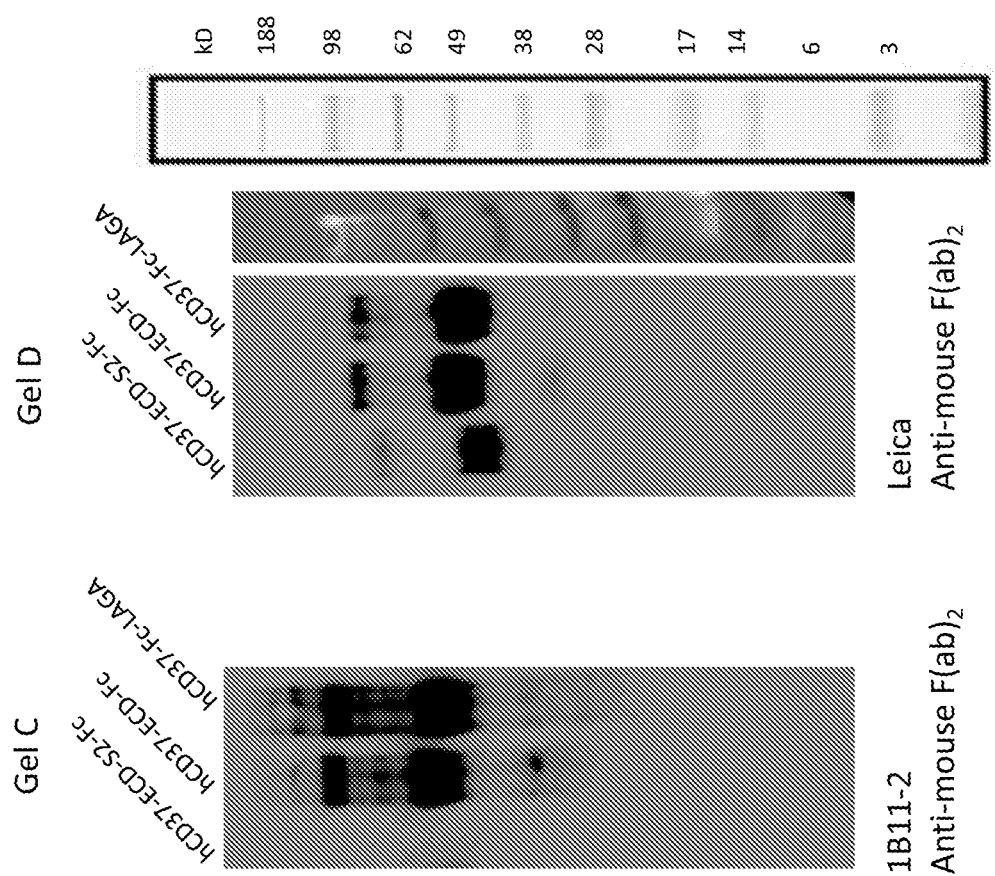

FIG. 8 shows denaturing SDS PAGE Western blots of Fc-fusions to the CD37 extracellular domain (ECD) antigens comparing the 1B11-2 mouse monoclonal antibody to a commercially available mouse monoclonal anti-CD37 antibody (Leica). Molecular weight markers in kilo Dalton (kD) are shown as primary data and as a schematic depiction on the right.

Figure 9:
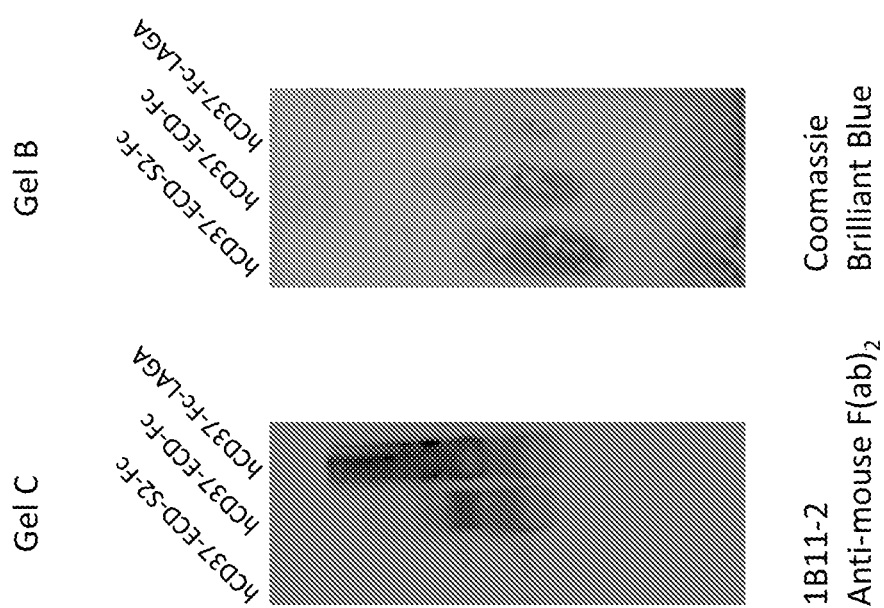

FIG. 9 shows Native PAGE Western blots of Fc-fusions to CD37 extracellular domain (ECD) antigens detected by 1B11-2 mouse monoclonal antibody.

DETAILED DESCRIPTION OF THE INVENTION

The present disclosure provides methods of detecting human CD37. These methods allow for the identification of cancers characterized by the expression of CD37 in order to improve the efficacy of treatment with anti-CD37 therapeutics. The detection methods can be used for patient stratification, to monitor or determine therapeutic efficacy, or to determine the likelihood of a cancer to respond to an anti-CD37 therapy. The detection methods can detect a clinically relevant dynamic range of CD37. Novel CD37-binding polypeptides, such as antibodies and antigen-binding fragments thereof, that are useful in the CD37 detection methods (e.g., immunohistochemistry (IHC) for CD37) are also disclosed. The CD37 binding agent (e.g., an antibody or antigen-binding fragment thereof) provided herein allows for more specific and defined staining without nuclear background. The CD37 binding agent binds to an epitope that includes one or more amino acids 110-137 of CD37. The CD37 binding agent also binds to a polypeptide comprising amino acids 107-242 of CD37 (SEQ ID NO:20) or to a polypeptide comprising amino acids 107-235 of CD37 (SEQ ID NO:19) but does not bind to a polypeptide consisting of amino acids 138-235 of CD37. Related polypeptides and polynucleotides, compositions comprising the CD37-binding agents, and methods of making the CD37-binding agents are also provided.

I. DEFINITIONS

To facilitate an understanding of the present invention, a number of terms and phrases are defined below.

The term "CD37" as used herein, refers to any native CD37, unless otherwise indicated. CD37 is also referred to as GP52-40, leukocyte antigen CD37, and Tetraspanin-26. The term "CD37" encompasses "full-length," unprocessed CD37 as well as any form of CD37 that results from processing in the cell. The term also encompasses naturally occurring variants of CD37, e.g., splice variants, allelic variants, and isoforms. The CD37 polypeptides described herein can be isolated from a variety of sources, such as from human biological samples or from another source, or prepared by recombinant or synthetic methods.

The term "increased expression" or "overexpression" of CD37 refers to a sample which contains elevated levels of CD37 expression. The CD37 can be increased or overexpressed as compared to a negative or low reference control or as compared to a healthy or non-diseased sample of the same tissue or cell type. Such increased expression or overexpression can be caused, for example, by mutation, gene amplification, increased transcription, increased translation, or increased protein stability.

In one example, the CD37 expression is measured by immunohistochemistry (IHC) and given a staining intensity score or a staining uniformity score by comparison to calibrated controls exhibiting defined scores (e.g., an intensity score of 3 is given to the test sample if the intensity is comparable to the level 3 calibrated control or an intensity of 2 is given to the test sample if the intensity is comparable to the level 2 calibrated control). A staining uniformity that is heterogeneous or homogeneous is also indicative of increased CD37 expression. The staining intensity and staining uniformity scores can be used alone or in combination (e.g., 2 homo, 2 hetero, 3 homo, 3 hetero, etc.). In another example, an increase in CD37 expression can be determined by detection of an increase of at least 2-fold, at least 3-fold, or at least 5-fold relative to control values (e.g., expression level in a biological sample, tissue, or cell from a subject without cancer or with a cancer that does not have elevated CD37 values). In another example, CD37 expression is given an H-score. H-scores combine staining intensity scores with uniformity scores using the calculation provided herein. In another example, CD37 expression is measured by determining the percentage of cells that have at least a particular level of staining (e.g., at least 25% of cells have a score of at least 2 or at least 75% of cells have a score of at least 2).

A "reference sample" can be used to correlate and compare the results obtained in the methods provided herein to a test sample. Reference samples can be cells (e.g., cell lines, cell pellets) or tissue. The CD37 levels in the "reference sample" can be an absolute or relative amount, a range of amounts, a minimum and/or maximum amount, a mean amount, and/or a median amount of CD37. The diagnostic methods provided herein involve a comparison between expression levels of CD37 in a test sample and a "reference value." In some embodiments, the reference value is the expression level of the CD37 in a reference sample. A reference value can be a predetermined value and can also be determined from reference samples (e.g., control biological samples or reference samples) tested in parallel with the test samples. A reference value can be a single cut-off value, such as a median or mean or a range of values, such as a confidence interval. Reference values can be established for various subgroups of individuals, such as individuals predisposed to cancer, individuals having early or late stage cancer, male and/or female individuals, or individuals undergoing cancer therapy. Examples of negative reference samples or values and positive reference samples or values are described herein.

In some embodiments, the reference sample is a sample from a healthy tissue, in particular a corresponding tissue which is not affected by cancer or a corresponding tissue which is not affected by a cancer that overexpresses CD37. These types of reference samples are referred to as negative control samples or reference samples. In other embodiments, the reference sample is a sample from a tumor that expresses CD37. These types of reference samples are referred to as positive control samples. Positive control samples can also be used as a comparative indicator for the type (hetero versus homo), degree (0, 1, 2, 3) of staining intensity, H-score, and/or percent of cells with at least a particular level of staining, which correlates with the level of CD37 expression. Positive control comparative samples are also referred to as calibrated reference samples. Low or non-CD37 references are described herein in the Examples and also include the red pulp of the spleen (e.g., monocytes and red blood cells), T-cells, and the interfolicular region of human tonsils. CD37-expressing references are described herein in the Examples and also include white pulp of the spleen (e.g., B lymphocytes and the marginal zone of the spleen), the germinal center of human tonsils, and the mantle zone of human tonsils. For cell lines, exemplary non-expressors include 300-19 cells, and expressors include Daudi, Ramos, Namalwa, and RL non-Hodgkin's lymphoma B cells. Another positive high CD37 reference is a cell line stably or transiently transfected with CD37 (e.g., 300.19/CD37, as described in U.S. Published Application No. 2015/0093397 and PCT publication WO 2013/149171, each of which is incorporated herein by reference). Appropriate positive and negative reference levels of CD37 for a particular cancer can be determined by measuring levels of CD37 in one or more appropriate subjects, and such reference levels may be tailored to specific populations of subjects (e.g., a reference level may be age-matched so that comparisons may be made between CD37 levels in samples from subjects of a certain age and reference levels for a particular disease state, phenotype, or lack thereof in a certain age group).

As used herein, "immunohistochemistry" refers to histochemical and immunologic methods used to analyze, for example, cells or tissues. Thus, the terms "immunohistochemistry," "immunocytochemistry," and "immunochemistry" are used interchangeably.

A "sample" or "biological sample" of the present invention is of biological origin, in specific embodiments, such as from eukaryotic organisms. In some embodiments, the sample is a human sample, but animal samples can also be used in the practice of the invention. Non-limiting sources of a sample for use in the present invention include solid tissue, biopsy aspirates, fluidic extracts, blood, plasma, serum, spinal fluid, lymph fluid, the external sections of the skin, respiratory, intestinal, and genitourinary tracts, tears, saliva, milk, tumors, organs, cell cultures and/or cell culture constituents, for example. A "cancerous sample" is a sample that contains a cancerous cell. The methods provided herein can be useful for solid tissue samples where the amount of available material is small. The methods provided herein can be used to examine an aspect of expression of CD37 or a state of a sample, including, but not limited to, comparing different types of cells or tissues and detecting or determining the presence and/or type of disease or abnormality.

For the purposes herein, a "section" of a tissue sample refers to a single part or piece of a tissue sample, e.g., a thin slice of tissue or cells cut from a tissue sample. It is understood that multiple sections of tissue samples may be taken and subjected to analysis according to the present invention. In some cases, the selected portion or section of tissue comprises a homogeneous population of cells. In other cases, the selected portion comprises a region of tissue, e.g., the lumen as a non-limiting example. The selected portion can be as small as one cell or two cells, or could represent many thousands of cells, for example. In most cases, the collection of cells is important, and while the invention has been described for use in the detection of cellular components, the method can also be used for detecting non-cellular components of an organism (e.g., soluble components in the blood as a non-limiting example).

As used herein, the term "capture reagent" refers to a reagent capable of binding and capturing a target molecule in a sample such that under suitable condition, the capture reagent-target molecule complex can be separated from the rest of the sample. In one embodiment, the capture reagent is immobilized. In one embodiment, the capture reagent in a sandwich immunoassay is an antibody or antigen-binding fragment thereof or a mixture of different antibodies or antigen-binding fragments thereof against a target antigen.

As used herein, the term "detectable" antibody or antigen-binding fragment thereof refers to an antibody or antigen-binding fragment thereof that is capable of being detected either directly through a label amplified by a detection means, or indirectly through, e.g., another antibody or antigen-binding fragment thereof that is labeled. For direct labeling, the antibody or antigen-binding fragment thereof is typically conjugated to a moiety that is detectable by some means. In one embodiment, the detectable antibody or antigen-binding fragment thereof is a biotinylated antibody or antigen-binding fragment thereof.

As used herein, the term "detection means" refers to a moiety or technique used to detect the presence of the detectable antibody or antigen-binding fragment thereof and includes detection agents that amplify the immobilized label such as label captured onto a microtiter plate. In one embodiment, the detection means is a fluorimetric detection agent such as avidin or streptavidin.

Commonly a "sandwich ELISA" employs the following steps: (1) microtiter plate is coated with a capture antibody or antigen-binding fragment thereof; (2) sample is added, and any antigen present binds to capture antibody or antigen-binding fragment thereof; (3) detecting antibody or antigen-binding fragment thereof is added and binds to antigen; (4) enzyme-linked secondary antibody or antigen-binding fragment thereof is added and binds to detecting antibody or antigen-binding fragment thereof; and (5) substrate is added and is converted by enzyme to detectable form.

The word "label" when used herein refers to a detectable compound or composition which is conjugated directly or indirectly to the antibody so as to generate a "labeled" antibody. The label can be detectable by itself (e.g. radioisotope labels or fluorescent labels) or, in the case of an enzymatic label, can catalyze chemical alteration of a substrate compound or composition which is detectable.

By "correlate" or "correlating" is meant comparing, in any way, the performance and/or results of a first analysis with the performance and/or results of a second analysis. For example, one may use the results of a first analysis in carrying out the second analysis and/or one may use the results of a first analysis to determine whether a second analysis should be performed and/or one may compare the results of a first analysis with the results of a second analysis.

In one embodiment, increased expression of CD37 correlates with increased likelihood of effectiveness of a CD37-targeting anti-cancer therapy.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, multi specific antibodies such as bispecific antibodies generated from at least two intact antibodies, chimeric antibodies, humanized antibodies, human antibodies, fusion proteins comprising an antibody, and any other modified immunoglobulin molecule so long as the antibodies exhibit the desired biological activity. An antibody can be of any the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

The term "antibody fragment" refers to a portion of an intact antibody. An "antigen-binding fragment" refers to a portion of an intact antibody that binds to an antigen. An antigen-binding fragment can contain the antigenic determining variable regions of an intact antibody. Examples of antibody fragments include, but are not limited to Fab, Fab', F(ab')2, and Fv fragments, linear antibodies, and single chain antibodies. Examples of antibody fragments encompassed within the term "antigen-binding fragment" of an antibody include (without limitation): (i) a Fab fragment, a monovalent fragment consisting of the VL, VH, CL and CH1 domains (e.g., an antibody digested by papain yields three fragments: two antigen-binding Fab fragments, and one Fc fragment that does not bind antigen); (ii) a $F(ab')_2$ fragment, a bivalent fragment comprising two Fab fragments linked by a disulfide bridge at the hinge region (e.g., an antibody digested by pepsin yields two fragments: a bivalent antigen-binding $F(ab')_2$ fragment, and a pFc' fragment that does not bind antigen) and its related F(ab') monovalent unit; (iii) a Fd fragment consisting of the VH and CH1 domains (i.e., that portion of the heavy chain which is included in the Fab); (iv) a Fv fragment consisting of the VL and VH domains of a single arm of an antibody, and the related disulfide linked Fv; and (v) a dAb (domain antibody) or sdAb (single domain antibody) fragment (Ward et al., Nature 341:544-546, 1989), which consists of a VH domain.

In some embodiments, an antibody or antigen-binding fragment thereof is a non-naturally occurring antibody. In some embodiments, an antibody or an antigen-binding fragment thereof is purified from natural components. In some embodiments, an antibody or an antigen-binding fragment thereof is recombinantly produced. In some embodiments, an antibody or an antigen-binding fragment thereof is produced by a hybridoma.

A "blocking" antibody or an "antagonist" antibody is one which inhibits or reduces biological activity of the antigen it binds, such as CD37. In a certain embodiment blocking antibodies or antagonist antibodies substantially or completely inhibit the biological activity of the antigen. Desirably, the biological activity is reduced by 10%, 20%, 30%, 50%, 70%, 80%, 90%, 95%, or even 100%.

The term "anti-CD37 antibody" or "an antibody that binds to CD37" refers to an antibody that is capable of binding CD37 with sufficient affinity such that the antibody is useful as a diagnostic and/or therapeutic agent in targeting CD37. The extent of binding of an anti-CD37 antibody to an unrelated, non-CD37 protein is less than about 10% of the binding of the antibody to CD37 as measured, e.g., by a radioimmunoassay (RIA). In certain embodiments, an antibody that binds to CD37 has a dissociation constant (Kd) of ≤1 μM, ≤100 nM, ≤10 nM, ≤1 nM, or ≤0.1 nM. Examples of anti-CD37 antibodies are known in the art and are disclosed, for example, in U.S. Published Application No 2011/0256153, which is herein incorporated by reference.

A "monoclonal" antibody or antigen-binding fragment thereof refers to a homogeneous antibody or antigen-binding fragment population involved in the highly specific recognition and binding of a single antigenic determinant, or epitope. This is in contrast to polyclonal antibodies that typically include different antibodies directed against different antigenic determinants. The term "monoclonal" antibody or antigen-binding fragment thereof encompasses intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal" antibody or antigen-binding fragment thereof refers to such antibodies and antigen-binding fragments thereof made in any number of manners including but not limited to by hybridoma, phage selection, recombinant expression, and transgenic animals.

The term "humanized" antibody or antigen-binding fragment thereof refers to forms of non-human (e.g., murine) antibodies or antigen-binding fragments that are specific immunoglobulin chains, chimeric immunoglobulins, or fragments thereof that contain minimal non-human (e.g., murine) sequences. Typically, humanized antibodies or antigen-binding fragments thereof are human immunoglobulins in which residues from the complementary determining region (CDR) are replaced by residues from the CDR of a non-human species (e.g., mouse, rat, rabbit, hamster) that have the desired specificity, affinity, and capability (Jones et al., 1986, Nature, 321:522-525; Riechmann et al., 1988, Nature, 332:323-327; Verhoeyen et al., 1988, Science, 239: 1534-1536). In some instances, the Fv framework region (FR) residues of a human immunoglobulin are replaced with the corresponding residues in an antibody or fragment from a non-human species that has the desired specificity, affinity, and capability. The humanized antibody or antigen-binding fragment thereof can be further modified by the substitution of additional residues either in the Fv framework region and/or within the replaced non-human residues to refine and optimize antibody or antigen-binding fragment thereof specificity, affinity, and/or capability. In general, the humanized antibody or antigen-binding fragment thereof will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody or antigen-binding fragment thereof can also comprise at least a portion of an immunoglobulin constant region or domain (Fc), typically that of a human immunoglobulin. Examples of methods used to generate humanized antibodies are described in U.S. Pat. Nos. 5,225,539 or 5,639,641.

The term "primary" antibody or antigen-binding fragment thereof herein refers to an antibody or antigen-binding fragment thereof that binds specifically to the target protein antigen in a sample. A primary antibody or antigen-binding fragment thereof is generally the first antibody or antigen-binding fragment thereof used in an immunohistochemical procedure. In one embodiment, the primary antibody or antigen-binding fragment thereof is the only antibody or antigen-binding fragment thereof used in an immunohistochemical procedure. The term "secondary" antibody or antigen-binding fragment thereof herein refers to an antibody or antigen-binding fragment thereof that binds specifically to a primary antibody or antigen-binding fragment thereof, thereby forming a bridge between the primary antibody or antigen-binding fragment thereof and a subsequent reagent, if any. The secondary antibody or antigen-binding fragment thereof is generally the second antibody or antigen-binding fragment thereof used in an immunohistochemical procedure. The term "tertiary" antibody herein refers to an antibody or antigen-binding fragment thereof that binds specifically to a secondary antibody or antigen-binding fragment thereof, thereby forming a bridge between the secondary antibody or antigen-binding fragment thereof and a subsequent reagent, if any.

A "variable region" of an antibody or antigen-binding fragment thereof refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al (1997) *J. Molec. Biol.* 273:927-948)). In addition, combinations of these two approaches are sometimes used in the art to determine CDRs.

The Kabat numbering system is generally used when referring to a residue in the variable domain (approximately residues 1-107 of the light chain and residues 1-113 of the heavy chain) (e.g., Kabat et al., Sequences of Immunological Interest. 5th Ed. Public Health Service, National Institutes of Health, Bethesda, Md. (1991)).

The amino acid position numbering as in Kabat, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence can contain fewer or additional amino acids corresponding to a shortening of, or insertion into, a FR or CDR of the variable domain. For example, a heavy chain variable domain can include a single amino acid insert (residue 52a according to Kabat) after residue 52 of H2 and inserted residues (e.g., residues 82a, 82b, and 82c, etc. according to Kabat) after heavy chain FR residue 82. The Kabat numbering of residues can be determined for a given antibody by alignment at regions of homology of the sequence of the antibody with a "standard" Kabat numbered sequence. Chothia refers instead to the location of the structural loops (Chothia and Lesk J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software.

| Loop | Kabat | AbM | Chothia |
|---|---|---|---|
| L1 | L24-L34 | L24-L34 | L24-L34 |
| L2 | L50-L56 | L50-L56 | L50-L56 |
| L3 | L89-L97 | L89-L97 | L89-L97 |
| H1 | H31-H35B | H26-H35B | H26-H32 ... 34 |
| | | (Kabat Numbering) | |
| H1 | H31-H35 | H26-H35 | H26-H32 |
| | | (Chothia Numbering) | |
| H2 | H50-H65 | H50-H58 | H52-H56 |
| H3 | H95-H102 | H95-H102 | H95-H102 |

The term "human" antibody or antigen-binding fragment thereof means an antibody or antigen-binding fragment thereof produced by a human or an antibody or antigen-binding fragment thereof having an amino acid sequence corresponding to an antibody or antigen-binding fragment thereof produced by a human made using any technique known in the art. This definition of a human antibody or antigen-binding fragment thereof includes intact or full-length antibodies, fragments thereof.

The term "chimeric" antibodies or antigen-binding fragments thereof refers to antibodies or antigen-binding fragments thereof wherein the amino acid sequence is derived from two or more species. Typically, the variable region of both light and heavy chains corresponds to the variable region of antibodies or antigen-binding fragments thereof derived from one species of mammals (e.g., mouse, rat, rabbit, etc.) with the desired specificity, affinity, and capability while the constant regions are homologous to the sequences in antibodies or antigen-binding fragments thereof derived from another (usually human) to avoid eliciting an immune response in that species.

The term "epitope" or "antigenic determinant" are used interchangeably herein and refer to that portion of an antigen capable of being recognized and specifically bound by a particular antibody or antigen-binding fragment thereof. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following.

"Or better" when used herein to refer to binding affinity refers to a stronger binding between a molecule and its binding partner. "Or better" when used herein refers to a stronger binding, represented by a smaller numerical Kd value. For example, an antibody which has an affinity for an antigen of "0.6 nM or better", the antibody's affinity for the antigen is <0.6 nM, i.e., 0.59 nM, 0.58 nM, 0.57 nM etc. or any value less than 0.6 nM.

The phrase "substantially similar," or "substantially the same", as used herein, denotes a sufficiently high degree of similarity between two numeric values (generally one associated with an antibody of the invention and the other associated with a reference/comparator antibody) such that one of skill in the art would consider the difference between the two values to be of little or no biological and/or statistical significance within the context of the biological characteristics measured by said values (e.g., Kd values). The difference between said two values is less than about 50%, less than about 40%, less than about 30%, less than about 20%, or less than about 10% as a function of the value for the reference/comparator antibody.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cell or compositions include those which have been purified to a degree that they are no longer in a form in which they are found in nature. In some embodiments, an antibody, polynucleotide, vector, cell, or composition which is isolated is substantially pure.

As used herein, "substantially pure" refers to material which is at least 50% pure (i.e., free from contaminants), at least 90% pure, at least 95% pure, at least 98% pure, or at least 99% pure.

The term "immunoconjugate" or "conjugate" as used herein refers to a compound or a derivative thereof that is linked to a cell binding agent (i.e., an anti-CD37 antibody or antigen-binding fragment thereof) and is defined by a generic formula: C-L-A, wherein C=cytotoxin, L=linker, and A=cell binding agent or anti-CD37 antibody or antigen-binding fragment thereof. Immunoconjugates can also be defined by the generic formula in reverse order: A-L-C.

A "linker" is any chemical moiety that is capable of linking a compound, usually a drug, such as a maytansinoid, to a cell-binding agent such as an anti CD37 antibody or a fragment thereof in a stable, covalent manner. Linkers can be susceptible to or be substantially resistant to acid-induced cleavage, light-induced cleavage, peptidase-induced cleavage, esterase induced cleavage, and disulfide bond cleavage, at conditions under which the compound or the antibody remains active. Suitable linkers are well known in the art and include, for example, disulfide groups, thioether groups, acid labile groups, photolabile groups, peptidase labile groups and esterase labile groups. Linkers also include charged linkers, and hydrophilic forms thereof as described herein and know in the art.

The terms "cancer" and "cancerous" refer to or describe the physiological condition in mammals in which a population of cells are characterized by unregulated cell growth.

Examples of cancer include, but are not limited to, carcinoma, lymphoma, blastoma, sarcoma, and leukemia. More particular examples of "cancer" or "tumorigenic" diseases include B-cell lymphomas including NHL, precursor B-cell lymphoblastic leukemia/lymphoma and mature B-cell neoplasms, such as B-cell chronic lymphocytic leukemia (CLL)/small lymphocytic lymphoma (SLL), B-cell prolymphocytic leukemia, lymphoplasmacytic lymphoma, mantle cell lymphoma (MCL), follicular lymphoma (FL), including low-grade, intermediate-grade and high-grade FL, cutaneous follicle center lymphoma, marginal zone B-cell lymphoma (MALT type, nodal and splenic type), hairy cell leukemia, diffuse large B-cell lymphoma (DLBCL), Burkitt's lymphoma (BL), plasmacytoma, plasma cell myeloma, post-transplant lymphoproliferative disorder, and anaplastic large-cell lymphoma (ALCL). In some embodiments, the cancer is a leukemia or lymphoma.

"Tumor" and "neoplasm" refer to any mass that result from excessive cell growth or proliferation, either benign (noncancerous) or malignant (cancerous) including pre-cancerous lesions.

The terms "cancer cell," "tumor cell," and grammatical equivalents refer to the total population of cells derived from a tumor or a pre-cancerous lesion, including both non-tumorigenic cells, which comprise the bulk of the tumor cell population, and tumorigenic stem cells (cancer stem cells). As used herein, the term "tumor cell" will be modified by the term "non-tumorigenic" when referring solely to those tumor cells lacking the capacity to renew and differentiate to distinguish those tumor cells from cancer stem cells.

The term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

A "chemotherapeutic agent" is a chemical compound useful in the treatment of cancer, regardless of mechanism of action. Classes of chemotherapeutic agents include, but are not limited to alkylating agents, antimetabolites, spindle poison plant alkaloids, cytotoxic/antitumor antibiotics, topoisomerase inhibitors, antibodies, photosensitizers, and kinase inhibitors. Chemotherapeutic agents include compounds used in "targeted therapy" and conventional chemotherapy.

Administration "in combination with" one or more further therapeutic agents includes simultaneous (concurrent) and consecutive administration in any order.

The term "pharmaceutical formulation" refers to a preparation which is in such form as to permit the biological activity of the active ingredient to be effective, and which contains no additional components which are unacceptably toxic to a subject to which the formulation would be administered. Such formulation can be sterile.

An "effective amount" of an antibody, antigen-binding fragment thereof, or immunoconjugate as disclosed herein is an amount sufficient to carry out a specifically stated purpose. An "effective amount" can be determined empirically and in a routine manner, in relation to the stated purpose.

The term "therapeutically effective amount" refers to an amount of an antibody, antigen-binding fragment thereof, or other drug effective to "treat" a disease or disorder in a subject or mammal. In the case of cancer, the therapeutically effective amount of the drug can reduce the number of cancer cells; reduce the tumor size; inhibit (i.e., slow to some extent and in a certain embodiment, stop) cancer cell infiltration into peripheral organs; inhibit (i.e., slow to some extent and in a certain embodiment, stop) tumor metastasis; inhibit, to some extent, tumor growth; relieve to some extent one or more of the symptoms associated with the cancer; and/or result in a favorable response such as increased progression-free survival (PFS), disease-free survival (DFS), or overall survival (OS), complete response (CR), partial response (PR), or, in some cases, stable disease (SD), a decrease in progressive disease (PD), a reduced time to progression (TTP), or any combination thereof. See the definition herein of "treating." To the extent the drug can prevent growth and/or kill existing cancer cells, it can be cytostatic and/or cytotoxic. In certain embodiments, identification of increased CD37 levels allows for administration of decreased amounts of the CD37-targeting therapeutic to achieve the same therapeutic effect as seen with higher dosages. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The term "respond favorably" generally refers to causing a beneficial state in a subject. With respect to cancer treatment, the term refers to providing a therapeutic effect on the subject. Positive therapeutic effects in cancer can be measured in a number of ways (See, W. A. Weber, J. Nucl. Med. 50:1S-10S (2009)). For example, tumor growth inhibition, molecular marker expression, serum marker expression, and molecular imaging techniques can all be used to assess therapeutic efficacy of an anti-cancer therapeutic. With respect to tumor growth inhibition, according to NCI standards, a T/C$\leq$42% is the minimum level of anti-tumor activity. A T/C<10% is considered a high anti-tumor activity level, with T/C (%)=Median tumor volume of the treated/Median tumor volume of the control×100. A favorable response can be assessed, for example, by increased progression-free survival (PFS), disease-free survival (DFS), or overall survival (OS), complete response (CR), partial response (PR), or, in some cases, stable disease (SD), a decrease in progressive disease (PD), a reduced time to progression (TTP), or any combination thereof.

PFS, DFS, and OS can be measured by standards set by the National Cancer Institute and the U.S. Food and Drug Administration for the approval of new drugs. See Johnson et al, (2003) J. Clin. Oncol. 21(7):1404-1411.

"Progression free survival" (PFS) refers to the time from enrollment to disease progression or death. For NHL patients, PFS can be measured using the standards provided in the International Harmonization Project's Revised Response Criteria for Malignant Lymphoma (Cheson et al, *J Clin Oncol.* 25:579-86 (2007), which is herein incorporated by reference in its entirety). For CLL patients, PFS can be measured using the standards provided in the National Cancer Institute (NCI) International Workshop on CLL Response Criteria (Hallek et al, *Blood,* 111:5446-56 (2008), which is herein incorporated by reference in its entirety). For Hodgkin's and non-Hodgkin's lymphoma patients, PFS can be measured using the Lugano Classification standards (Cheson et al, *J Clin Oncol.* 32:3059-68 (2014)). Generally, progression free survival refers to the situation wherein a patient remains alive, without the cancer getting worse.

"Time to Tumor Progression" (TTP) is defined as the time from enrollment to disease progression. For NHL patients, TTP can be measured using the standards provided in the International Harmonization Project's Revised Response Criteria for Malignant Lymphoma (Cheson et al, *J Clin*

*Oncol.* 25:579-86 (2007), which is herein incorporated by reference in its entirety). For CLL patients, TTP can be measured using the standards provided in the National Cancer Institute (NCI) International Workshop on CLL Response Criteria (Hallek et al, *Blood,* 111:5446-56 (2008), which is herein incorporated by reference in its entirety). For Hodgkin's and non-Hodgkin's lymphoma patients, TTP can be measured using the Lugano Classification standards (Cheson et al, *J Clin Oncol.* 32:3059-68 (2014)).

A "complete response" or "complete remission" or "CR" indicates the disappearance of all signs of tumor or cancer in response to treatment. This does not always mean the cancer has been cured.

A "partial response" or "PR" refers to a decrease in the size or volume of one or more tumors or lesions, or in the extent of cancer in the body, in response to treatment.

"Stable disease" refers to disease without progression or relapse. In stable disease there is neither sufficient tumor shrinkage to qualify for partial response nor sufficient tumor increase to qualify as progressive disease.

"Progressive disease" refers to the appearance of one more new lesions or tumors and/or the unequivocal progression of existing non-target lesions. Progressive disease can also refer to a tumor growth of more than 20 percent since treatment began, either due to an increases in mass or in spread of the tumor.

"Disease free survival" (DFS) refers to the length of time during and after treatment that the patient remains free of disease.

"Overall Survival" (OS) refers to the time from patient enrollment to death or censored at the date last known alive. OS includes a prolongation in life expectancy as compared to naive or untreated individuals or patients. Overall survival refers to the situation wherein a patient remains alive for a defined period of time, such as one year, five years, etc., e.g., from the time of diagnosis or treatment.

Terms such as "treating" or "treatment" or "to treat" or "alleviating" or "to alleviate" refer to therapeutic measures that cure, slow down, lessen symptoms of, and/or halt progression of a diagnosed pathologic condition or disorder. Thus, those in need of treatment include those already diagnosed with or suspected of having the disorder. In certain embodiments, a subject is successfully "treated" for cancer according to the methods of the present invention if the patient shows one or more of the following: a reduction in the number of or complete absence of cancer cells; a reduction in the tumor size; inhibition of or an absence of cancer cell infiltration into peripheral organs including, for example, the spread of cancer into soft tissue and bone; inhibition of or an absence of tumor metastasis; inhibition or an absence of tumor growth; relief of one or more symptoms associated with the specific cancer; reduced morbidity and mortality; improvement in quality of life; reduction in tumorigenicity, tumorigenic frequency, or tumorigenic capacity, of a tumor; reduction in the number or frequency of cancer stem cells in a tumor; differentiation of tumorigenic cells to a non-tumorigenic state; increased progression-free survival (PFS), disease-free survival (DFS), or overall survival (OS), complete response (CR), partial response (PR), stable disease (SD), a decrease in progressive disease (PD), a reduced time to progression (TTP), or any combination thereof.

Prophylactic or preventative measures refer to therapeutic measures that prevent and/or slow the development of a targeted pathologic condition or disorder. Thus, those in need of prophylactic or preventative measures include those prone to have the disorder and those in whom the disorder is to be prevented.

As used herein, the term "healthcare provider" refers to individuals or institutions which directly interact with and administer to living subjects, e.g., human patients. Non-limiting examples of healthcare providers include doctors, nurses, technicians, therapist, pharmacists, counselors, alternative medicine practitioners, medical facilities, doctor's offices, hospitals, emergency rooms, clinics, urgent care centers, alternative medicine clinics/facilities, and any other entity providing general and/or specialized treatment, assessment, maintenance, therapy, medication, and/or advice relating to all, or any portion of, a patient's state of health, including but not limited to general medical, specialized medical, surgical, and/or any other type of treatment, assessment, maintenance, therapy, medication and/or advice.

In some aspects, a healthcare provider can administer or instruct another healthcare provider to administer a therapy to treat a cancer. "Administration" of a therapy, as used herein, includes prescribing a therapy to a subject as well as delivering, applying, or giving the therapy to a subject. A healthcare provider can implement or instruct another healthcare provider or patient to perform the following actions: obtain a sample, process a sample, submit a sample, receive a sample, transfer a sample, analyze or measure a sample, quantify a sample, provide the results obtained after analyzing/measuring/quantifying a sample, receive the results obtained after analyzing/measuring/quantifying a sample, compare/score the results obtained after analyzing/measuring/quantifying one or more samples, provide the comparison/score from one or more samples, obtain the comparison/score from one or more samples, administer a therapy or therapeutic agent (e.g., a CD37 binding agent), commence the administration of a therapy, cease the administration of a therapy, continue the administration of a therapy, temporarily interrupt the administration of a therapy, increase the amount of an administered therapeutic agent, decrease the amount of an administered therapeutic agent, continue the administration of an amount of a therapeutic agent, increase the frequency of administration of a therapeutic agent, decrease the frequency of administration of a therapeutic agent, maintain the same dosing frequency on a therapeutic agent, replace a therapy or therapeutic agent by at least another therapy or therapeutic agent, combine a therapy or therapeutic agent with at least another therapy or additional therapeutic agent. These actions can be performed by a healthcare provider automatically using a computer-implemented method (e.g., via a web service or stand-alone computer system).

"Polynucleotide" or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide can comprise modified nucleotides, such as methylated nucleotides and their analogs. If present, modification to the nucleotide structure can be imparted before or after assembly of the polymer. The sequence of nucleotides can be interrupted by non-nucleotide components. A polynucleotide can be further modified after polymerization, such as by conjugation with a labeling component. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars can be replaced, for example, by phosphonate groups, phosphate groups, protected by standard protecting groups, or activated to prepare additional linkages to additional nucleotides, or can be conjugated to solid supports. The 5' and 3' terminal OH can be phosphorylated or substituted with amines or organic capping group moieties of from 1 to 20 carbon atoms. Other hydroxyls can also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages can be replaced by alternative linking groups. These alternative linking groups include, but are not limited to, embodiments wherein phosphate is replaced by P(O)S ("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

The term "vector" means a construct, which is capable of delivering, and expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

The terms "polypeptide," "peptide," and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon antibodies, in certain embodiments, the polypeptides can occur as single chains or associated chains. In some embodiments, a polypeptide, peptide, or protein is non-naturally occurring. In some embodiments, a polypeptide, peptide, or protein is purified from other naturally occurring components. In some embodiments, the polypeptide, peptide, or protein is recombinantly produced.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences. One such non-limiting example of a sequence alignment algorithm is the algorithm described in Karlin et al, 1990, *Proc. Natl. Acad. Sci.*, 87:2264-2268, as modified in Karlin et al., 1993, *Proc. Natl. Acad. Sci.*, 90:5873-5877, and incorporated into the NBLAST and XBLAST programs (Altschul et al., 1991, *Nucleic Acids Res.*, 25:3389-3402). In certain embodiments, Gapped BLAST can be used as described in Altschul et al., 1997, *Nucleic Acids Res.* 25:3389-3402. BLAST-2, WU-BLAST-2 (Altschul et al., 1996, *Methods in Enzymology*, 266:460-480), ALIGN, ALIGN-2 (Genentech, South San Francisco, Calif.) or Megalign (DNASTAR) are additional publicly available software programs that can be used to align sequences. In certain embodiments, the percent identity between two nucleotide sequences is determined using the GAP program in GCG software (e.g., using a NWSgapdna.CMP matrix and a gap weight of 40, 50, 60, 70, or 90 and a length weight of 1, 2, 3, 4, 5, or 6). In certain alternative embodiments, the GAP program in the GCG software package, which incorporates the algorithm of Needleman and Wunsch (*J. Mol. Biol.* (48):444-453 (1970)) can be used to determine the percent identity between two amino acid sequences (e.g., using either a Blossum 62 matrix or a PAM250 matrix, and a gap weight of 16, 14, 12, 10, 8, 6, or 4 and a length weight of 1, 2, 3, 4, 5). Alternatively, in certain embodiments, the percent identity between nucleotide or amino acid sequences is determined using the algorithm of Myers and Miller (CABIOS, 4:11-17 (1989)). For example, the percent identity can be determined using the ALIGN program (version 2.0) and using a PAM120 with residue table, a gap length penalty of 12 and a gap penalty of 4. Appropriate parameters for maximal alignment by particular alignment software can be determined by one skilled in the art. In certain embodiments, the default parameters of the alignment software are used. In certain embodiments, the percentage identity "X" of a first amino acid sequence to a second sequence amino acid is calculated as 100×(Y/Z), where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be longer than the percent identity of the second sequence to the first sequence.

As a non-limiting example, whether any particular polynucleotide has a certain percentage sequence identity (e.g., is at least 80% identical, at least 85% identical, at least 90% identical, and in some embodiments, at least 95%, 96%, 97%, 98%, or 99% identical) to a reference sequence can, in certain embodiments, be determined using the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2: 482 489 (1981), to find the best segment of homology between two sequences. When using Bestfit or any other sequence alignment program to determine whether a particular sequence is, for instance, 95% identical to a reference sequence according to the present invention, the parameters are set such that the percentage of identity is calculated over the full length of the reference nucleotide sequence and that gaps in homology of up to 5% of the total number of nucleotides in the reference sequence are allowed.

In some embodiments, two nucleic acids or polypeptides of the invention are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. In certain embodiments, identity exists over a region of the sequences that is at least about 10, about 20, about 40-60 residues in length or any integral value therebetween, or over a longer region than 60-80 residues, at least about 90-100 residues, or the sequences are substantially identical over the full length of the sequences being compared, such as the coding region of a nucleotide sequence for example.

A "conservative amino acid substitution" is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. In certain embodiments, conservative substitutions in the sequences of the polypeptides and antibodies of the invention do not abrogate the binding of the polypeptide or antibody containing the amino acid sequence, to the antigen(s), i.e., the CD37 to which the polypeptide or antibody binds. Methods of identifying nucleotide and amino acid conservative substitutions which do not eliminate antigen-binding are well-known in the art (see, e.g., Brummell et al., *Biochem.* 32: 1180-1187 (1993); Kobayashi et al. *Protein Eng.* 12(10):879-884 (1999); and Burks et al. *Proc. Natl. Acad. Sci. USA* 94:.412-417 (1997)).

As used in the present disclosure and claims, the singular forms "a," "an," and "the" include plural forms unless the context clearly dictates otherwise.

It is understood that wherever embodiments are described herein with the language "comprising," otherwise analogous embodiments described in terms of "consisting of" and/or "consisting essentially of" are also provided.

The term "and/or" as used in a phrase such as "A and/or B" herein is intended to include both "A and B," "A or B," "A," and "B." Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

II. CD37-BINDING AGENTS

The present disclosure provides agents that specifically bind human CD37. These agents are referred to herein as "CD37-binding agents." In certain embodiments, the CD37 binding agents are antibodies, antigen-binding fragments thereof, immunoconjugates, or polypeptides. The full-length amino acid sequences for human CD37 are known in the art and also provided herein as represented by SEQ ID NO:1, respectively.

Human CD37:
(SEQ ID NO: 1)
MSAQESCLSLIKYFLFVFNLFFFVLGSLIFCFGIWILIDKTSFVSFVGLAF

VPLQIWSKVLAISGIFTMGIALLGCVGALKELRCLLGLYFGMLLLLFATQI

TLGILTSTQRAQLERSLRDVVEKTIQKYGTNPEETAAEESWDYVQFQLRCC

GWHYPQDWFQVLILRGNGSEAHRVPCSCYNLSATNDSTILDKVILPQLSRL

GHLARSRHSADICAVPAESHIYREGCAQGLQKWLHNNLISIVGICLGVGLL

ELGFMTLSIFLCRNLDHVYNRLARYR

Human CD37 Nucleic Acid Sequence:
(SEQ ID NO: 2)
atgtcagcccaggagagctgcctcagcctcatcaagtacttctatcgttt tcaacctcttcttcttcgtcctcggcagcctgatcttctgcttcggcatct ggatcctcattgacaagaccagcttcgtgtcctttgtgggcttggccttcg tgcctctgcagatctggtccaaagtcctggccatctcaggaatcttcacca tgggcatcgccctectgggttgtgtggggccctcaaggagctccgctgcc tcctgggcctgtattttgggatgctgctgctcctgtttgccacacagatca ccctgggaatcctcatctccactcagcgggcccagctggagcgaagcttgc gggacgtcgtagagaaaaccatccaaaagtacggcaccaacccgaggaga ccgcggccgaggagagctgggactatgtgcagttccagctgcgctgctgcg gctggcactacccgcaggactggttccaagtcctcatcctgagaggtaacg ggtcggaggcgcaccgcgtgccctgctcctgctacaacttgtcggcgacca acgactccacaatcctagataaggtgatcttgcccagctcagcaggcttg gacacctggcgcggtccagacacagtgcagacatctgcgctgtccctgcag agagccacatctaccgcgagggctgcgcgcagggcctccagaagtggctgc acaacaaccttatttccatagtgggcatttgcctgggcgtcggcctactcg agctcgggttcatgacgctctcgatattcctgtgcagaaacctggaccacg tctacaaccggctcgctcgataccgt Thus, in some embodiments, the CD37 binding agents can specifically bind to an epitope of SEQ ID NO:1 or to an epitope of the polypeptide encoded by SEQ ID NO:2.

CD37-binding agents also include CD37-binding agents with sequences of the 1B11-2 antibody provided below.

muCD37-1B11-2 VH-CDR1
(SEQ ID NO: 3)
GYFMN muCD37-1B11-2 VH-CDR2 (Kabat)
(SEQ ID NO: 4)
RINPYNGDTFYNQKFKG muCD37-1B11-2 VH-CDR2 (AbM)
(SEQ ID NO: 34)
RINPYNGDTF muCD37-1B11-2 VH-CDR3
(SEQ ID NO: 5)
RGIVASSRFFDV muCD37-1B11-2 VL-CDR1
(SEQ ID NO: 6)
KASQGVSNDVD muCD37-1B11-2 VL-CDR2
(SEQ ID NO: 7)
YASNRYT muCD37-1B11-2 VL-CDR3
(SEQ ID NO: 8)
CHQDYTSPT muCD37-1B11-2 heavy chain variable region (VH)
(SEQ ID NO: 9)
EVQLLQSGPELVKPGASVKISCKASGYSFTGYFMNWVIQSHGKGLEWIGR
INPYNGDTFYNQKFKGKATLTVDKSSTTAHMELLSLTSEDSAVYYCGSRG
IVASSRFEDVWGAGTSVIVSS muCD37-1B11-2 light chain variable region (VL)
(SEQ ID NO: 10)
SIVMTQTPKELLVSAGDRVTITCKASQGVSNDVDWYQQKPGQSPKLLIYY
ASNRYTGVPDRFTGSGYGTDFTFSISTVQAEDLAVYFCHQDYTSPTFGGG
TKLEIKR muCD37-1B11-2 full length heavy chain (HC)
(SEQ ID NO: 11)
EVQLLQSGPELVKPGASVKISCKASGYSFTGYFMNWVIQSHGKGLEWIGR

INPYNGDTFYNQKFKGKATLTVDKSSTTAHMELLSLTSEDSAVYYCGSRG

IVASSRFEDVWGAGTSVIVSSAKTTPPSVYPLAPGSAAQTNSMVTLGCLV

KGYFPEPVTVTWNSGSLSSGVHTFPAVLESDLYTLSSSVTVPSSPRPSET

VTCNVAHPASSTKVDKKIVPRDCGCKPCICTVPEVSSVFIFPPKPKDVLT

ITLTPKVTCVVVDISKDDPEVQFSWFVDDEVHTAQTQPREEQFNSTFRSV

SELPIMHQDWLNGKEEKCRVNSAAFPAPIEKTISKTKGRPKAPQVYTIPP

PKEQMAKDKVSLTCMITDFFPEDITVEWQWNGQPAENYKNTQPIMNTNGS

YFVYSKLNVQKSNWEAGNTFTCSVLHEGLHNHHTEKSLSHSPGK muCD37-1B11-2 full length light chain
(SEQ ID NO: 12)
SIVMTQTPKELLVSAGDRVTITCKASQGVSNDVDWYQQKPGQSPKLLIYY

ASNRYTGVPDRFTGSGYGTDFTFSISTVQAEDLAVYFCHQDYTSPTFGGG

TKLEIKRADAAPTVSIFPPSSEQLTSGGASVVCFLNNEYPKDINVKWKID

GSERQNGVLNSWTDQDSKDSTYSMSSTLTLTKDEYERHNSYTCEATHKTS

TSPIVKSFNRNEC

CD37-binding agents include CD37-binding agents (e.g., antibodies and antigen-binding fragments thereof) that comprise the six CDR sequences of the 1B11-2 antibody provided in SEQ ID NOs:3-8.

The CD37-binding molecules can be CD37-binding agents (e.g., antibodies and antigen-binding fragments thereof) that comprise the CDRs of antibody 1B11-2 (i.e., SEQ ID NOs: 3-8), with up to four (i.e., 0, 1, 2, 3, or 4) conservative amino acid substitutions per CDR. The CD37-binding molecules can be CD37-binding agents (e.g., antibodies and antigen-binding fragments thereof) that comprise the CDRs of antibody 1B11-2 (i.e., SEQ ID NOs: 3-8), with up to four (i.e., 0, 1, 2, 3, or 4) conservative amino acid substitutions. The CD37-binding molecules can be CD37-binding agents (e.g., antibodies and antigen-binding fragments thereof) that comprise (i) the CDRs of SEQ ID NOs: 3, 4, 6, and 7, with up to four (i.e., 0, 1, 2, 3, or 4) conservative amino acid substitutions per CDR and (ii) the CDRs of SEQ ID NOs: 5 and 8. The CD37-binding molecules can be CD37-binding agents (e.g., antibodies and antigen-binding fragments thereof) that comprise (i) the CDRs of SEQ ID NOs: 3, 4, 6, and 7, with up to four (i.e., 0, 1, 2, 3, or 4) conservative amino acid substitutions and (ii) the CDRs of SEQ ID NOs: 5 and 8. The CD37-binding molecules can be CD37-binding agents (e.g., antibodies and antigen-binding fragments thereof) that comprise (i) the CDRs of SEQ ID NOs: 3, 4, and 6-8, with up to four (i.e., 0, 1, 2, 3, or 4) conservative amino acid substitutions per CDR and (ii) the CDR of SEQ ID NO:5. The CD37-binding molecules can be CD37-binding agents (e.g., antibodies and antigen-binding fragments thereof) that comprise (i) the CDRs of SEQ ID NOs: 3, 4, and 6-8, with up to four (i.e., 0, 1, 2, 3, or 4) conservative amino acid substitutions and (ii) the CDR of SEQ ID NO:5.

Polypeptides, antibodies, and antigen-binding fragments thereof can comprise the variable light chain, the variable heavy chain, or both the variable light and variable heavy chains of the 1B11-2 antibody. Also provided are polypeptides that comprise (a) a polypeptide having at least 90% sequence identity to SEQ ID NO:9 and/or (b) a polypeptide having at least 90% sequence identity to SEQ ID NO:10. In certain embodiments, the polypeptide is an antibody and/or the polypeptide specifically binds CD37. In certain embodiments, the polypeptide is a murine, chimeric, or humanized antibody that specifically binds CD37. In certain embodiments, the polypeptide having a certain percentage of sequence identity to SEQ ID NO:9 or 10 differs from SEQ ID NO:9 or 10 by conservative amino acid substitutions only.

In certain embodiments, a polypeptide, antibody, or antigen-binding fragment thereof comprises a variable heavy chain domain comprising a sequence at least 95% identical to SEQ ID NO:9. In certain embodiments, a polypeptide, antibody, or antigen-binding fragment thereof comprises a variable heavy chain domain comprising a sequence at least 96% identical to SEQ ID NO:9. In certain embodiments, a polypeptide, antibody, or antigen-binding fragment thereof comprises a variable heavy chain domain comprising a sequence at least 97% identical to SEQ ID NO:9. In certain embodiments, a polypeptide, antibody, or antigen-binding fragment thereof comprises a variable heavy chain domain comprising a sequence at least 98% identical to SEQ ID NO:9. In certain embodiments, a polypeptide, antibody, or antigen-binding fragment thereof comprises a variable heavy chain domain comprising a sequence at least 99% identical to SEQ ID NO:9. In certain embodiments, the polypeptide is an antibody and/or the polypeptide specifically binds CD37. In certain embodiments, the polypeptide is a murine, chimeric, or humanized antibody that specifically binds CD37. In certain embodiments, the polypeptide having a certain percentage of sequence identity to SEQ ID NO:9 differs from SEQ ID NO:9 by conservative amino acid substitutions only. In certain embodiments, the polypeptide having a certain percentage of sequence identity to SEQ ID NO:9 differs from SEQ ID NO:9 only in amino acids outside of the CDRs. In certain embodiments, the polypeptide having a certain percentage of sequence identity to SEQ ID NO:9 differs from SEQ ID NO:9 only by conservative amino acid substitutions outside of the CDRs.

In certain embodiments, a polypeptide, antibody, or antigen-binding fragment thereof comprises a variable light chain domain comprising a sequence at least 95% identical to SEQ ID NO:10. In certain embodiments, a polypeptide, antibody, or antigen-binding fragment thereof comprises a variable light chain domain comprising a sequence at least 96% identical to SEQ ID NO: 10. In certain embodiments, a polypeptide, antibody, or antigen-binding fragment thereof comprises a variable light chain domain comprising a sequence at least 97% identical to SEQ ID NO: 10. In certain embodiments, a polypeptide, antibody, or antigen-binding fragment thereof comprises a variable light chain domain comprising a sequence at least 98% identical to SEQ ID NO: 10. In certain embodiments, a polypeptide, antibody, or antigen-binding fragment thereof comprises a variable light chain domain comprising a sequence at least 99% identical to SEQ ID NO: 10. In certain embodiments, the polypeptide is an antibody and/or the polypeptide specifically binds CD37. In certain embodiments, the polypeptide is a murine, chimeric, or humanized antibody that specifically binds CD37. In certain embodiments, the polypeptide having a certain percentage of sequence identity to SEQ ID NO:10 differs from SEQ ID NO:10 by conservative amino acid substitutions only. In certain embodiments, the polypeptide having a certain percentage of sequence identity to SEQ ID NO:10 differs from SEQ ID NO:10 only in amino acids outside of the CDRs. In certain embodiments, the polypeptide having a certain percentage of sequence identity to SEQ ID NO:10 differs from SEQ ID NO:10 only by conservative amino acid substitutions outside of the CDRs.

In certain embodiments, a polypeptide, antibody, or antigen-binding fragment thereof comprises a variable heavy chain domain comprising a sequence at least 95% identical to SEQ ID NO:9 and a variable light chain domain comprising a sequence at least 95% identical to SEQ ID NO:10. In certain embodiments, a polypeptide, antibody, or antigen-binding fragment thereof comprises a variable heavy chain domain comprising a sequence at least 96% identical to SEQ ID NO:9 and a variable light chain domain comprising a sequence at least 96% identical to SEQ ID NO:10. In certain embodiments, a polypeptide, antibody, or antigen-binding fragment thereof comprises a variable heavy chain domain comprising a sequence at least 97% identical to SEQ ID NO:9 and a variable light chain domain comprising a sequence at least 97% identical to SEQ ID NO:10. In certain embodiments, a polypeptide, antibody, or antigen-binding fragment thereof comprises a variable heavy chain domain comprising a sequence at least 98% identical to SEQ ID NO:9 and a variable light chain domain comprising a sequence at least 98% identical to SEQ ID NO:10. In certain embodiments, a polypeptide, antibody, or antigen-binding fragment thereof comprises a variable heavy chain domain comprising a sequence at least 99% identical to SEQ ID NO:9 and a variable light chain domain comprising a sequence at least 99% identical to SEQ ID NO:10. In certain embodiments, the polypeptide is an antibody and/or the polypeptide specifically binds CD37. In certain embodiments, the polypeptide is a murine, chimeric, or humanized antibody that specifically binds CD37. In certain embodiments, the polypeptide having a certain percentage of sequence identity to SEQ ID NO:9 and/or 10 differs from SEQ ID SEQ ID NO:9 and/or 10 by conservative amino acid substitutions only. In certain embodiments, the polypeptide having a certain percentage of sequence identity to SEQ ID NO:9 and/or 10 differs from SEQ ID NO:9 and/or 10 only in amino acids outside of the CDRs. In certain embodiments, the polypeptide having a certain percentage of sequence identity to SEQ ID NO:9 and/or 10 differs from SEQ ID NO:9 and/or 10 only by conservative amino acid substitutions outside of the CDRs.

In certain embodiments, a polypeptide, antibody, or antigen-binding fragment thereof comprises a variable heavy chain domain comprising the sequence set forth in SEQ ID NO:9 and a variable light chain domain comprising the sequence set forth in SEQ ID NO:10.

Polypeptides can comprise one of the individual light chains or heavy chains described herein. Antibodies and polypeptides can also comprise both a light chain and a heavy chain. The light chain and heavy chain sequences of antibody 1B11-2 are provided in SEQ ID NOs:11 and 12.

Also provided are polypeptides that comprise: (a) a polypeptide having at least about 90% sequence identity to SEQ ID NO:11; and/or (b) a polypeptide having at least about 90% sequence identity to SEQ ID NO:12. In certain embodiments, the polypeptide comprises a polypeptide having at least about 95%, at least about 96%, at least about 97%, at least about 98%, or at least about 99% sequence identity to SEQ ID NO:11 or 12. Thus, in certain embodiments, the polypeptide comprises (a) a polypeptide having at least about 95% sequence identity to SEQ ID NO:11, and/or (b) a polypeptide having at least about 95% sequence identity to SEQ ID NO:12. In certain embodiments, the polypeptide comprises (a) a polypeptide having the amino acid sequence of SEQ ID NO:11; and/or (b) a polypeptide having the amino acid sequence of SEQ ID NO:12. In certain embodiments, the polypeptide is an antibody and/or the polypeptide specifically binds CD37. In certain embodiments, the polypeptide is a murine, chimeric, or humanized antibody that specifically binds CD37. In certain embodiments, the polypeptide having a certain percentage of sequence identity to SEQ ID NO:11 and/or 12 differs from SEQ ID NO:11 and/or 12 by conservative amino acid substitutions only. In certain embodiments, the polypeptide having a certain percentage of sequence identity to SEQ ID NO:11 and/or 12 differs from SEQ ID NO:11 and/or 12 only in amino acids outside of the CDRs. In certain embodiments, the polypeptide having a certain percentage of sequence identity to SEQ ID NO:11 and/or 12 differs from SEQ ID NO:11 and/or 12 only by conservative amino acid substitutions outside of the CDRs.

In certain embodiments, a CD37-binding agent (e.g., an antibody or antigen-binding fragment thereof) binds to the same epitope as an antibody or antigen-binding fragment thereof comprising a variable heavy chain comprising the sequence set forth in SEQ ID NO:9 and a variable light chain comprising the sequence set forth in SEQ ID NO:10. In certain embodiments, a CD37-binding agent (e.g., an antibody or antigen-binding fragment thereof) competitively inhibits the binding of an antibody or antigen-binding fragment thereof comprising a variable heavy chain comprising the sequence set forth in SEQ ID NO:9 and a variable light chain comprising the sequence set forth in SEQ ID NO:10 to CD37. In certain embodiments, a CD37-binding agent (e.g., an antibody or antigen-binding fragment thereof) competitively inhibits the binding of an antibody or antigen-binding fragment thereof comprising a variable heavy chain comprising the sequence set forth in SEQ ID NO:9 and a variable light chain comprising the sequence set forth in SEQ ID NO:10 to CD37 and binds to an epitope that overlaps with the epitope to which an antibody or antigen-binding fragment thereof comprising a variable heavy chain comprising the sequence set forth in SEQ ID NO:9 and a variable light chain comprising the sequence set forth in SEQ ID NO:10 binds.

In certain embodiments, a CD37-binding agent (e.g., an antibody or antigen-binding fragment thereof) binds to and/or does not bind to the CD37 antigen sequences below as provided herein.

CD37 Antigen Sequences hCD37-LEL (CD37 AA 107-242 underlined)
(SEQ ID NO: 15)
TMELLISTQRAQLERSLRDVVEKTIQKYGTNPEETAAEESWDYVQFQLRC

CGWHYPQDWFQVLILRGNGSEAHRVPCSCYNLSATNDSTILDKVILPQLS

RLGHLARSRHSADICAVPAESHIYREGCAQGLQKWLHNNLSFLEQKLISE

EDLNSAVDHHHHHH hCD37-ECD-Fc (hCD37 AA 107-235 underlined)
(SEQ ID NO: 16)
GPEFLISTQRAQLERSLRDVVEKTIQKYGTNPEETAAEESWDYVQFQLRC

CGWHYPQDWFQVLILRGNGSEAHRVPCSCYNLSATNDSTILDKVILPQLS

RLGHLARSRHSADICAVPAESHIYREGCAQGLQGSEPRGPTIKPCPPCKC

PAPNLLGGPSVFIFPPKIKDVLMISLSPIVTCVVVDSEDDPDVQISWFV

NNVEVHTAQTQTHREDYNSTLRVVSALPIQHQDWMSGKEFKCKVNNKDLP

APIERTISKPKGSVRAPQVYVLPPPEEEMTKKQVTLTCMVTDFMPEDIYV

EWTNNGKTELNYKNTEPVLDSDGSYFMYSKLRVEKKNWVERNSYSCSVVH

EGLHNHHTTKSFSRTPGK hCD37-Fc-LAGA (hCD37 AA 107-235 underlined)
(SEQ ID NO: 17)
GPEFLISTQRAQLERSLRDVVEKTIQKYGTNPEETAAEESWDYVQFQLRC

CGWHYPQDWFQVLILRGNGSEAHRVPCSCYNLSATNDSTILDKVILPQLS

RLGHLARSRHSADICAVPAESHIYREGCAQGLQGSDKTHTCPPCPAPELA

GAPSVFLFPPKPKDTLMISRTPEVTCVVVDVSHEDPEVKFNWYVDGVEVH

NAKTKPREEQYNSTYRVVSVLTVLHQDWLNGKEYKCKVSNKALPAPIEKT

ISKAKGQPREPQVYTLPPSRDELTKNQVSLTCLVKGFYPSDIAVEWESNG

QPENNYKTTPPVLDSDGSFFLYSKLTVDKSRWQQGNVFSCSVMHEALHNH

YTQKSLSLSPG hCD37-ECD-52-Fc (hCD37 AA 107-109 double-underlined and AA 138-235 underlined)
(SEQ ID NO: 18)
GPEFLISAAEESWDYVQFQLRCCGWHYPQDWFQVLILRGNGSEAHRVPCSC

YNLSATNDSTILDKVILPQLSRLGHLARSRHSADICAVPAESHIYREGCA

QGLQGSEPRGPTIKPCPPCKCPAPNLLGGPSVFIFPPKIKDVLMISLSPI

VTCVVVDSEDDPDVQISWFVNNVEVHTAQTQTHREDYNSTLRVVSALPI

QHQDWMSGKEFKCKVNNKDLPAPIERTISKPKGSVRAPQVYVLPPPEEEM

TKKQVTLTCMVTDFMPEDIYVEWTNNGKTELNYKNTEPVLDSDGSYFMYS

KLRVEKKNWVERNSYSCSVVHEGLHNHHTTKSFSRTPGK hCD37 (AA 107-235)
(SEQ ID NO: 19)
LISTQRAQLERSLRDVVEKTIQKYGTNPEETAAEESWDYVQFQLRCCGWH
YPQDWFQVLILRGNGSEAHRVPCSCYNLSATNDSTILDKVILPQLSRLGH
LARSRHSADICAVPAESHIYREGCAQGLQ hCD37 (AA 107-242)
(SEQ ID NO: 20)
LISTQRAQLERSLRDVVEKTIQKYGTNPEETAAEESWDYVQFQLRCCGWH
YPQDWFQVLILRGNGSEAHRVPCSCYNLSATNDSTILDKVILPQLSRLGH
LARSRHSADICAVPAESHIYREGCAQGLQKWLHNNL hCD37 (AA 107-109 and 138-235)
(SEQ ID NO: 21)
LISAAEESWDYVQFQLRCCGWHYPQDWFQVLILRGNGSEAHRVPCSCYNL
SATNDSTILDKVILPQLSRLGHLARSRHSADICAVPAESHIYREGCAQGL
Q In some embodiments, the CD37 binding agent (e.g., an antibody or antigen-binding fragment thereof) binds to amino acids 107-242 of CD37 (SEQ ID NO:20). In some embodiments, the CD37 binding agent (e.g., an antibody or antigen-binding fragment thereof) binds to amino acids 107-235 of CD37 (SEQ ID NO:19).

In some embodiments, the CD37 binding agent (e.g., an antibody or antigen-binding fragment thereof) binds to the sequence set forth in SEQ ID NO:15. In some embodiments, the CD37 binding agent (e.g., an antibody or antigen-binding fragment thereof) binds to the sequence set forth in SEQ ID NO:16. In some embodiments, the CD37 binding agent (e.g., an antibody or antigen-binding fragment thereof) binds to the sequence set forth in SEQ ID NO:17.

In some embodiments, the CD37 binding agent (e.g., an antibody or antigen-binding fragment thereof) binds to amino acids 107-242 of CD37 (SEQ ID NO:20) but does not bind to amino acids 138-235 of CD37. In some embodiments, the CD37 binding agent (e.g., an antibody or antigen-binding fragment thereof) binds to amino acids 107-235 of CD37 (SEQ ID NO:19) but does not bind to amino acids 138-235 of CD37.

In some embodiments, the CD37-binding agent (e.g., an antibody or antigen-binding fragment thereof) binds to a polypeptide of SEQ ID NO:15, but does not bind to a polypeptide of SEQ ID NO:18. In some embodiments, the CD37-binding agent (e.g., an antibody or antigen-binding fragment thereof) binds to a polypeptide of SEQ ID NO:16, but does not bind to a polypeptide of SEQ ID NO:18. In some embodiments, the CD37-binding agent (e.g., an antibody or antigen-binding fragment thereof) binds to a polypeptide of SEQ ID NO:17, but does not bind to a polypeptide of SEQ ID NO:18.

In some embodiments, the CD37 binding agent (e.g., an antibody or antigen-binding fragment thereof) binds to an epitope that includes at least one amino acid in 110-137 of SEQ ID NO:1. Amino acids 110-137 are the first segment ("S1") of the CD37 large extracellular domain.

The affinity or avidity of an antibody for an antigen can be determined experimentally using any suitable method well known in the art, e.g., flow cytometry, enzyme-linked immunoabsorbent assay (ELISA), or radioimmunoassay (RIA), or kinetics (e.g., BIACORE™ analysis). Direct binding assays as well as competitive binding assay formats can be readily employed. (See, for example, Berzofsky, et al., "Antibody-Antigen Interactions," In Fundamental Immunology, Paul, W. E., Ed., Raven Press: New York, N.Y. (1984); Kuby, Janis Immunology, W.H. Freeman and Company: New York, N.Y. (1992); and methods described herein. The measured affinity of a particular antibody-antigen interaction can vary if measured under different conditions (e.g., salt concentration, pH, temperature). Thus, measurements of affinity and other antigen-binding parameters (e.g., KD or Kd, $K_{on}$, $K_{off}$) are made with standardized solutions of antibody and antigen, and a standardized buffer, as known in the art and such as the buffer described herein.

In one aspect, binding assays can be performed using flow cytometry on cells expressing the CD37 antigen on the surface. For example, CD37-positive cells such as 300-19 cells can be incubated with varying concentrations of anti- CD37 antibodies using 1×10⁵ cells per sample in 100 μL FACS buffer (RPMI-1640 medium supplemented with 2% normal goat serum).

Then, the cells can be pelleted, washed, and incubated for 1 h with 100 μL of FITC-conjugated goat-anti-mouse or goat-anti-human IgG-antibody (such as is obtainable from, for example Jackson Laboratory, 6 μg/mL in FACS buffer). The cells are then pelleted again, washed with FACS buffer and resuspended in 200 μL of PBS containing 1% formaldehyde. Samples can be acquired, for example, using a FACS Calibur flow cytometer with the HTS multiwell sampler and analyzed using CellQuest Pro (all from BD Biosciences, San Diego, US). For each sample the mean fluorescence intensity for FL1 (MFI) can be exported and plotted against the antibody concentration in a semi-log plot to generate a binding curve. A sigmoidal dose-response curve is fitted for binding curves and EC50 values are calculated using programs such as GraphPad Prism v4 with default parameters (GraphPad software, San Diego, Calif.). EC50 values can be used as a measure for the apparent dissociation constant "$K_d$" or "$K_D$" for each antibody.

Monoclonal antibodies can be prepared using hybridoma methods, such as those described by Kohler and Milstein (1975) Nature 256:495. Using the hybridoma method, a mouse, hamster, or other appropriate host animal, is immunized to elicit the production by lymphocytes of antibodies that will specifically bind to an immunizing antigen. Lymphocytes can also be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by, e.g., immunoprecipitation, immunoblotting, or by an in vitro binding assay (e.g., radioimmunoassay (RIA); enzyme-linked immunosorbent assay (ELISA)) can then be propagated in either in vitro culture using standard methods (Goding, Monoclonal Antibodies: Principles and Practice, Academic Press, 1986) or in vivo as ascites tumors in an animal. The monoclonal antibodies can then be purified from the culture medium or ascites fluid.

Alternatively, monoclonal antibodies can also be made using recombinant DNA methods as described in U.S. Pat. No. 4,816,567. The polynucleotides encoding a monoclonal antibody are isolated from mature B-cells or hybridoma cells, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which are transfected into host cells such as E. coli cells, simian COS cells, Chinese hamster ovary (CHO) cells, or myeloma cells that do not otherwise produce immunoglobulin protein, and monoclonal antibodies are generated by the host cells. Also, recombinant monoclonal antibodies or fragments thereof of the desired species can be isolated from phage display libraries expressing CDRs of the desired species as described (Mc-Cafferty et al., 1990, Nature, 348:552-554; Clackson et al., 1991, Nature, 352:624-628; and Marks et al., 1991, J. Mol. Biol., 222:581-597).

The polynucleotide(s) encoding a monoclonal antibody can further be modified in a number of different manners using recombinant DNA technology to generate alternative antibodies. In some embodiments, the constant domains of the light and heavy chains of, for example, a mouse monoclonal antibody can be substituted 1) for those regions of, for example, a human antibody to generate a chimeric antibody or 2) for a non-immunoglobulin polypeptide to generate a fusion antibody. In some embodiments, the constant regions are truncated or removed to generate the desired antibody fragment of a monoclonal antibody. Site-directed or high-density mutagenesis of the variable region can be used to optimize specificity, affinity, etc. of a monoclonal antibody.

In some embodiments, the monoclonal antibody against the human CD37 is a humanized antibody. In certain embodiments, the humanized antibody is a resurfaced antibody.

Human antibodies can be directly prepared using various techniques known in the art. Immortalized human B lymphocytes immunized in vitro or isolated from an immunized individual that produce an antibody directed against a target antigen can be generated (See, e.g., Cole et al., Monoclonal Antibodies and Cancer Therapy, Alan R. Liss, p. 77 (1985); Boemer et al., 1991, J. Immunol., 147 (1):86-95; and U.S. Pat. No. 5,750,373). Also, the human antibody can be selected from a phage library, where that phage library expresses human antibodies, as described, for example, in Vaughan et al., 1996, Nat. Biotech., 14:309-314, Sheets et al., 1998, Proc. Nat'l. Acad. Sci., 95:6157-6162, Hoogenboom and Winter, 1991, J. Mol. Biol., 227:381, and Marks et al., 1991, J. Mol. Biol., 222:581). Techniques for the generation and use of antibody phage libraries are also described in U.S. Pat. Nos. 5,969,108, 6,172,197, 5,885,793, 6,521,404; 6,544,731; 6,555,313; 6,582,915; 6,593,081; 6,300,064; 6,653,068; 6,706,484; and 7,264,963; and Rothe et al., 2007, J. Mol. Bio., doi:10.1016/j.jmb.2007.12.018 (each of which is incorporated by reference in its entirety). Affinity maturation strategies and chain shuffling strategies (Marks et al., 1992, Bio/Technology 10:779-783, incorporated by reference in its entirety) are known in the art and can be employed to generate high affinity human antibodies.

Humanized antibodies can also be made in transgenic mice containing human immunoglobulin loci that are capable upon immunization of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016.

In certain embodiments are provided an antibody fragment to, for example, increase tumor penetration. Various techniques are known for the production of antibody fragments. Traditionally, these fragments are derived via proteolytic digestion of intact antibodies (for example Morimoto et al., 1993, Journal of Biochemical and Biophysical Methods 24:107-117; Brennan et al., 1985, Science, 229:81). In certain embodiments, antibody fragments are produced recombinantly. Fab, Fv, and scFv antibody fragments can all be expressed in and secreted from E. coli or other host cells, thus allowing the production of large amounts of these fragments. Such antibody fragments can also be isolated from the antibody phage libraries discussed above. The antibody fragment can also be linear antibodies as described in U.S. Pat. No. 5,641,870, for example, and can be monospecific or bispecific. Other techniques for the production of antibody fragments will be apparent to the skilled practitioner.

According to the present invention, techniques can be adapted for the production of single-chain antibodies specific to CD37 (see U.S. Pat. No. 4,946,778). In addition, methods can be adapted for the construction of Fab expression libraries (Huse, et al., Science 246:1275-1281 (1989)) to allow rapid and effective identification of monoclonal Fab fragments with the desired specificity for CD37, or derivatives, fragments, analogs or homologs thereof. Antibody fragments can be produced by techniques in the art including, but not limited to: (a) a F(ab')2 fragment produced by pepsin digestion of an antibody molecule; (b) a Fab fragment generated by reducing the disulfide bridges of an F(ab')2 fragment, (c) a Fab fragment generated by the treatment of the antibody molecule with papain and a reducing agent, and (d) Fv fragments.

For the purposes of the present disclosure, it should be appreciated that modified antibodies can comprise any type of variable region that provides for the association of the antibody with the polypeptides of a human CD37. In this regard, the variable region can comprise or be derived from any type of mammal. As such, the variable region of the modified antibodies can be, for example, of human, murine, non-human primate (e.g. cynomolgus monkeys, macaques, etc.), or lupine origin. In some embodiments both the variable and constant regions of the modified immunoglobulins are human. In other embodiments the variable regions of compatible antibodies (usually derived from a non-human source) can be engineered or specifically tailored to improve the binding properties of the molecule. In this respect, variable regions useful in the present invention can be humanized or otherwise altered through the inclusion of imported amino acid sequences. In some embodiments, the variable regions of the modified antibodies can be non-human (e.g., murine) and the constant regions of the modified antibodies can be human.

In certain embodiments, the variable domains in both the heavy and light chains are altered by at least partial replacement of one or more CDRs and, if necessary, by partial framework region replacement and sequence changing. Although the CDRs can be derived from an antibody of the same class or even subclass as the antibody from which the framework regions are derived, it is envisaged that the CDRs will be derived from an antibody of different class and possibly from an antibody from a different species. It is not always necessary to replace all of the CDRs with the complete CDRs from the donor variable region to transfer the antigen binding capacity of one variable domain to another. Rather, in some cases it is only necessary to transfer those residues that are necessary to maintain the activity of the antigen binding site.

Alterations to the variable region notwithstanding, those skilled in the art will appreciate that the modified antibodies of this invention will comprise antibodies (e.g., full-length antibodies or immunoreactive fragments thereof) in which at least a fraction of one or more of the constant region domains has been deleted or otherwise altered so as to provide desired biochemical characteristics. In some embodiments, the constant region of the modified antibodies will comprise a human constant region. Modifications to the constant region can comprise additions, deletions or substitutions of one or more amino acids in one or more domains. That is, the modified antibodies disclosed herein can comprise alterations or modifications to one or more of the three heavy chain constant domains (CH1, CH2, or CH3) and/or to the light chain constant domain (CL). In some embodiments, modified constant regions wherein one or more domains are partially or entirely deleted are contemplated. In some embodiments, the modified antibodies will comprise domain deleted constructs or variants wherein the entire CH2 domain has been removed (ΔCH2 constructs). In some embodiments, the omitted constant region domain will be replaced by a short amino acid spacer (e.g. 10 residues) that provides some of the molecular flexibility typically imparted by the absent constant region.

In certain embodiments, modifications of the constant region can be used to eliminate disulfide linkages or oligosaccharide moieties that allow for enhanced localization due to increased antigen specificity or antibody flexibility. Modifications to the constant region can easily be made using well known biochemical or molecular engineering techniques well within the purview of the skilled artisan.

It will be noted that in certain embodiments, the modified antibodies can be engineered to fuse the CH3 domain directly to the hinge region of the respective modified antibodies. In other constructs it can be desirable to provide a peptide spacer between the hinge region and the modified CH2 and/or CH3 domains. For example, compatible constructs could be expressed wherein the CH2 domain has been deleted and the remaining CH3 domain (modified or unmodified) is joined to the hinge region with a 5-20 amino acid spacer. Such a spacer can be added, for instance, to ensure that the regulatory elements of the constant domain remain free and accessible or that the hinge region remains flexible.

The present disclosure further embraces variants and equivalents which are substantially homologous to the mouse, chimeric, humanized and human antibodies, or antibody fragments thereof, set forth herein. These can contain, for example, conservative substitution mutations, i.e. the substitution of one or more amino acids by similar amino acids. For example, conservative substitution refers to the substitution of an amino acid with another within the same general class such as, for example, one acidic amino acid with another acidic amino acid, one basic amino acid with another basic amino acid or one neutral amino acid by another neutral amino acid. What is intended by a conservative amino acid substitution is well known in the art.

The polypeptides of the present disclosure can be recombinant polypeptides, natural polypeptides, or synthetic polypeptides comprising an antibody, or fragment thereof, against a human CD37. It will be recognized in the art that some amino acid sequences of the invention can be varied without significant effect of the structure or function of the protein. Thus, the invention further includes variations of the polypeptides which show substantial activity or which include regions of an antibody, or fragment thereof, against CD37 protein. Such mutants include deletions, insertions, inversions, repeats, and type substitutions.

The isolated polypeptides described herein can be produced by any suitable method known in the art. Such methods range from direct protein synthetic methods to constructing a DNA sequence encoding isolated polypeptide sequences and expressing those sequences in a suitable transformed host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof. See, e.g. Zoeller et al., Proc. Nat'l. Acad. Sci. USA 81:5662-5066 (1984) and U.S. Pat. No. 4,588,585.

In some embodiments a DNA sequence encoding a polypeptide of interest would be constructed by chemical synthesis using an oligonucleotide synthesizer. Such oligonucleotides can be designed based on the amino acid sequence of the desired polypeptide and selecting those codons that are favored in the host cell in which the recombinant polypeptide of interest will be produced. Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis or another method), the polynucleotide sequences encoding a particular isolated polypeptide of interest will be inserted into an expression vector and operatively linked to an expression control sequence appropriate for expression of the protein in a desired host. Proper assembly can be confirmed by nucleotide sequencing, restriction mapping, and expression of a biologically active polypeptide in a suitable host. As is well known in the art, in order to obtain high expression levels of a transfected gene in a host, the gene must be operatively linked to transcriptional and translational expression control sequences that are functional in the chosen expression host.

In certain embodiments, recombinant expression vectors are used to amplify and express DNA encoding antibodies, or fragments thereof, against human CD37. Recombinant expression vectors are replicable DNA constructs which have synthetic or cDNA-derived DNA fragments encoding a polypeptide chain of an anti-CD37 antibody, or fragment thereof, operatively linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail below. Such regulatory elements can include an operator sequence to control transcription. The ability to replicate in a host, usually conferred by an origin of replication, and a selection gene to facilitate recognition of transformants can additionally be incorporated. DNA regions are operatively linked when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. Structural elements intended for use in yeast expression systems include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed recombinant protein to provide a final product.

The choice of expression control sequence and expression vector will depend upon the choice of host. A wide variety of expression host/vector combinations can be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from Esherichia coli, including pCR 1, pBR322, pMB9 and their derivatives, wider host range plasmids, such as M13 and filamentous single-stranded DNA phages.

Suitable host cells for expression of a CD37-binding polypeptide or antibody (or a CD37 protein to use as an antigen) include prokaryotes, yeast, insect or higher eukaryotic cells under the control of appropriate promoters. Prokaryotes include gram negative or gram positive organisms, for example E. coli or bacilli. Higher eukaryotic cells include established cell lines of mammalian origin as described below. Cell-free translation systems could also be employed. Appropriate cloning and expression vectors for use with bacterial, fungal, yeast, and mammalian cellular hosts are described by Pouwels et al. (Cloning Vectors: A Laboratory Manual, Elsevier, N.Y., 1985), the relevant disclosure of which is hereby incorporated by reference. Additional information regarding methods of protein production, including antibody production, can be found, e.g., in U.S. Patent Publication No. 2008/0187954, U.S. Pat. Nos. 6,413,746 and 6,660,501, and International Patent Publication No. WO 04009823, each of which is hereby incorporated by reference herein in its entirety.

Various mammalian or insect cell culture systems are also advantageously employed to express recombinant protein. Expression of recombinant proteins in mammalian cells can be performed because such proteins are generally correctly folded, appropriately modified and completely functional. Examples of suitable mammalian host cell lines include the COS-7 lines of monkey kidney cells, described by Gluzman (Cell 23:175, 1981), and other cell lines capable of expressing an appropriate vector including, for example, L cells, C127, 3T3, Chinese hamster ovary (CHO), HeLa and BHK cell lines. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, Bio/Technology 6:47 (1988).

The proteins produced by a transformed host can be purified according to any suitable method. Such standard methods include chromatography (e.g., ion exchange, affinity and sizing column chromatography), centrifugation, differential solubility, or by any other standard technique for protein purification. Affinity tags such as hexahistidine, maltose binding domain, influenza coat sequence and glutathione-S-transferase can be attached to the protein to allow easy purification by passage over an appropriate affinity column. Isolated proteins can also be physically characterized using such techniques as proteolysis, nuclear magnetic resonance and x-ray crystallography.

For example, supernatants from systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Finally, one or more reversedphase high performance liquid chromatography (RP-HPLC) steps employing hydrophobic RP-HPLC media, e.g., silica gel having pendant methyl or other aliphatic groups, can be employed to further purify a CD37-binding agent. Some or all of the foregoing purification steps, in various combinations, can also be employed to provide a homogeneous recombinant protein.

Recombinant protein produced in bacterial culture can be isolated, for example, by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

Methods known in the art for purifying antibodies and other proteins also include, for example, those described in U.S. Patent Publication Nos. 2008/0312425, 2008/0177048, and 2009/0187005, each of which is hereby incorporated by reference herein in its entirety.

III. POLYNUCLEOTIDES

In certain embodiments, the invention encompasses polynucleotides comprising polynucleotides that encode a polypeptide that specifically binds CD37 or a fragment of such a polypeptide. For example, the invention provides a polynucleotide comprising a nucleic acid sequence that encodes an antibody to a human CD37 or encodes a fragment of such an antibody. The polynucleotides of the invention can be in the form of RNA or in the form of DNA. DNA includes cDNA, genomic DNA, and synthetic DNA; and can be double-stranded or single-stranded, and if single stranded can be the coding strand or non-coding (anti-sense) strand. In some embodiments, the polynucleotide is a cDNA or a DNA lacking one or more endogenous introns.

In certain embodiments, the polynucleotides provided herein are non-naturally occurring. In certain embodiments, the polynucleotides provided herein are recombinantly produced. In certain embodiments, the polynucleotides are isolated. In certain embodiments, the polynucleotides are substantially pure.

The present disclosure provides a polynucleotide encoding a polypeptide comprising a sequence selected from the group consisting of SEQ ID NOs:3-11.

In certain embodiments, a polynucleotide comprises sequences encoding the polypeptides of SEQ ID NOs:3-5. In certain embodiments, a polynucleotide comprises sequences encoding the polypeptides of SEQ ID NOs:6-8. In certain embodiments, a polynucleotide comprises sequences encoding the polypeptides of SEQ ID NOs:3-5 and SEQ ID NOs: 6-8. In certain embodiments, a vector comprises polynucleotides encoding the polypeptides of SEQ ID NOs: 3-8. In certain embodiments, a composition comprises a polynucleotide encoding the polypeptides of SEQ ID NOs:3-5 and a polynucleotide encoding the polypeptides of SEQ ID NOs: 6-8. In certain embodiments, a composition comprises a vector comprising polynucleotides encoding the polypeptides of SEQ ID NOs:3-5 and a vector comprising polynucleotides encoding the polypeptides of SEQ ID NOs:6-8.

In certain embodiments, a composition comprises a polynucleotide encoding the polypeptide of SEQ ID NO:9 and a polynucleotide encoding the polypeptide of SEQ ID NO:10. In certain embodiments, a composition comprises a vector comprising a polynucleotide encoding the polypeptide of SEQ ID NO:9 and a vector comprising a polynucleotide encoding the polypeptide of SEQ ID NO:10. In certain embodiments, a vector comprises a polynucleotide encoding the polypeptide of SEQ ID NO:9 and a polynucleotide encoding the polypeptide of SEQ ID NO:10.

The present disclosure further provides a polynucleotide comprising a sequence selected from those provided in SEQ ID NOs:13 and 14.

muCD37-1B11-2 VH Nucleic Acid Sequence
(SEQ ID NO: 13)
gaggttcaactgctgcagtctggacctgagctggtgaagcctggggcttc agtgaagatatcctgcaaggcttctggttactcatttactggctacttta tgaactgggtgatacagagccatggaaagggccttgagtggattggacgt attaatccttacaatggtgataccttctacaaccagaagttcaagggcaa ggccacattgactgtagacaaatcctctaccacagcccacatggagctcc tgagcctgacatctgaggactctgccgtctattattgtggatcccggggg atagtggcttcctctaggttcttcgatgtctggggcgcagggacctcggt catcgtctcctcagccaaaacgacac muCD37-1B11-2 VL Nucleic Acid Sequence
(SEQ ID NO: 14)
agtattgtgatgacccagactcccaaattectgatgtatcagcaggagac agggttaccataacctgcaaggccagtcagggtgtgagtaatgatgtaga ttggtaccaacagaagccagggcagtctcctaaactgctgatatactatg catccaatcgctacactggagtccctgatcgcttcactggcagtggatat gggacggatttcactttcagcatcagcactgtgcaggctgaagacctggc agtttatttctgtcaccaggattatacctctccgacgttcggtggaggca ccaagctggaaatcaaacgggctgat Also provided is a polynucleotide having at least about 95%, at least about 96%, at least about 97%, at least about 98%, or at least about 99% sequence identity to any one of SEQ ID NOs:13 and 14.

Also provided is a composition comprising a polynucleotide at least about 90% identical to SEQ ID NO:13 and a polynucleotide at least about 90% identical to SEQ ID NO:14. Also provided is a composition comprising a polynucleotide at least about 95% identical to SEQ ID NO:13 and a polynucleotide at least about 95% identical to SEQ ID NO:14. Also provided is a composition comprising a polynucleotide at least about 96% identical to SEQ ID NO:13 and a polynucleotide at least about 96% identical to SEQ ID NO:14. Also provided is a composition comprising a polynucleotide at least about 97% identical to SEQ ID NO:13 and a polynucleotide at least about 97% identical to SEQ ID NO:14. Also provided is a composition comprising a polynucleotide at least about 98% identical to SEQ ID NO:13 and a polynucleotide at least about 98% identical to SEQ ID NO:14. Also provided is a composition comprising a polynucleotide at least about 99% identical to SEQ ID NO:13 and a polynucleotide at least about 99% identical to SEQ ID NO:14.

Also provided is a composition comprising a vector or vectors comprising a polynucleotide at least about 90% identical to SEQ ID NO:13 and a polynucleotide at least about 90% identical to SEQ ID NO:14. Also provided is a composition comprising a vector or vectors a polynucleotide at least about 95% identical to SEQ ID NO:13 and a polynucleotide at least about 95% identical to SEQ ID NO:14. Also provided is a composition comprising a vector or vectors a polynucleotide at least about 96% identical to SEQ ID NO:13 and a polynucleotide at least about 96% identical to SEQ ID NO:14. Also provided is a composition comprising a vector or vectors a polynucleotide at least about 97% identical to SEQ ID NO:13 and a polynucleotide at least about 97% identical to SEQ ID NO:14. Also provided is a composition comprising a vector or vectors a polynucleotide at least about 98% identical to SEQ ID NO:13 and a polynucleotide at least about 98% identical to SEQ ID NO:14. Also provided is a composition comprising a vector or vectors a polynucleotide at least about 99% identical to SEQ ID NO:13 and a polynucleotide at least about 99% identical to SEQ ID NO:14.

Also provided is a composition comprising a vector or vectors comprising the polynucleotide sequence set forth in SEQ ID NO:13 and the polynucleotide sequence set forth in SEQ ID NO:14.

In certain embodiments the polynucleotides comprise the coding sequence for the mature polypeptide fused in the same reading frame to a polynucleotide which aids, for example, in expression and secretion of a polypeptide from a host cell (e.g., a leader sequence which functions as a secretory sequence for controlling transport of a polypeptide from the cell). The polypeptide having a leader sequence is a preprotein and can have the leader sequence cleaved by the host cell to form the mature form of the polypeptide. The polynucleotides can also encode for a proprotein which is the mature protein plus additional 5' amino acid residues. A mature protein having a prosequence is a proprotein and is an inactive form of the protein. Once the prosequence is cleaved an active mature protein remains.

In certain embodiments the polynucleotides comprise the coding sequence for the mature polypeptide fused in the same reading frame to a marker sequence that allows, for example, for purification of the encoded polypeptide. For example, the marker sequence can be a hexa-histidine tag supplied by a pQE-9 vector to provide for purification of the mature polypeptide fused to the marker in the case of a bacterial host, or the marker sequence can be a hemagglutinin (HA) tag derived from the influenza hemagglutinin protein when a mammalian host (e.g., COS-7 cells) is used.

The present disclosure further relates to variants of the hereinabove described polynucleotides encoding, for example, fragments, analogs, and derivatives.

The polynucleotide variants can contain alterations in the coding regions, non-coding regions, or both. In some embodiments the polynucleotide variants contain alterations which produce silent substitutions, additions, or deletions, but do not alter the properties or activities of the encoded polypeptide. In some embodiments, nucleotide variants are produced by silent substitutions due to the degeneracy of the genetic code. Polynucleotide variants can be produced for a variety of reasons, e.g., to optimize codon expression for a particular host (change codons in the human mRNA to those preferred by a bacterial host such as *E. coli*).

Vectors and cells comprising the polynucleotides described herein are also provided.

IV. BIOLOGICAL SAMPLES

Biological samples are often fixed with a fixative. Aldehyde fixatives such as formalin (formaldehyde) and glutaraldehyde are typically used. Tissue samples fixed using other fixation techniques such as alcohol immersion (Battifora and Kopinski, J. Histochem. Cytochem. (1986) 34:1095) are also suitable. The samples used may also be embedded in paraffin. In one embodiment, the samples are both formalin-fixed and paraffin-embedded (FFPE). In another embodiment, the FFPE block is hematoxylin and eosin stained prior to selecting one or more portions for analysis in order to select specific area(s) for the FFPE core sample. Methods of preparing tissue blocks from these particulate specimens have been used in previous IHC studies of various prognostic factors, and/or is well known to those of skill in the art (see, for example, Abbondanzo et al., Am J Clin Pathol. 1990 May; 93(5):698-702; Allred et al., Arch Surg. 1990 January; 125(1):107-13).

Briefly, any intact organ or tissue may be cut into fairly small pieces and incubated in various fixatives (e.g. formalin, alcohol, etc.) for varying periods of time until the tissue is "fixed". The samples may be virtually any intact tissue surgically removed from the body. The samples may be cut into reasonably small piece(s) that fit on the equipment routinely used in histopathology laboratories. The size of the cut pieces typically ranges from a few millimeters to a few centimeters. The biological sample can also be fluidic extracts, blood, plasma, serum, spinal fluid, lymph fluid, and or splenic preparations.

V. CORRELATION OF CD37 EXPRESSION AND THERAPEUTIC EFFICACY

Anti-CD37 immunoconjugates are provided in U.S. Published Application No 2011/0256153, which is incorporated herein by reference in its entirety. In certain embodiments, the anti-CD37 immunoconjugate is IMGN529. IMGN529 contains the huCD37-3 antibody (comprising the CDRs represented by SEQ ID NOs:22-27, the VH of SEQ ID NO:28 and the VL of SEQ ID NO:29), the SMCC linker, and the DM1 maytansinoid. Sequences of the huCD37-3 antibody are provided below.

```
huCD37-3 VH-CDR1:
                                         (SEQ ID NO: 22)
TSGVS huCD37-3 VH-CDR2:
                                         (SEQ ID NO: 23)
VIWGDGSTN huCD37-3 VH-CDR3:
                                         (SEQ ID NO: 24)
GGYSLAH huCD37-3 VL-CDR1:
                                         (SEQ ID NO: 25)
RASENIRSNLA huCD37-3 VL-CDR2:
                                         (SEQ ID NO: 26)
VATNLAD huCD37-3 VL-CDR3:
                                         (SEQ ID NO: 27)
QHYWGTTWT huCD37-3 VH v. 1.0:
                                         (SEQ ID NO: 28)
QVQVQESGPGLVAPSQTLSITCTVSGFSLTTSGVSWVRQPPGKGLEWLGV
IWGDGSTNYHPSLKSRLSIKKDHSKSQVFLKLNSLTAADTATYYCAKGGY
SLAHWGQGTLVTVSS huCD37-3 VH v. 1.1:
                                         (SEQ ID NO: 32)
QVQVQESGPGLVAPSQTLSITCTVSGFSLTTSGVSWVRQPPGKGLEWLGV
IWGDGSTNYHSSLKSRLSIKKDHSKSQVFLKLNSLTAADTATYYCAKGGY
SLAHWGQGTLVTVSS
```

-continued huCD37-3 VL:
(SEQ ID NO: 29)
DIQMTQSPSSLSVSVGERVTITCRASENIRSNLAWYQQKPGKSPKLLVNV
ATNLADGVPSRFSGSGSGTDYSLKINSLQPEDFGTYYCQHYWGTTWTFGQ
GTKLEIKR huCD37-3 Heavy Chain (HC) v. 1.0:
(SEQ ID NO: 30)
QVQVQESGPGLVAPSQTLSITCTVSGFSLTTSGVSWVRQPPGKGLEWLGV

IWGDGSTNYHPSLKSRLSIKKDHSKSQVFLKLNSLTAADTATYYCAKGGY

SLAHWGQGTLVTVSSASTKGPSVFPLAPSSKSTSGGTAALGCLVKDYFPE

PVTVSWNSGALTSGVHTFPAVLQSSGLYSLSSVVTVPSSSLGTQTYICNV

NHKPSNTKVDKKVEPKSCDKTHTCPPCPAPELLGGPSVFLFPPKPKDTLM

ISRTPEVTCVVVDVSHEDPEVKFNWYVDGVEVHNAKTKPREEQYNSTYRV

VSVLTVLHQDWLNGKEYKCKVSNKALPAPIEKTISKAKGQPREPQVYTLP

PSRDELTKNQVSLTCLVKGFYPSDIAVEWESNGQPENNYKTTPPVLDSDG

SFFLYSKLTVDKSRWQQGNVFSCSVMHEALHNHYTQKSLSLSPG huCD37-3 Heavy Chain (HC) v. 1.1:
(SEQ ID NO: 33)
QVQVQESGPGLVAPSQTLSITCTVSGFSLTTSGVSWVRQPPGKGLEWLGV

IWGDGSTNYHSSLKSRLSIKKDHSKSQVFLKLNSLTAADTATYYCAKGGY

SLAHWGQGTLVTVSSASTKGPSVFPLAPSSKSTSGGTAALGCLVKDYFPE

PVTVSWNSGALTSGVHTFPAVLQSSGLYSLSSVVTVPSSSLGTQTYICNV

NHKPSNTKVDKKVEPKSCDKTHTCPPCPAPELLGGPSVFLFPPKPKDTLM

ISRTPEVTCVVVDVSHEDPEVKFNWYVDGVEVHNAKTKPREEQYNSTYRV

VSVLTVLHQDWLNGKEYKCKVSNKALPAPIEKTISKAKGQPREPQVYTLP

PSRDELTKNQVSLTCLVKGFYPSDIAVEWESNGQPENNYKTTPPVLDSDG

SFFLYSKLTVDKSRWQQGNVFSCSVMHEALHNHYTQKSLSLSPG huCD37-3 Light Chain (LC):
(SEQ ID NO: 31)
DIQMTQSPSSLSVSVGERVTITCRASENIRSNLAWYQQKPGKSPKLLVNV

ATNLADGVPSRFSGSGSGTDYSLKINSLQPEDFGTYYCQHYWGTTWTFGQ

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

In certain embodiments, the immunoconjugate can contain a CD37 antibody produced from the hybridoma of ATCC Deposit Designation PTA-10664, deposited with the American Type Culture Collection (ATCC) at 10801 University Boulevard, Manassas, Va. 20110 on Feb. 18, 2010, or an antigen binding fragment thereof. In certain embodiments, the antibody or antigen-binding fragment thereof comprises the VH-CDRs and the VL-CDRS of the antibody produced from the hybridoma of PTA-10664.

IMGN529 is currently in clinical development for treating leukemias and lymphomas. Methods of administering IMGN529 are provided in U.S. application Ser. No. 14/710,354 (Publication No. 2015/0343077), and Stathis, et al., "Preliminary Findings from a phase I, multi-center, open-label study of the anti-CD37 antibody-drug conjugate (ADC), IMGN529, in adult patients with relapsed or refractory non-Hodgkin Lymphoma (NEIL)," Abstract Number 8526, ASCO Annual Meeting (2014) each of which is incorporated herein by reference.

In certain embodiments, the present disclosure provides a method for identifying subjects that are likely to respond favorably to CD37-targeting therapies due to elevated expression levels of CD37 in the subject, in particular using antibodies and antigen-binding fragments thereof provided herein that can detect a dynamic range of CD37 expression levels, e.g., in IHC.

Evaluation of patient samples and correlation to in vivo efficacy using xenograft models demonstrates the power of the expression analysis for selecting subjects more likely to respond to treatment. IHC provides a score for CD37 expression on tumor cells: 0 (no expression) to 3 (very high levels of expression). Samples scoring 1, 2, or 3 for CD37 expression (or 2 or 3) have an increased likelihood to respond to CD37-targeted anti-cancer therapies at clinically-relevant doses of CD37 immunoconjugates (see e.g., WO 2013/149171, which is incorporated herein by reference). Thus, identification of individuals having an elevated CD37 score would help identify those individuals who might respond to a clinically relevant dosage. Moreover, expression of more uniform levels of CD37 provides better correlation with therapeutic benefit. Thus, a homogenous staining uniformity or a combination of increased staining with heterogeneous staining uniformity can indicate increased CD37 expression. For example, scores of greater than 2 hetero may be used as a patient selection criterion for treatment with a CD37 therapeutic agent. In addition, patient selection criteria can be based on the percentage of cells in a sample that are found to express membrane CD37 at a specified level that reflects both the staining intensity (e.g., 1, 2, or 3) and uniformity (e.g., heterogeneous or homogeneous (see Table 3)). For example, a sample could be characterized as having e.g., at least 25% of cells staining for CD37 positivity at least 2 or greater or at least 75% of the cells staining for CD37 positivity at 2 or greater. In another example, a sample could be characterized as having, e.g., at least 25% of cells staining for CD37 positivity of at least 3 or at least 75% of the cells staining for CD37 positivity at 3. In another example, CD37 expression is given an H-score. In addition, immunological detection (by immunohistochemistry) of CD37 can be scored using H-scores. H-scores combine staining intensity scores with uniformity scores using the calculation provided herein. As described in more detail below, H-scores can range from 1 to 300.

CD37 expression analysis can also be used to identify patients in whom decreased levels of a CD37-targeting anti-cancer therapy ("low dose therapy") can be effective to cause anti-tumor responses. As is appreciated in the art, compounds are generally administered at the smallest dosage that achieves the desired therapeutic response. This is specifically important for therapeutics that cause clinical, and often undesired, side effects. The ability to recognize those subjects with elevated CD37 expression levels allows for potential minimization of the dosage of the CD37-targeting therapeutic, thus decreasing possible side effects, while maintaining therapeutic efficacy.

VI. IMMUNODETECTION METHODS

In certain embodiments, the CD37-binding agents (e.g., antibodies and antigen-binding fragments thereof) can be used in immunodetection methods to identify samples and/or subjects with increased expression or overexpression of CD37. Immunodetection methods include, for example, immunohistochemistry (IHC), enzyme linked immunosorbent assay (ELISA), Western blot, flow cytometry, and fluorescence activated cell sorting (FACS) to mention a few.

In general, the immunodetection methods include obtaining a sample suspected of comprising CD37, and contacting the sample with a first CD37-binding agent (e.g., an anti-CD37 antibody or antigen binding fragment thereof) under conditions effective to allow the formation of immunocomplexes.

In terms of antigen detection, the biological sample analyzed can be any sample in which it is desirable to detect CD37 such as fluidic extract, blood, plasma, serum, spinal fluid, lymph fluid, tissue section or specimen, homogenized tissue extract, biopsy aspirates, a cell, separated and/or purified forms CD37-containing compositions, or any biological fluid. In some embodiments, blood, plasma, or lymph samples or extracts are used.

Contacting the chosen biological sample with the CD37-binding agent (e.g., an anti-CD37 antibody or antigen binding fragment thereof) under effective conditions and for a period of time sufficient to allow the formation of immune complexes (primary immune complexes) is generally a matter of adding the CD37-binding agent (e.g., an anti-CD37 antibody or antigen binding fragment thereof) to the sample and incubating the mixture for a period of time long enough for the CD37-binding agent (e.g., an anti-CD37 antibody or antigen binding fragment thereof) to form immune complexes with, i.e., to bind to, any CD37 present. After this time, the sample, such as a tissue section or fluid extract, ELISA plate, or western blot, will generally be washed to remove any non-specifically bound CD37-binding agent (e.g., an anti-CD37 antibody or antigen binding fragment thereof), allowing only those CD37-binding agents (e.g., an anti-CD37 antibodies or antigen binding fragments thereof) specifically bound within the primary immune complexes to be detected.

In general, the detection of immunocomplex formation is well known in the art and can be achieved through the application of numerous approaches. The CD37-binding agent (e.g., an anti-CD37 antibody or antigen binding fragment thereof) employed in the detection can itself be linked to a detectable label, wherein one would then simply detect this label, thereby allowing the amount of the primary immune complexes in the composition to be determined. Alternatively, the first CD37-binding agent (e.g., an anti-CD37 antibody or antigen binding fragment thereof) that becomes bound within the primary immune complexes can be detected by means of a second binding agent (e.g., antibody or antigen-binding fragment thereof) that has binding affinity for the first CD37-binding agent (e.g., an anti-CD37 antibody or antigen binding fragment thereof). In these cases, the second binding agent can be linked to a detectable label. When the second binding agent is itself an antibody or antigen-binding fragment thereof, it can be referred to as a "secondary" antibody or antigen-binding fragment thereof. The primary immune complexes are contacted with the labeled, secondary binding agent, under effective conditions and for a period of time sufficient to allow the formation of secondary immune complexes. The secondary immune complexes are then generally washed to remove any non-specifically bound labeled secondary binding agents, and the remaining label in the secondary immune complexes is then detected.

Further methods include the detection of primary immune complexes by a two-step approach. A second binding agent (e.g., antibody or antigen-binding fragment thereof) that has binding affinity for the first CD37-binding agent (e.g., an anti-CD37 antibody or antigen binding fragment thereof) is used to form secondary immune complexes, as described herein. After washing, the secondary immune complexes are contacted with a third binding agent that has binding affinity for the second binding agent (e.g., antibody or antigen-binding fragment thereof), again under effective conditions and for a period of time sufficient to allow the formation of immune complexes (tertiary immune complexes). The third binding agent is linked to a detectable label, allowing detection of the tertiary immune complexes thus formed. This system may provide for signal amplification if this is desired.

In another embodiment, a biotinylated CD37-binding agent (e.g., an anti-CD37 antibody or antigen binding fragment thereof) is used to detect CD37, and a second binding agent (e.g., antibody or antigen-binding fragment thereof) is then used to detect the biotin. In that method, the sample to be tested is first incubated in a solution comprising the biotinylated CD37-binding agent (e.g., an anti-CD37 antibody or antigen binding fragment thereof). If CD37 is present, some of the binding agent binds to the CD37 to form a biotinylated CD37-binding agent-CD37 complex. The complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution comprising the second binding agent (e.g., antibody or antigen-binding fragment thereof) that binds to biotin. This second binding agent is labeled, as for example with an enzyme that can be used to detect the presence of the antibody/antigen complex by histoenzymology using a chromogen substrate. With suitable amplification, a conjugate can be produced that is macroscopically visible.

In one embodiment, immunohistochemistry (IHC) is used for immunological detection. Using IHC, detection of CD37 in a sample can be achieved by targeting a sample with a probe e.g., an anti-CD37 antibody or antigen-binding fragment thereof. The probe can be linked, either directly or indirectly to a detectable label or can be detected by another probe that is linked, either directly or indirectly to a detectable label.

In some embodiments, IHC can distinguish between different levels of protein expression, e.g., calibrated IHC. In some embodiments, the IHC can distinguish staining intensity for samples having low CD37, intermediate CD37, or high CD37 expression.

In one embodiment, immunological detection (by immunohistochemistry) of CD37 is scored for both intensity and uniformity (percent of stained cells—membrane only). Comparative scales for CD37 expression for intensity correlate as 0—Negative, 0-1—Very Weak, 1—Weak, 1-2—Weak to Moderate, 2—Moderate, 2-3—Moderate to Strong, 3—Strong to Very Strong. Quantitatively, Score 0 represents that no staining is observed or membrane staining is observed in less than 10% of tumor cells. Score 1 or 1+ represents that a faint/barely perceptible membrane staining is detected in more than 10% of the tumor cells. The cells are only stained in part of their membrane. Scores 1 are 1+ are used interchangeably. For Score 2, a weak to moderate complete membrane staining is observed in more than 10% of the tumor cells. Lastly, Score 3 represents that a moderate to strong complete membrane staining is observed in more than 10% of the tumor cells. Those samples with 0 or 1 score for CD37 expression can be characterized as not having elevated CD37 expression, whereas those samples with 2 or 3 scores can be characterized as overexpressing or having elevated CD37. In another embodiment, using the antibodies, antigen-binding fragments thereof, or polypeptides provided herein, those samples with a 0 score for CD37 expression can be characterized as not having elevated CD37 expression, those samples with a 1 score can be characterized as having increased expression of CD37, and those samples with 2 or 3 scores can be characterized as overexpressing or having elevated CD37.

In certain embodiments, a score of at least 2 in a sample obtained from a subject identifies the subject as a candidate for treatment with an anti-CD37 treatment regimen (e.g., IMGN529). In certain embodiments, a score of at least 3 in a sample obtained from a subject identifies the subject as a candidate for treatment with an anti-CD37 treatment regimen (e.g., IMGN529).

Samples overexpressing CD37 can also be rated by immunohistochemical scores corresponding to the number of copies of CD37 molecules expressed per cell, or antibodies bound per cell (ABC), and can been determined biochemically.

Comparative scales for CD37 uniformity (percent cell membrane staining) are as follows: Negative=0%; Focal=<25%; heterogeneous (hetero)=25-75%, and homogeneous (homo)=>75%.

In certain embodiments, a score of at least 2 hetero in a sample obtained from a subject identifies the subject as a candidate for treatment with an anti-CD37 treatment regimen (e.g., IMGN529). In certain embodiments, a score of at least 2 homo in a sample obtained from a subject identifies the subject as a candidate for treatment with an anti-CD37 treatment regimen (e.g., IMGN529). In certain embodiments, a score of at least 3 hetero in a sample obtained from a subject identifies the subject as a candidate for treatment with an anti-CD37 treatment regimen (e.g., IMGN529). In certain embodiments, a score of at least 3 homo in a sample obtained from a subject identifies the subject as a candidate for treatment with an anti-CD37 treatment regimen (e.g., IMGN529).

In one embodiment, immunological detection (by immunohistochemistry) of CD37 is scored using H-scores. H-scores combine staining intensity scores (e.g., a score of 0 to 3, wherein 0 represents no staining, and 3 represents strong staining) with the percentage of cells that are positive for membrane staining (i.e., uniformity). An H-score can be calculated as follows:

> $H$ score=[0*(percentage of cells staining at intensity 0)]+[1*(percentage of cells staining at intensity 1)]+[2*(percentage of cells staining at intensity 2)]+[3*(percentage of cells staining at intensity 3)]. Accordingly, an $H$-score can range from 0 (no cell membranes staining) to 300 (all cell membrane staining at intensity 3).

By way of example, an H-score in a subject having cancer can be as follows:

> $H$ score=(75% at intensity 0)+(0% at intensity 1)+(0% at intensity 2)+(25% at intensity 3)=75; or > $H$ score=(0% at intensity 0)+(75% at intensity 1)+(0% at intensity 2)+(25% at intensity 3)=150.

In another example, an H-score in a subject having cancer may be as follows:

> $H$ score=(75% at intensity 0)+(0% at intensity 1)+(25% at intensity 2)+(0% at intensity 3)=50; or > $H$ score=(0% at intensity 0)+(75% at intensity 1)+(25% at intensity 2)+(0% at intensity 3)=125.

In one embodiment, immunological detection (by immunohistochemistry) of CD37 is scored using percent positivity and intensity across a sample. In this embodiment, selection for treatment with an anti-CD37 treatment regimen is based on the percentage of cells in a sample that are found to express membrane CD37 at a specified level that reflects both the staining intensity (e.g., 1, 2, or 3) and uniformity (e.g., heterogeneous or homogeneous (see Table 3)). For example, a sample having at least 25% (i.e., 25-75% or >75%) of the cells staining for CD37 positivity at 3 could be characterized as "3 hetero" and "3 homo" or, collectively, as "at least 25% positive at 3."

IHC can be performed manually or using an automated system (e.g., using an automated strainer). IHC can be performed on cells, cell pellets, tissues, preparations from blood, plasma, serum, or lymph fluid, etc. In some embodiments, the samples are fixed samples. In some embodiments, the samples are paraffin embedded samples. In some embodiments, the samples are formalin fixed and paraffin embedded samples.

In one embodiment, Enzyme-Linked Immuno Sorbent Assay (ELISA) is used for immunological detection. The underlying methodology of ELISA is well known in the art. See, for example, Lequin R, "Enzyme immunoassay (EIA)/enzyme-linked immunosorbent assay (ELISA)," *Clin. Chem.* 51:2415-2418 (2005), which is herein incorporated by reference in its entirety. In one exemplary ELISA, CD37-binding agents (e.g., antibodies or antigen-binding fragments thereof) are immobilized onto a selected surface exhibiting protein affinity, such as a well in a polystyrene microtiter plate. Then, a test sample, such as a clinical sample, containing or suspected of containing CD37 is added to the wells. After binding and washing to remove non-specifically bound immunocomplexes, the bound CD37 can be detected. Detection is generally achieved by the addition of a second antibody or antigen-binding fragment thereof specific for CD37, that is linked to a detectable label. This type of ELISA is a "sandwich ELISA". Detection can also be achieved by the addition of a second antibody or antigen-binding fragment thereof, followed by the addition of a third antibody or antigen-binding fragment thereof that has binding affinity for the second antibody or antigen-binding fragment thereof, with the third antibody or antigen-binding fragment thereof being linked to a detectable label. Color formation can be monitored spectophotometrically and related to concentration of CD37 by calibration to a standard curve. In another exemplary ELISA, the test samples are immobilized onto the well surface and then contacted with the CD37-binding agents (e.g., antibodies or antigen-binding fragments thereof). After binding and washing to remove non-specifically bound immunocomplexes, the bound CD37 is detected. Where the initial CD37-binding agents (e.g., antibodies or antigen-binding fragments thereof) are linked to a detectable label, the immunocomplexes can be detected directly. Again, the immunocomplexes can be detected using a second binding agent that has binding affinity for the first binding, with the second binding agent being linked to a detectable label. Another ELISA in which test samples are immobilized, involves the use of competition in the detection. In this ELISA, labeled CD37-binding agents (e.g., antibodies or antigen-binding fragments thereof) are added to the wells, allowed to bind to CD37, and detected by means of their label. The amount of CD37 in a sample is then determined by mixing the sample with the labeled CD37-binding agents (e.g., antibodies or antigen-binding fragments thereof) before or during incubation with coated wells. The presence of CD37 in the sample acts to reduce the amount of CD37-binding agents (e.g., antibodies or antigen-binding fragments thereof) available for binding to the well and thus reduces the ultimate signal.

In one embodiment, a Western blot is used for immunological detection. For Western blot proteins are extracted from a cell sample and are subjected to electrophoresis (e.g., SDS-PAGE) and blotted to a membrane (e.g., nitrocellulose or PVDF). The membrane is then contacted with a CD37-binding agent (e.g., antibody or antigen-binding fragment thereof), which can be either directly labeled or further subjected to a secondary labeled binding agent. Detection can be, for example, by autoradiography, colorimetric reaction, or chemiluminescence. This method allows both quantitation of an amount of substrate and determination of its identity by a relative position on the membrane which is indicative of a migration distance in the acrylamide gel during electrophoresis.

In one embodiment, flow cytometry is used for immunological detection. Thus, for example, the number of antibodies bound per cell (ABC) can be assessed using flow cytometry. A high number of anti-CD37 antibodies bound per cell can indicate high CD37 expression levels and a high likelihood to be susceptible to treatment with an anti-CD37 antibody or immunoconjugate thereof.

In one embodiment, FACS is used for immunological detection. FACS analysis enables the detection of CD37 on cell membranes. Briefly, CD37-binding agents (e.g., antibodies or antigen-binding fragments thereof) are linked to fluorophores and detection is performed by means of a cell sorting machine that reads the wavelength of light emitted from each cell as it passes through a light beam. This method can employ two or more antibodies simultaneously.

VII. DETECTION AGENTS

The CD37-binding agents provided herein can be linked to at least one agent to form a detection conjugate. In addition, the CD37-binding agents provided herein can be detected by a detection agent that is linked to at least one agent to form a detection conjugate. Detection molecules and moieties are well known in the art. In order to increase the efficacy of antibody molecules as diagnostic it is conventional to link or covalently bind or complex at least one desired molecule or moiety. Such a molecule or moiety may be, but is not limited to, at least one reporter molecule. A reporter molecule is defined as any moiety that may be detected using an assay. Non-limiting examples of reporter molecules that have been conjugated to antibodies include enzymes, radiolabel s, haptens, fluorescent labels, phosphorescent molecules, chemiluminescent molecules, chromophores, luminescent molecules, photoaffinity molecules, colored particles and/or ligands, such as biotin.

Antibody or antigen-binding fragment detection conjugates contemplated in the present invention include those for use in vitro, where the antibody or fragment is linked to a secondary binding ligand and/or to an enzyme (an enzyme tag) that will generate a colored product upon contact with a chromogenic substrate. The CD37 antibodies and antigen-binding fragments thereof provided herein are particularly useful for conjugates methods because, for example, they are able to detect a dynamic range of CD37. Examples of suitable enzymes include urease, alkaline phosphatase, (horseradish) hydrogen peroxidase and/or glucose oxidase. In some embodiments, secondary binding ligands are biotin and/or avidin and streptavidin compounds.

In the case of enzymes, the amount of color developed and measured will be a direct measurement of the amount of CD37 present. If HRP is the label, the color can be detected using the substrate 3,3',5,5'-tetramethyl benzidine (TMB), e.g., at 450 nm absorbance. Alternatively, other chromogenic substrates for HRP such as 3,3'-Diaminobenzidine (DAB) or 2,2'-azino-bis(3-ethylbenzothiazoline-6-sulphonic acid) (ABTS). Substrates such as TMB, DAB, and ABTS can be used, for example, in immunodetection methods using ELISA.

3,3'-diaminobenzidine (DAB) is a substrate for enzymes such as HRP that produces a brown end product that is highly insoluble in alcohol and other organic solvents. Oxidation of DAB also causes polymerization, resulting in the ability to react with osmium tetroxide, and thus increasing its staining intensity and electron density. Of the several metals and methods used to intensify the optical density of polymerized DAB, gold chloride in combination with silver sulfide appears to be the most successful.

3-Amino-9-ethylcarbazole (AEC), is a substrate for enzymes such as HRP, and upon oxidation, forms a rose-red end product that is alcohol soluble. Therefore, specimens processed with AEC must not be immersed in alcohol or alcoholic solutions (e.g., Harris' hematoxylin). Instead, an aqueous counterstain and mounting medium should be used.

4-Chloro-1-naphthol (CN) is a substrate for enzymes such as HRP that precipitates as a blue end product. Because CN is soluble in alcohol and other organic solvents, the specimen must not be dehydrated, exposed to alcoholic counterstains, or coverslipped with mounting media containing organic solvents. Unlike DAB, CN tends to diffuse from the site of precipitation.

p-Phenylenediamine dihydrochloride/pyrocatechol (Hanker-Yates reagent) is a substrate for enzymes such as HRP that gives a blue-black reaction product that is insoluble in alcohol and other organic solvents. Like polymerized DAB, this reaction product can be osmicated. Varying results have been achieved with Hanker-Yates reagent in immunoperoxidase techniques.

Chemiluminescent substrates, such as ECL, can be used. Substrates such as ECL can be used, for example, in immunodetection methods using Western blotting.

Exemplary fluorescent labels contemplated for use as binding agent (e.g., antibody) conjugates include Alexa 350, Alexa 430, Alexa 488, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Dylight 488, Fluorescein Isothiocyanate (FITC), Green fluorescent protein (GFP), HEX, 6-JOE, Oregon Green 488, Oregon Green 500, Oregon Green 514, Pacific Blue, Phycoerythrin, REG, Rhodamine Green, Rhodamine Red, tetramethyl rhodamin (TMR) Renographin, ROX, TAMRA, TET, Tetramethylrhodamine, Texas Red, and derivatives of these labels (i.e., halogenated analogues, modified with isothiocynate or other linker for conjugating, etc.), for example. An exemplary radiolabel is tritium.

Molecules containing azido groups may also be used to form covalent bonds to proteins through reactive nitrene intermediates that are generated by low intensity ultraviolet light (Potter & Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; and Dholakia et al., 1989) and can be used as antibody binding agents.

In other embodiments of the invention, CD37-binding agents (e.g., antibodies and antigen-binding fragments thereof) or secondary binding agents are radiolabeled with nuclides such as tritium. In additional embodiments, nanogold particles (such as sizes from about 0.5 nm-40 nm) and/or Quantum Dots (Hayward, Calif.) are employed.

In some embodiments, CD37 is detected using the Optiview DAB IHC Detection reagent (Ventanna catalog #760-700).

In some embodiments, CD37 is detected using the BenchMark Ultra staining system.

In some embodiments, CD37 is detected using the BenchMark Ultra staining system using the Optiview DAB IHC Detection reagent (Ventanna catalog #760-700).

VIII. COMPOSITIONS AND KITS

Also provided herein are compositions and kits for use in the practice of the methods disclosed herein. Such kits may comprise containers, each with one or more of the various reagents (typically in concentrated form) utilized in the methods, including, for example, one or more CD37-binding agents (e.g., antibodies or antigen-binding fragments thereof), buffers, and/or reagents and instrumentation for the detection of CD37 to support the practice of the invention. The kit can further comprise a second binding agent that binds to the CD37-binding agent, and optionally a third binding agent that binds to the second binding agent. The CD37-binding agent, the second binding agent, or the third binding agent can be bound to a detection reagent or the kit can comprise reagents for coupling a detection reagent to the CD37-binding agent, the second binding agent, or the third binding agent. A label or indicator describing, or a set of instructions for use of, kit components in a ligand detection method of the present invention, will also be typically included, where the instructions may be associated with a package insert and/or the packaging of the kit or the components thereof.

In certain embodiments, a kit comprises a first antibody or antigen-binding fragment that binds to CD37, a second antibody or antigen-binding fragment that binds to the first antibody or antigen-binding fragment, a third antibody or antigen-binding fragment that binds to the second antibody or antigen binding fragment, wherein the third antibody or antigen-binding fragment is linked to detection reagent (e.g., an enzyme tag), optionally a substrate for the detection reagent (e.g., TMB, DAB, or ABTS), and optionally a CD37 protein or cell sample containing CD37 (e.g., a paraffin-embedded sample). The kits can further comprise a therapeutic agent for the treatment of cancer, such as an anti-CD37 immunoconjugate.

In one embodiment, the CD37-binding agent is 1B11-2 or an antigen-binding fragment thereof. In one embodiment, the CD37-binding agent is an antibody or antigen-binding fragment that binds to the same CD37 epitope as 1B11-2. In one embodiment, the CD37-binding agent is an antibody or antigen-binding fragment that comprises the six CDRs of 1B11-2. In one embodiment, the CD37-binding agent is an antibody or antigen-binding fragment that comprises the VH and VL of 1B11-2.

In one embodiment the CD37-specific antibody or antigen-binding fragment thereof is included at a concentration of about 0.1 to about 20 µg/mL, about 0.1 to about 15 µg/mL, about 0.1 to about 10 µg/mL, about 0.5 to about 20 µg/mL, about 0.5 to about 15 µg/mL, about 0.5 to about 10 µg/mL, about 1 to about 20 µg/mL, about 1 to about 15 µg/mL, about 1 to about 10 µg/mL, about 2 to about 20 µg/mL, about 2 to about 15 µg/mL, or about 2 to about 10 µg/mL. In another embodiment, the CD37-specific antibody or antigen-binding fragment thereof is included at a concentration of about 1.5 µg/mL, about 2 µg/mL, about 3 µg/mL, about 4 µg/mL, about 5 µg/mL, about 6 µg/mL, about 7 µg/mL, about 8 µg/mL, about 9 µg/mL, or about 10 µg/mL. In another embodiment, the CD37-specific antibody or antigen-binding fragment thereof is included at a concentration of about 2 µg/mL. In another embodiment, the CD37-specific antibody or antigen-binding fragment thereof is included at a concentration of about 10 µg/mL.

In another embodiment, the antibody or antigen-binding fragment thereof is included in concentrated solution with instructions for dilutions to achieve a final concentration of about 1 to about 20 µg/mL, about 1 to about 15 µg/mL, about 1 to about 10 µg/mL, about 2 to about 20 µg/mL, about 2 to about 15 µg/mL, or about 2 to about 10 µg/mL. In another embodiment, the antibody or antigen-binding fragment thereof is included in concentrated solution with instructions for dilutions to achieve a final concentration of about 1.5 µg/mL, about 2 µg/mL, about 3 µg/mL, about 4 µg/mL, about 5 µg/mL, about 6 µg/mL, about 7 µg/mL, about 8 µg/mL, about 9 µg/mL, or about 10 µg/mL. In another embodiment, the antibody or antigen-binding fragment thereof is included in concentrated solution with instructions for dilutions to achieve a final concentration of about 2 µg/mL. In another embodiment, the antibody or antigen-binding fragment thereof is included in concentrated solution with instructions for dilutions to achieve a final concentration of about 2.1 µg/mL. In another embodiment, the antibody or antigen-binding fragment thereof is included in concentrated solution with instructions for dilutions to achieve a final concentration of about 4.2 µg/mL. In another embodiment, the antibody or antigen-binding fragment thereof is included in concentrated solution with instructions for dilutions to achieve a final concentration of about 8.4 µg/mL In another embodiment, the antibody or antigen-binding fragment thereof is included in concentrated solution with instructions for dilutions to achieve a final concentration of about 10 µg/ml. The kit can also include instructions for detection and scoring of CD37 expression. The kit can also include control or reference samples. Non-limiting examples of control or reference samples include cell pellets or tissue culture cell lines derived from normal (normal control) or tumor (positive control) samples. Exemplary cell lines include cell lines stably or transiently transfected with an expression vector that expresses CD37. Additional examples include cell pellets and tissue samples described in the Examples. Positive cell lines include Daudi cells (high expression), Ramos cells (moderate expression) and Namalwa cells (moderate to low expression). Human tonsil serves as both a positive and negative control tissue as the germinal centers and mantle zones show high expression and the interfollicular region shows no expression. In some embodiments, the control or reference samples are paraffin-embedded samples.

In some embodiments, a kit is a packaged combination including the basic elements of: (a) capture reagents comprised of the monoclonal antibodies against human CD37; and (b) detection reagents which can also comprise CD37 monoclonal antibodies, but can also comprise detectable (labeled or unlabeled) antibodies that bind to CD37. These basic elements are defined herein.

In one embodiment, the kit further comprises a solid support for the capture reagents, which can be provided as a separate element or on which the capture reagents are already immobilized. Hence, the capture antibodies in the kit can be immobilized on a solid support, or they can be immobilized on such support that is included with the kit or provided separately from the kit.

In one embodiment, the capture reagent is coated on a microtiter plate. The detection reagent can be labeled antibodies detected directly or unlabeled antibodies that are detected by labeled antibodies directed against the unlabeled antibodies raised in a different species. Where the label is an enzyme, the kit will ordinarily include substrates and cofactors required by the enzyme, and where the label is a fluorophore, a dye precursor that provides the detectable chromophore. Where the detection reagent is unlabeled, the kit can further comprise a detection means for the detectable antibodies, such as the labeled antibodies directed to the unlabeled antibodies, e.g., in a fluorimetric-detected format. Where the label is an enzyme, the kit will ordinarily include substrates and cofactors required by the enzyme, where the label is a fluorophore, a dye precursor that provides the detectable chromophore, and where the label is biotin, an avidin such as avidin, streptavidin, or streptavidin conjugated to HRP or β-galactosidase with MUG.

In one embodiment, the capture reagent is the CD37 antibody 1B11-2 or an antibody comprising the sequences of antibody 1B11-2. In one embodiment, the detection reagent is the CD37 antibody 1B11-2 or an antibody comprising the sequences of antibody 1B11-2. In another embodiment, the detection reagent CD37 antibody 1B11-2 or an antibody comprising the sequences of antibody 1B11-2 is biotinylated.

In another embodiment, the kit further comprises a detection reagent selected from the group consisting of: an enzyme, a fluorophore, a radioactive label, and a luminophore. In another embodiment, the detection reagent is selected from the group consisting of: biotin, digoxigenin, fluorescein, tritium, and rhodamine.

The kit can also contain instructions for carrying out the assay, and/or CD37 protein, or fragments thereof (e.g., CD37 extracellular domain or the CD37 extracellular domain with all or a part of the GPI linkage domain) as an antigen standard, as well as other additives such as stabilizers, washing and incubation buffers, and the like. In one embodiment, the CD37 antigen standard is a CD37-protein described in the Examples herein. The kit can also include instructions for detection and scoring of CD37 expression.

The components of the kit can be provided in predetermined ratios, with the relative amounts of the various reagents suitably varied to provide for concentrations in solution of the reagents that substantially maximize the sensitivity of the assay. Particularly, the reagents can be provided as dry powders, usually lyophilized, including excipients, which on dissolution will provide for a reagent solution having the appropriate concentration for combining with the sample to be tested.

Compositions comprising the antibodies or antigen-binding fragments described herein are also provided. In one embodiment, a composition comprises an anti-CD37 antibody or antigen-binding fragment described herein and a buffer, e.g., a buffer that can be used in a detection assay such as IHC, ELISA, or FACS. Such buffers are known to those of ordinary skill in the art and include diluents. By way of example, IHC buffers can contain, for example, casein serum or albumin (such as calf serum, goat serum, or BSA), Tween or Triton, PBS and/or sodium azide or any combination thereof. IHC buffers are also provided herein and known to those of ordinary skill in the art. ELISA buffers are also provided herein and known to those of ordinary skill in the art. ELISA buffers can contain, for example, serum or albumin (such as calf serum, goat serum, or BSA), non-fat dry milk, casein, and/or gelatin or any combination thereof. Certain FACS buffers are provided herein, e.g., in the working examples. FACS buffers can also contain, for example, serum or albumin (such as calf serum, goat serum, or BSA) and/or sodium azide. FACS buffers can also contain PBS, EDTA, and/or DNAse or any combination thereof.

Embodiments of the present disclosure can be further defined by reference to the following non-limiting examples, which describe in detail preparation of certain antibodies of the present disclosure and methods for using antibodies of the present disclosure. It will be apparent to those skilled in the art that many modifications, both to materials and methods, can be practiced without departing from the scope of the present disclosure.

IX. EXAMPLES

It is understood that the examples and embodiments described herein are for illustrative purposes only and that various modifications or changes in light thereof will be suggested to persons skilled in the art and are to be included within the spirit and purview of this application.

Example 1

Generation of CD37 Hybridomas

Hybridomas producing anti-human CD37 monoclonal antibodies that are suitable for immunohistochemistry (IHC) staining (antibodies of the present disclosure) were selected from approximately 4,800 hybridomas. The hybridomas were produced by immunization of wild-type Balb/c mice with recombinant CD37 antigen hCD37-LEL produced in E. coli. This antigen comprises amino acids 107 to 242 of CD37 with a 6xHis-tag added to the 3'end to facilitate purification (SEQ ID NO:15). The immunization with CD37 recombinant protein was done by subcutaneous injection of the protein emulsified in complete Freund's adjuvant (CFA) or incomplete Freund's adjuvant for boost (Sigma) or Magic mouse adjuvant (Creative Diagnostics). Generally, mice were immunized five times with two week intervals before receiving a final boost by intraperitoneal injection of the immunogen three days prior to fusion.

A total of 5 independent fusions were carried out using spleen cells that originated from the immunized wild-type Balb/c mice and murine myeloma P3X63Ag8.653 cells (P3 cells). Cell fusion was conducted using an ECM200 electrofusion machine (BTX Harvard Apparatus) according to standard protocols. Each fusion yielded more than 1,000 hybridomas.

Antibodies produced by these hybridomas were screened and confirmed by ELISA using different recombinant versions of the CD37 antigen. hCD37-LEL comprises amino acid 107 to 242 of human CD37 with a 6xHis-tag added to the 3'end to facilitate purification (SEQ ID NO:15) and was produced in E. coli. hCD37-Fc-LAGAcomprises amino acids 107 to 235 of human CD37 with a human IgG1 Fc-domain added to the 3'end to facilitate purification (SEQ ID NO:17) and was produced in HEK-293T cells. hCD37-ECD-Fc comprises amino acids 107 to 235 of human CD37 with a murine IgG2a Fc-domain added to the 3'end to facilitate purification (SEQ ID NO:16) and was produced in HEK-293T cells.

For native conditions, recombinant proteins were diluted directly into 50 mM Sodium bicarbonate coating buffer (Sigma-Aldrich). For denaturing conditions, recombinant proteins were incubated in 1% SDS with 50 mM DTT for 30 minutes at 65° C., followed by incubation with 100 mM Iodoacetamide for 30 minutes at room temperature prior to diluting into 50 mM Sodium bicarbonate coating buffer. Each recombinant protein was immobilized at approximately 25-100 ng/well onto microtiter plates by overnight incubation at 4° C.

Plates were washed once with PBS supplemented with 0.05% Tween-20 and blocked with PBS supplemented with 1% bovine serum albumin (BSA). Plates were washed three times with PBS supplemented with 0.05% Tween-20, and hybridoma supernatants were added to the plates. Plates were incubated for one hour at room temperature, washed three times as above, and incubated with HRP-labeled goat anti-murine secondary antibody (Jackson ImmunoResearch, diluted at 1:5,000) for one hour at room temperature. The plates were washed three times as above, and bound HRP-conjugated antibody was detected by adding the HRP-substrate TMB (Bio-FX). Plates were incubated for approximately 10 minutes, and then color development was stopped with stop solution (Bio-FX). Absorbance at 450 nm was measured for each plate in a multiplate reader. Hybridoma supernatant from clone 1B11 resulted in a strong positive ELISA signal for both native and denaturing conditions (see FIG. 1A) and was chosen for subcloning. Two subclones were obtained from clone 1B11: 1B11-2 and 1B11-20. Hybridoma supernatant from both subclones resulted in a strong positive ELISA signal for both native and denaturing conditions (see FIG. 1B), and clone 1B11-2 was chosen for further analysis.

Example 2

Characterization of the Anti-CD37 Antibodies by ELISA

Figure 2:
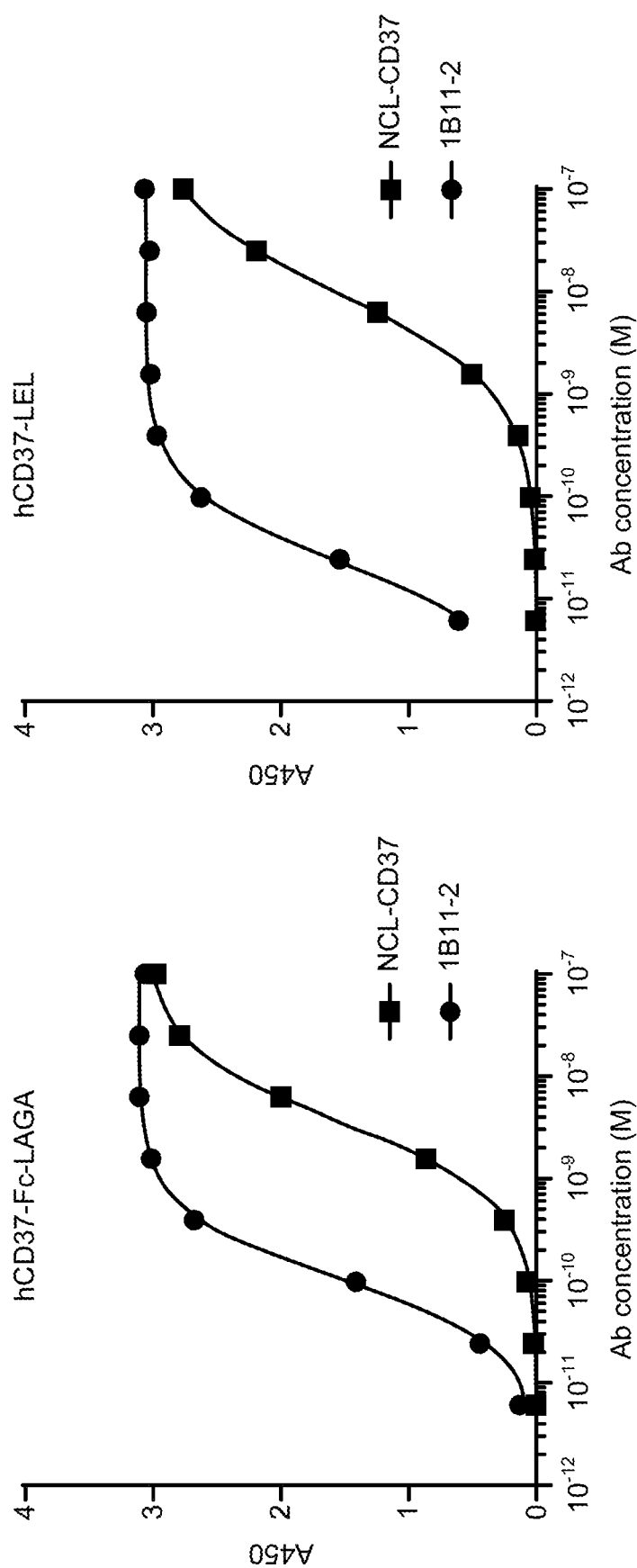
FIG. 2 shows that antibody 1B11-2 binds with greatly improved affinity to both native hCD37-Fc-LAGA and hCD37-LEL proteins as compared to a reference anti-CD37 antibody, NCL-CD37 (clone CT1, Leica Biosystems).
Figure 3:
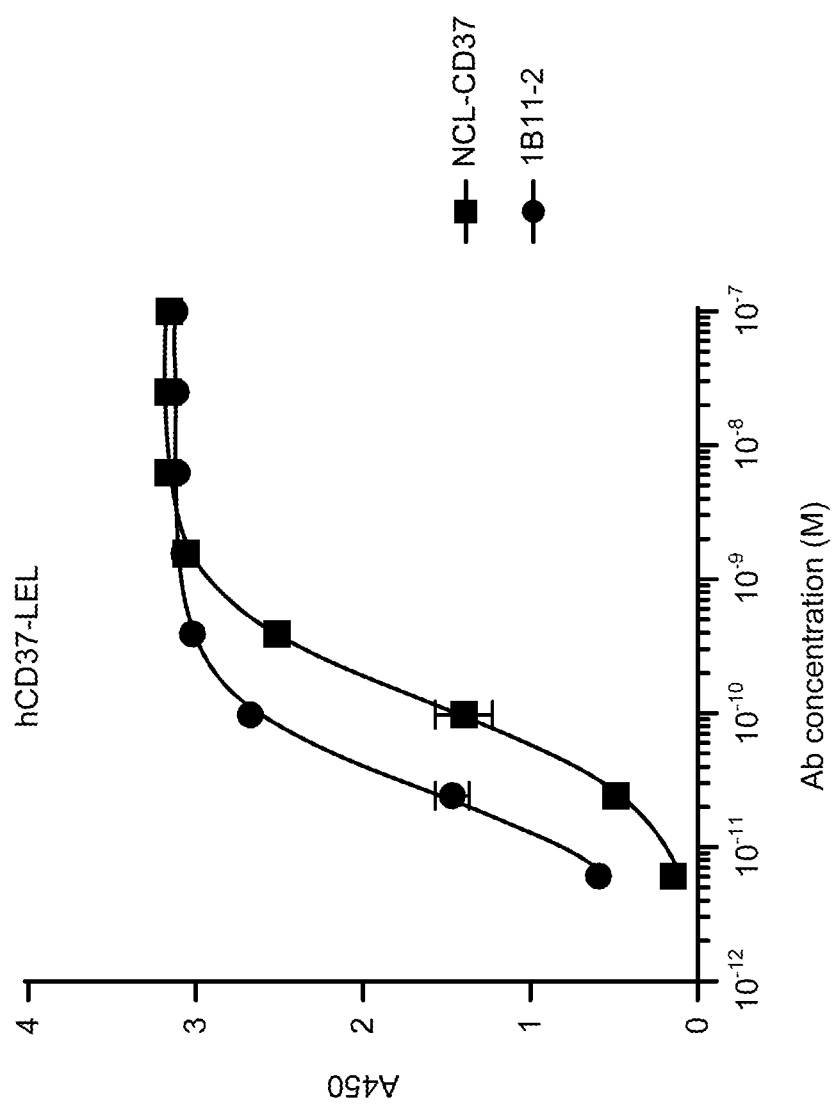
FIG. 3 shows that antibody 1B11-2 binds with greatly improved affinity to denatured hCD37-LEL protein as compared to NCL-CD37.

Antibody from 1B11-2 was purified using standard protein-A chromatography. An anti-CD37 antibody sold by Leica Biosystems (product code NCL-CD37) was used for comparison. The binding of the anti-CD37 antibodies was examined by ELISA with recombinant CD37 proteins used as the antigen. Each recombinant protein was immobilized at approximately 25-100 ng/well on microtiter plates in Sodium bicarbonate coating buffer (Sigma-Aldrich) using either native or denatured conditions as described above. Plates were washed once with PBS supplemented with 0.05% Tween-20 and blocked with PBS supplemented with 1% bovine serum albumin (BSA). Plates were washed three times with PBS supplemented with 0.05% Tween-20 and purified antibodies were added to the plates. Plates were incubated for one hour at room temperature, washed three times as above, and incubated with HRP-labeled goat anti-murine secondary antibody (Jackson ImmunoResearch, diluted at 1:5,000) for one hour at room temperature. The plates were washed three times as above, and bound HRP-conjugated antibody was detected by adding the HRP-substrate TMB (Bio-FX). Plates were incubated for approximately 10 minutes, and then color development was stopped with stop solution (Bio-FX). Absorbance at 450 nm was measured for each plate in a multiplate reader. Representative results are shown in FIG. 2 for binding to native hCD37-Fc-LAGA and hCD37-LEL. Antibody 1B11-2 binds with greatly improved affinity to both native CD37 proteins as compared to NCL-CD37. Results are shown in FIG. 3 for binding to denatured hCD37-LEL protein. Antibody 1B11-2 binds with improved affinity to denatured hCD37-LEL protein as compared to NCL-CD37.

Example 3

Antigen Epitope Characterization

Figure 4:
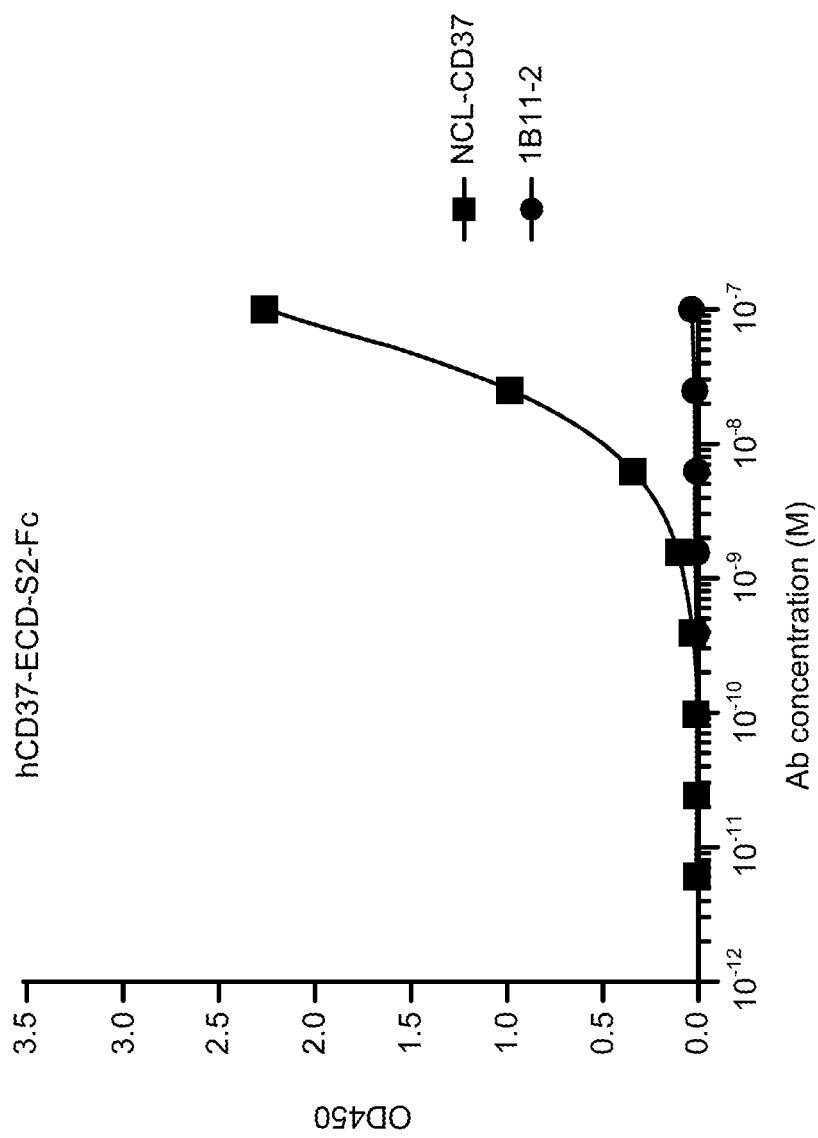
FIG. 4 shows that antibody 1B11-2 does not bind to the truncated hCD37-ECD-S2-Fc protein (S2 refers to the second segment of the large extracellular domain of CD37, containing amino acids 138 to 176, SEQ ID NO:18), while NCL-CD37 retains binding to this CD37 protein.

Binding of the anti-CD37 antibodies was further examined by ELISA with recombinant CD37 protein hCD37-ECD-S2-Fc used as the antigen under native conditions as described above. (S2 refers to the second segment of the large extracellular domain of CD37, containing amino acids 138 to 176). Representative results are shown in FIG. 4. hCD37-ECD-S2-Fc comprises amino acids 107 to 109 and 138 to 235 of human CD37 with a murine IgG2a Fc-domain added to the 3'end to facilitate purification (SEQ ID NO:18) and was produced in HEK-293T cells. Antibody 1B11-2 does not bind to hCD37-ECD-S2-Fc, while NCL-CD37 retains binding to this CD37 protein fragment. Similar results were seen with Western blot analysis.

Example 4

Immunohistochemical Evaluation of Anti-CD37 Antibodies

FFPE CD37 IHC

Purified antibody from clone 1B11-2 was analyzed and compared with Leica's NCL-CD37 mouse monoclonal antibody by IHC. The analysis was performed using the Leica Bond RX Automated Stainer and the reagents and conditions listed in Table 1.

TABLE 1

IHC Reagents and Assay Conditions

| Step | Action/Reagent (Vendor) | Time |
|---|---|---|
| Bake | Temperature: 60° C. | 30 Minutes |
| Dewax | Bond Dewax Solution (Leica) 100% Reagent Grade Ethanol (Arantik) | Fixed |
| Antigen Retrieval | Bond Epitope Retrieval 1 (citrate buffer based pH 6.0 solution) | 20 Minutes |
| Endogenous Peroxidase Block | Peroxide (Leica) | 5 Minutes |
| Test Article | ImmunoGen, Inc. generated antibodies at varying concentrations prepared by diluting in Leica Antibody Diluent | 15 Minutes |
| Detection | Post Primary Regent (Leica) | 8 Minutes |
|  | Polymer (Leica) | 8 Minutes |
|  | Mixed DAB (Leica) | 10 Minutes |
| Counterstain | Hematoxylin (Leica) | 5 Minutes |

Slides containing formalin fixed paraffin embedded (FFPE) cell samples, normal tissues, diffuse large B-cell lymphoma patient tumor biopsies, follicular lymphoma patient tumor biopsies, and chronic lymphocytic leukemia/small lymphocytic lymphoma patient tumor biopsies were baked at 60° C. and dewaxed using Bond Dewax Solution and 100% Ethanol. Heat induced epitope retrieval using Bond Epitope Retrieval 1 (citrate buffer based pH 6.0 solution) was performed for 20 minutes and endogenous peroxidase was blocked with peroxide for 5 minutes. Slides were incubated with ImmunoGen, Inc. generated 1B11-2 antibody, Leica/Novocastra NCL-CD37 antibody (clone CT1) or Leica/Novocastra muIgG1 control antibody at varying concentrations for 15 minutes. Bound antibodies were detected by incubation with the Leica Bond Refine detection system. Following the application of the antibodies, slides were incubated with Post Primary Reagent (rabbit anti-mouse IgG) for 8 minutes, Polymer (goat anti-rabbit polymer) for 8 minutes, and DAB (3,3-diaminobenzidine tetrahydrochloride) for 10 minutes. This resulted in a brown color signal. Slides were counterstained with hematoxylin for 5 minutes.

FFPE normal spleen and tonsil tissue samples were derived from human tissue blocks obtained from Mercy Health Systems and Ardais Corporationas as outlined below. FFPE cell samples were derived from the Daudi and Ramos cell lines supplied by DSMZ (German Collection of Microorganisms and Cell Cultures), and the Namalwa cell line was supplied by American Tissue Culture Collection. Slides containing sections of samples were prepared from FFPE blocks using a microtome set at 5 μm and were mounted on positively charged slides. These slides were allowed to air dry overnight prior to staining. Human normal tissue arrays were purchased from Pantomics, and non-Hodgkin's lymphoma tissue micro arrays were purchased from TriStar Technology Group LLC.

TABLE 2

FFPE Test Samples

| Human Tissue Type | Commercial Source |
|---|---|
| Normal Spleen (2) | Mercy Health Systems |
| Normal Tonsil (3) | Mercy Health Systems (2) and Ardais Corporation (1) |
| Normal Tissue Micro Array | Pantomics |
| Non-Hodgkins's Lymphoma Tissue Micro Array | TriStar Technology Group LLC |

CD37 staining intensity and distribution patterns were scored relative to control IgG staining (non-specific), and 1B11-2 staining was compared with the staining observed with Leica's NCL-CD37 mouse monoclonal antibody. Intensity was scored on a scale of 0 to 3 where 0=no staining, 1=weak staining, 2=moderate staining, and 3=strong staining. Uniformity of the staining was scored as negative (no cells exhibit positive staining), focal (<25% of cells stained), heterogeneous (25-75% of cells stained), and homogeneous (>75% of cells stained). The staining intensity and scoring scales are described below. All staining was evaluated by a Board certified pathologist.

TABLE 3

Intensity and Uniformity of Staining

Intensity (Amount of Membrane Staining)

| | |
|---|---|
| 0 | Negative |
| 1 | Weak |
| 2 | Moderate |
| 3 | Strong |

Uniformity (Percent of Positive Cells)

| | |
|---|---|
| 0 | Negative |
| Focal | <25% |
| Heterogeneous (hetero) | 25-75% |
| Homogeneous (homo) | >75% |

Validation of Purified 1B11-2 Antibody for FFPE CD37 IHC

Purified antibody from clone 1B11-2 diluted at 8.4 μg/mL, 4.2 μg/mL, and 2.1 μg/mL in Leica Antibody Diluent (Tris-buffered saline, surfactant, and protein stabilizer with 0.35% ProClin™ 950) was used to stain CD37-positive control samples (human normal tonsil, Daudi cells, Ramos cells, and Namalwa cells). The antibody was evaluated for CD37 specificity as measured by acceptable membrane staining and specificity in CD37-positive samples. This clone was also compared with the NCL-CD37 mouse mAb (clone CT1) diluted to 4.2 μg/mL in Leica Antibody Diluent using the same CD37 positive human tissue and cells. Leica's NCL-CD37 antibody produced acceptable membrane staining in each of the CD37 positive cell pellets, and acceptable membrane staining in the germinal centers and mantle zones of the tonsil tissue (both positive for CD37) along with some low level nuclear background, and no staining in the interfollicular region of the tonsil (which is CD37 negative). 1B11-2 exhibited acceptable membrane staining in CD37 positive samples and good specificity with the added advantage of a complete lack of nuclear background staining (see FIG. 5 for images of 1B11-2 compared with Leica's NCL-CD37 Mouse mAb). 1B11-2 produced membrane staining in a pattern that was similar to that observed with Leica's NCL-CD37 Mouse monoclonal antibody; however, this membrane staining was more specific and more clearly defined than that produced by Leica's NCL-CD37 antibody. It is also important to note that 1B11-2 did not produce staining in the interfollicular region of the tonsil (negative for CD37 expression) which demonstrates increased specificity. A suitable staining concentration of 4.2 μg/mL was experimentally determined for 1B11-2.

1B11-2 diluted at 4.2 μg/mL in Leica Antibody Diluent was also used to stain a human normal tissue array (purchased from Pantomics) and human tonsil and spleen tissues to evaluate specificity. Again 1B11-2 was compared with Leica's NCL-CD37 mouse monoclonal antibody diluted at 4.2 μg/mL in Leica Antibody Diluent on the same normal tonsil and spleen tissues as well as the human normal tissue array. In most normal tissues (excluding tonsil and spleen) Leica's NCL-CD37 mouse monoclonal antibody exhibited staining only in scattered lymphocyte cells leaving the remainder of the tissues negative. There was some cytoplasmic background blush observed in the paneth cells of the small intestine and in the islet cells of the pancreas (see FIG. 6). Leica's NCL-CD37 antibody did produce acceptable membrane staining in the germinal centers and mantle zones of the human normal tonsil and in the marginal zone of the human normal spleen tissues albeit with some low level nuclear background. There was no staining present in the interfollicular region of the tonsil or in the red pulp of the spleen with Leica's NCL-CD37 antibody. 1B11-2 exhibited acceptable membrane staining in the germinal centers and mantle zones of the human normal tonsil and in the marginal zone of the human normal spleen tissues and only scattered lymphocyte staining in the remaining normal tissues with no background staining at all (see FIG. 6). There was also no staining in the interfollicular region of the tonsil or in the red pulp of the spleen. These results demonstrate that 1B11-2 is advantageous in terms of staining sensitivity, specificity, and reduced background, all of which are critical for high quality performance and analysis of IHC assays.

Example 5

IHC Evaluation of 1B11-2 CD37 Antibody Using Human Tumor Samples

Human tumor samples representative of diffuse large B-cell lymphoma (n=52), follicular lymphoma (n=20), and chronic lymphocytic leukemia/small lymphocytic lymphoma (n=8) (all included in a non-Hodgkin's lymphoma tissue microarray purchased from TriStar Technology Group LLC) were evaluated for CD37 expression by IHC using the 1B11-2 antibody. The intensity of CD37 staining and the distribution of scores are summarized in Table 4, below. FIG. 7 shows an example of staining of diffuse large B cell lymphoma and follicular lymphoma tissues with the 1B11-2 antibody. These results demonstrate the advantages of 1B11-2 as a more specific and sensitive antibody for use in IHC assays to assess CD37 expression in non-Hodgkin's lymphoma patient tissues.

TABLE 4

Distribution of Scores (% Positivity)

| | TUMOR TYPE: | | |
|---|---|---|---|
| | DIFFUSE LARGE B CELL LYMPHOMA n = 52 | FOLLICULAR LYMPHOMA n = 20 | CHRONIC LYMPHOCYTIC LEUKEMIA/SMALL LYMPHOCYTIC LYMPHOMA n = 8 |
| Positive (any intensity): | 96% | 95% | 100% |
| ≥level 2 intensity with at least 25% tumor cells stained: | 58% | 35% | 50% |
| ≥level 3 intensity with at least 25% tumor cells stained: | 60% | 100% | 100% |

The 1B11-2 antibody and the NCL-CD37 mouse monoclonal (Leica) antibody and were compared using a non-Hodgkin's lymphoma tissue micro array (TMA) (purchased from TriStar Technology Group LLC). Using the NCL-CD37 antibody in an IHC assay (CD37 assay), 27% of diffuse large B cell lymphoma samples (14 out of 52), 85% of follicular lymphoma samples (17 out of 20), and 37% of chronic lymphocytic leukemia/small lymphocytic lymphoma samples (3 out of 8) were scored in the highest category (level 3 staining intensity on at least 25% tumor cells, Table 5). In contrast, the 1B11-2 antibody in the IHC assay described above utilizing the Leica Bond Refine Detection Kit on a Leica Bond Rx automated slide stainer, produced staining with increased sensitivity and specificity with 59% of diffuse large B cell lymphoma samples (31 out of 52), 95% of follicular lymphoma samples (19 out of 20), and 100% of chronic lymphocytic leukemia/small lymphocytic lymphoma samples (8 out of 8) producing staining that scored in the highest category (level 3 staining intensity on at least 25% tumor cells, Table 5). The 1B11-2 antibody was also able to detect low level CD37 expression in three diffuse large B cell lymphoma samples, whereas the Leica's NCL-CD37 antibody was unable to detect this low level of expression. These results demonstrate that 1B11-2 is advantageous in terms of staining sensitivity and specificity and produces a more dynamic range of CD37 staining.

TABLE 5

CD37 prevalence comparison in non-Hodgkin's lymphoma TMA

| | Diffuse Large B Cell Lymphoma (n = 52) | | Follicular Lymphoma (n = 20) | | Chronic Lymphocytic Leukemia/Small Lymphocytic Lymphoma (n = 8) | |
|---|---|---|---|---|---|---|
| Scores | NCL-CD37 | 1B11-2 | NCL-CD37 | 1B11-2 | NCL-CD37 | 1B11-2 |
| Positive (any intensity) | 47 (90%) | 50 (96%) | 19 (95%) | 19 (95%) | 8 (100%) | 8 (100%) |
| ≥level 1 intensity with at least 25% tumor cells stained: | 26 (50%) | 11 (21%) | 0 | 0 | 0 | 0 |
| ≥level 2 intensity with at least 25% tumor cells stained: | 33 (63%) | 30 (58%) | 12 (60%) | 7 (35%) | 7 (88%) | 4 (50%) |
| ≥level 3 intensity with at least 25% tumor cells stained: | 14 (27%) | 31 (60%) | 17 (85%) | 19 (95%) | 3 (38%) | 8 (100%) |

Example 6

Domain Mapping

Domain Mapping by Denaturing SDS PAGE Western Blotting

The ability to recognize different preparations of Fc-fused CD37-ECDs was tested in denaturing SDS PAGE followed by Western blotting for 1B11-2 (left panel), in direct comparison with a commercially available anti-CD37 antibody (Leica; right panel). Fc-fused CD37-ECD preparations were denatured by incubation in Laemmli buffer containing 70 mM β-mercapto-ethanol at 100° C. for 10 min, and were separated by SDS polyacrylamide gel electrophoresis, followed by electrophoretic transfer to PVDF membranes. Membranes were blocked with 5% non-fat milk in Tris-buffered saline with 0.1% Tween-20 (TBST) for 1 hour at room temperature. Primary antibodies were applied overnight, followed by detection with secondary anti-mouse F(ab)$_2$ conjugated to horse radish peroxidase for 1 h at room temperature. Blots were developed using enhanced chemiluminescence detection following standard procedures. The results are shown in FIG. 8. While the Leica antibody recognizes all three Fc-CD37 ECD preparations, the 1B11-2 antibody of the invention recognizes only hCD37-ECD-Fc and hCD37-Fc-LAGA, but not hCD37-ECD-S2-Fc. The hCD37-ECD-S2-Fc construct is missing the S1 segment (amino acids 110-137) of the CD37 ECD. Thus, a region of amino acids 110-137 is critical for epitope recognition by 1B11-2, but not by the Leica antibody.

Domain Mapping by Native PAGE Western Blotting

The ability to recognize different preparations of Fc-fused CD37-ECDs was tested in native PAGE followed by Western blotting for 1B11-2. Fc-fused CD37-ECD preparations were loaded in NativePage sample buffer and were separated by SDS polyacrylamide gel electrophoresis, followed by electrophoretic transfer to PVDF membranes or staining of the gel with Coomassie Brilliant Blue. The PVDF membrane was blocked with 5% non-fat milk in Tris-buffered saline with 0.1% Tween-20 (TBST) for 1 hour at room temperature. Primary antibody was applied overnight, followed by detection with secondary anti-mouse F(ab)$_2$ conjugated to horse radish peroxidase for 1 h at room temperature. The blot was developed using enhanced chemiluminescence detection following standard procedures. The results are shown in FIG. 9. Consistent with data from denaturing SDS PAGE (FIG. 8) and ELISA experiments (see FIG. 4), the 1B11-2 antibody of the invention recognizes only hCD37-ECD-Fc and hCD37-Fc-LAGA, but not hCD37-ECD-S2-Fc. These data demonstrate that the S1 segment (amino acids 110-137) of CD37 ECD or a portion thereof is critical for epitope recognition by 1B11-2 (left panel of FIG. 9). Coomassie Brilliant Blue gel stain (right panel of FIG. 9) demonstrates that hCD37-ECD-S2-Fc protein was present in sufficient amounts for detection by 1B11-2.

Example 7

Cloning and Sequencing of the VL and VH Regions of the Anti-Human CD37 Antibody Total cellular RNA was prepared from 5×10$^6$ cells of the anti-human CD37 hybridoma 1B11-2 described above using an RNeasy kit (QIAgen) according to the manufacturer's protocol. First strand cDNA was then synthesized from the total RNA using the SuperScript III cDNA synthesis kit (Invitrogen).

The PCR procedures for amplifying the antibody variable region cDNAs derived from hybridoma cells were based on methods described in Wang et al. ((2000) J Immunol Methods. 233:167-77) and Co et al. ((1992) J Immunol. 148: 1149-54). The variable light chain (VL) and variable heavy chain (VH) sequences were amplified by degenerate primers on the 5' end and either murine kappa or IgG1 constant region specific primers on the 3' end. The PCR reactions were then run on a 1% low melt agarose gel, followed by the excision of the 300 to 400 bp amplicon bands that were subsequently purified using Zymo DNA mini columns. The purified amplicons were sent to Beckman Coulter Genomics for sequencing utilizing the same 5' and 3' primers of the PCR reactions in order to generate the variable region cDNA sequences from both directions.

The degenerate primers used to clone the VL and VH cDNA sequences alter the 5' end, so additional sequencing efforts were needed to verify the complete variable region cDNA sequences. The preliminary sequences were entered into a search query of the NCBI IgBlast site (www.ncbi.nlm-.nih.gov/igblast/) to identify the murine germline sequences from which the antibody sequences had been derived. PCR primers were then designed to anneal to the germline linked leader sequence of the murine antibody so that this new PCR reaction would yield a complete variable region cDNA sequence, unaltered by the PCR primers. The PCR reactions, band purifications, and sequencing were performed as described above.

The variable regions cDNA sequences obtained for the anti-human CD37 antibody were combined with germline constant region sequences to obtain full length antibody cDNA sequences. The molecular weights of the heavy and light chains were then calculated from translations of the cDNA sequences and compared with the molecular weights obtained by LC/MS analyses of the purified murine anti-human CD37 antibody. The observed molecular weights for the murine 1B11-2 light and heavy chains matched the expected values, confirming that the cDNA sequences were correct.

The VH and VL CDR sequences are provided in Tables 1 and 2, respectively. The VH and VL sequences are provided in Tables 3 and 4, respectively. The full length heavy chain and light chain sequences are provided in Tables 5 and 6, respectively. The polynucleotide sequences of the VH and VL are provided in Table 8.

All publications, patents, patent applications, internet sites, and accession numbers/database sequences (including both polynucleotide and polypeptide sequences) cited herein are hereby incorporated by reference in their entirety for all purposes to the same extent as if each individual publication, patent, patent application, internet site, or accession number/database sequence were specifically and individually indicated to be so incorporated by reference.

What is claimed is:

1. An antibody or antigen-binding fragment thereof that specifically binds to CD37, wherein said antibody or fragment thereof comprises the VH CDR1, CDR2, and CDR3 sequences of SEQ ID NOs: 3-5 and the VL CDR1, CDR2, and CDR3 sequences of SEQ ID NOs: 6-8, respectively.

2. The antibody or antigen-binding fragment thereof of claim 1, wherein the antibody or fragment thereof comprises the polypeptide sequences of SEQ ID NOs:9 and/or 10.

3. The antibody or antigen-binding fragment thereof of claim 1, wherein said antibody or antigen-binding fragment thereof is murine, humanized, or chimeric.

4. The antibody or antigen-binding fragment thereof of claim 1, which is a full length antibody.

5. The antibody or antigen-binding fragment thereof of claim 1, which is an antigen-binding fragment.

6. The antibody or antigen-binding fragment thereof of claim 5, wherein said antibody or antigen-binding fragment thereof comprises a Fab, Fab', F(ab')2, single chain Fv or scFv, disulfide linked Fv, intrabody, IgGΔCH2, minibody, F(ab')3, tetrabody, triabody, diabody, DVD-Ig, mAb2, (scFv)2, or scFv-Fc.

7. The antibody or antigen-binding fragment thereof of claim 1, wherein the antibody or antigen-binding fragment thereof is detectably labeled.

8. A cell producing the antibody or antigen-binding fragment thereof of claim 1.

9. A method of making the antibody or antigen-binding fragment thereof of claim 1, comprising (a) culturing a cell producing the antibody or antigen-binding fragment thereof of claim 1; and (b) isolating said antibody or antigen-binding fragment thereof from said cultured cell.

10. A composition comprising the antibody or antigen-binding fragment thereof of claim 1 and buffer selected from the group consisting of: an IHC buffer, an ELISA buffer, and a FACS buffer.

11. A method of detecting CD37 expression in a sample comprising contacting said sample with the antibody or antigen-binding fragment thereof of claim 1.

12. The method of claim 11, wherein CD37 expression is determined by immunohistochemical (IHC) assay.

13. A method for treating cancer with a therapeutically active agent comprising an anti-CD37 antibody or antigen binding fragment thereof wherein said antibody or antigen binding fragment thereof in the therapeutically active agent is conjugated to a cytotoxin, said method comprising administering the therapeutically active agent to a subject having cancer, wherein increased expression of CD37 has been detected in a cancerous sample from said subject using the antibody or antigen-binding fragment there of claim 1.

14. The method of claim 13, wherein the detecting is by immunohistochemistry (IHC).

15. The method of claim 13, wherein the cancer is a leukemia or a lymphoma.

16. The method of claim 13, wherein said cancer is selected from the group consisting of B cell lymphomas, NHL, precursor B cell lymphoblastic leukemia/lymphoma and mature B cell neoplasms, B cell chronic lymphocytic leukemia (CLL)/small lymphocytic lymphoma (SLL), B cell prolymphocytic leukemia, lymphoplasmacytic lymphoma, mantle cell lymphoma (MCL), follicular lymphoma (FL), low grade, intermediate-grade and high-grade (FL), cutaneous follicle center lymphoma, marginal zone B cell lymphoma, MALT type marginal zone B cell lymphoma, nodal marginal zone B cell lymphoma, splenic type marginal zone B cell lymphoma, hairy cell leukemia, diffuse large B cell lymphoma, Burkitt's lymphoma, plasmacytoma, plasma cell myeloma, post-transplant lymphoproliferative disorder, Waldenstrom's macroglobulinemia, and anaplastic large-cell lymphoma (ALCL).

17. The method of claim 13, wherein the therapeutically active agent is an antibody maytansinoid conjugate that comprises a CD37 antibody comprising a heavy chain variable region comprising SEQ ID NO:28 and a light chain variable region comprising SEQ ID NO:29.

18. The method of claim 17, wherein the therapeutically active agent comprises the maytansinoid DM1, the non-cleavable SMCC linker, and wherein the CD37 antibody comprises a full length heavy chain comprising SEQ ID NO:30 and a full length light chain comprising SEQ ID NO:31.

19. The method of claim 16, wherein said cancer is diffuse large B cell lymphoma.

* * * * *

UNITED STATES PATENT AND TRADEMARK OFFICE
CERTIFICATE OF CORRECTION

PATENT NO. : 11,104,740 B2
APPLICATION NO. : 15/756345
DATED : August 31, 2021
INVENTOR(S) : Deckert et al.

Page 1 of 1

It is certified that error appears in the above-identified patent and that said Letters Patent is hereby corrected as shown below:

In the Claims

In Claim 13, at Column 93, Lines 7-8, change "antigen binding fragment" to -- antigen-binding fragment --.

In Claim 13, at Column 93, Lines 8-9, change "antigen binding fragment" to -- antigen-binding fragment --.

In Claim 13, at Column 93, Line 14, change "fragment there of claim 1" to -- fragment thereof of claim 1 --.

Signed and Sealed this
Seventh Day of December, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 34

<210> SEQ ID NO 1
<211> LENGTH: 281
<212> TYPE: PRT
<213> ORGANISM: Homo sapiens
```

<400> SEQUENCE: 1

Met Ser Ala Gln Glu Ser Cys Leu Ser Leu Ile Lys Tyr Phe Leu Phe
1               5                   10                  15

Val Phe Asn Leu Phe Phe Phe Val Leu Gly Ser Leu Ile Phe Cys Phe
            20                  25                  30

Gly Ile Trp Ile Leu Ile Asp Lys Thr Ser Phe Val Ser Phe Val Gly
        35                  40                  45

Leu Ala Phe Val Pro Leu Gln Ile Trp Ser Lys Val Leu Ala Ile Ser
    50                  55                  60

Gly Ile Phe Thr Met Gly Ile Ala Leu Gly Cys Val Gly Ala Leu
65                  70                  75                  80

Lys Glu Leu Arg Cys Leu Leu Gly Leu Tyr Phe Gly Met Leu Leu Leu
                85                  90                  95

Leu Phe Ala Thr Gln Ile Thr Leu Gly Ile Leu Ile Ser Thr Gln Arg
            100                 105                 110

Ala Gln Leu Glu Arg Ser Leu Arg Asp Val Val Glu Lys Thr Ile Gln
        115                 120                 125

Lys Tyr Gly Thr Asn Pro Glu Glu Thr Ala Ala Glu Glu Ser Trp Asp
130                 135                 140

Tyr Val Gln Phe Gln Leu Arg Cys Cys Gly Trp His Tyr Pro Gln Asp
145                 150                 155                 160

Trp Phe Gln Val Leu Ile Leu Arg Gly Asn Gly Ser Glu Ala His Arg
                165                 170                 175

Val Pro Cys Ser Cys Tyr Asn Leu Ser Ala Thr Asn Asp Ser Thr Ile
            180                 185                 190

Leu Asp Lys Val Ile Leu Pro Gln Leu Ser Arg Leu Gly His Leu Ala
        195                 200                 205

Arg Ser Arg His Ser Ala Asp Ile Cys Ala Val Pro Ala Glu Ser His
    210                 215                 220

Ile Tyr Arg Glu Gly Cys Ala Gln Gly Leu Gln Lys Trp Leu His Asn
225                 230                 235                 240

Asn Leu Ile Ser Ile Val Gly Ile Cys Leu Gly Val Gly Leu Leu Glu
                245                 250                 255

Leu Gly Phe Met Thr Leu Ser Ile Phe Leu Cys Arg Asn Leu Asp His
            260                 265                 270

Val Tyr Asn Arg Leu Ala Arg Tyr Arg
        275                 280

<210> SEQ ID NO 2
<211> LENGTH: 843
<212> TYPE: DNA
<213> ORGANISM: Homo sapiens

<400> SEQUENCE: 2
atgtcagccc aggagagctg cctcagcctc atcaagtact tcctcttcgt tttcaacctc      60
ttcttcttcg tcctcggcag cctgatcttc tgcttcggca tctggatcct cattgacaag    120
accagcttcg tgtcctttgt gggcttggcc ttcgtgcctc tgcagatctg gtccaaagtc    180
ctggccatct caggaatctt caccatgggc atcgccctcc tgggttgtgt ggggccctc     240 aaggagctcc gctgcctcct gggcctgtat tttgggatgc tgctgctcct gtttgccaca    300
cagatcaccc tgggaatcct catctccact cagcgggccc agctggagcg aagcttgcgg    360
gacgtcgtag agaaaaccat ccaaaagtac ggcaccaacc ccgaggagac cgcggccgag    420
gagagctggg actatgtgca gttccagctg cgctgctgcg gctggcacta cccgcaggac    480

-continued

```
tggttccaag tcctcatcct gagaggtaac gggtcggagg cgcaccgcgt gccctgctcc      540
tgctacaact tgtcggcgac caacgactcc acaatcctag ataaggtgat cttgccccag      600
ctcagcaggc ttggacacct ggcgcggtcc agacacagtg cagacatctg cgctgtccct      660
gcagagagcc acatctaccg cgagggctgc gcgcagggcc tccagaagtg gctgcacaac      720
aaccttattt ccatagtggg catttgcctg ggcgtcggcc tactcgagct cgggttcatg      780
acgctctcga tattcctgtg cagaaacctg gaccacgtct acaaccggct cgctcgatac      840
cgt                                                                    843
```

<210> SEQ ID NO 3
<211> LENGTH: 5
<212> TYPE: PRT
<213> ORGANISM: Artificial Sequence
<220> FEATURE:
<223> OTHER INFORMATION: muCD37-1B11-2 VH-CDR1

<400> SEQUENCE: 3

Gly Tyr Phe Met Asn
1               5

<210> SEQ ID NO 4
<211> LENGTH: 17
<212> TYPE: PRT
<213> ORGANISM: Artificial Sequence
<220> FEATURE:
<223> OTHER INFORMATION: muCD37-1B11-2 VH-CDR2 (Kabat)

<400> SEQUENCE: 4

Arg Ile Asn Pro Tyr Asn Gly Asp Thr Phe Tyr Asn Gln Lys Phe Lys
1               5                   10                  15

Gly

<210> SEQ ID NO 5
<211> LENGTH: 12
<212> TYPE: PRT
<213> ORGANISM: Artificial Sequence
<220> FEATURE:
<223> OTHER INFORMATION: muCD37-1B11-2 VH -CDR3

<400> SEQUENCE: 5

Arg Gly Ile Val Ala Ser Ser Arg Phe Phe Asp Val
1               5                   10

<210> SEQ ID NO 6
<211> LENGTH: 11
<212> TYPE: PRT
<213> ORGANISM: Artificial Sequence
<220> FEATURE:
<223> OTHER INFORMATION: muCD37-1B11-2 VL-CDR1

<400> SEQUENCE: 6

Lys Ala Ser Gln Gly Val Ser Asn Asp Val Asp
1               5                   10

<210> SEQ ID NO 7
<211> LENGTH: 7
<212> TYPE: PRT
<213> ORGANISM: Artificial Sequence
<220> FEATURE:
<223> OTHER INFORMATION: muCD37-1B11-2 VL-CDR2

<400> SEQUENCE: 7

Tyr Ala Ser Asn Arg Tyr Thr
1               5

<210> SEQ ID NO 8
<211> LENGTH: 9
<212> TYPE: PRT
<213> ORGANISM: Artificial Sequence
<220> FEATURE:
<223> OTHER INFORMATION: muCD37-1B11-2 VL-CDR3

<400> SEQUENCE: 8

Cys His Gln Asp Tyr Thr Ser Pro Thr
1               5

<210> SEQ ID NO 9
<211> LENGTH: 121
<212> TYPE: PRT
<213> ORGANISM: Artificial Sequence
<220> FEATURE:
<223> OTHER INFORMATION: muCD37-1B11-2 heavy chain variable region (VH)

<400> SEQUENCE: 9

Glu Val Gln Leu Leu Gln Ser Gly Pro Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Phe Met Asn Trp Val Ile Gln Ser His Gly Lys Gly Leu Glu Trp Ile
        35                  40                  45

Gly Arg Ile Asn Pro Tyr Asn Gly Asp Thr Phe Tyr Asn Gln Lys Phe
    50                  55                  60

Lys Gly Lys Ala Thr Leu Thr Val Asp Lys Ser Ser Thr Thr Ala His
65                  70                  75                  80

Met Glu Leu Leu Ser Leu Thr Ser Glu Asp Ser Ala Val Tyr Tyr Cys
                85                  90                  95

Gly Ser Arg Gly Ile Val Ala Ser Ser Arg Phe Phe Asp Val Trp Gly
            100                 105                 110

Ala Gly Thr Ser Val Ile Val Ser Ser
        115                 120

<210> SEQ ID NO 10
<211> LENGTH: 107
<212> TYPE: PRT
<213> ORGANISM: Artificial Sequence
<220> FEATURE:
<223> OTHER INFORMATION: muCD37-1B11-2 light chain variable region

<400> SEQUENCE: 10

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Gly Val Ser Asn Asp
            20                  25                  30

Val Asp Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
    50                  55                  60

Ser Gly Tyr Gly Thr Asp Phe Thr Phe Ser Ile Ser Thr Val Gln Ala
65                  70                  75                  80

Glu Asp Leu Ala Val Tyr Phe Cys His Gln Asp Tyr Thr Ser Pro Thr
                85                  90                  95

Phe Gly Gly Gly Thr Lys Leu Glu Ile Lys Arg

<210> SEQ ID NO 11
<211> LENGTH: 444
<212> TYPE: PRT
<213> ORGANISM: Artificial Sequence
<220> FEATURE:
<223> OTHER INFORMATION: muCD37-1B11-2 full length heavy chain

<400> SEQUENCE: 11

```
Glu Val Gln Leu Leu Gln Ser Gly Pro Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Phe Met Asn Trp Val Ile Gln Ser His Gly Lys Gly Leu Glu Trp Ile
        35                  40                  45

Gly Arg Ile Asn Pro Tyr Asn Gly Asp Thr Phe Tyr Asn Gln Lys Phe
    50                  55                  60

Lys Gly Lys Ala Thr Leu Thr Val Asp Lys Ser Ser Thr Thr Ala His
65                  70                  75                  80

Met Glu Leu Leu Ser Leu Thr Ser Glu Asp Ser Ala Val Tyr Tyr Cys
                85                  90                  95

Gly Ser Arg Gly Ile Val Ala Ser Ser Arg Phe Phe Asp Val Trp Gly
            100                 105                 110

Ala Gly Thr Ser Val Ile Val Ser Ala Lys Thr Thr Pro Pro Ser
        115                 120                 125

Val Tyr Pro Leu Ala Pro Gly Ser Ala Ala Gln Thr Asn Ser Met Val
    130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Glu Ser Asp Leu Tyr Thr Leu Ser Ser Val Thr Val Pro
            180                 185                 190

Ser Ser Pro Arg Pro Ser Glu Thr Val Thr Cys Asn Val Ala His Pro
        195                 200                 205

Ala Ser Ser Thr Lys Val Asp Lys Lys Ile Val Pro Arg Asp Cys Gly
    210                 215                 220

Cys Lys Pro Cys Ile Cys Thr Val Pro Glu Val Ser Ser Val Phe Ile
225                 230                 235                 240

Phe Pro Pro Lys Pro Lys Asp Val Leu Thr Ile Thr Leu Thr Pro Lys
                245                 250                 255

Val Thr Cys Val Val Val Asp Ile Ser Lys Asp Asp Pro Glu Val Gln
            260                 265                 270

Phe Ser Trp Phe Val Asp Asp Val His Thr Ala Gln Thr Gln Pro
        275                 280                 285

Arg Glu Glu Gln Phe Asn Ser Thr Phe Arg Ser Val Ser Glu Leu Pro
    290                 295                 300

Ile Met His Gln Asp Trp Leu Asn Gly Lys Glu Phe Lys Cys Arg Val
305                 310                 315                 320

Asn Ser Ala Ala Phe Pro Ala Pro Ile Glu Lys Thr Ile Ser Lys Thr
                325                 330                 335

Lys Gly Arg Pro Lys Ala Pro Gln Val Tyr Thr Ile Pro Pro Pro Lys
            340                 345                 350

Glu Gln Met Ala Lys Asp Lys Val Ser Leu Thr Cys Met Ile Thr Asp
```

```
                355                 360                 365
Phe Phe Pro Glu Asp Ile Thr Val Glu Trp Gln Trp Asn Gly Gln Pro
370                 375                 380

Ala Glu Asn Tyr Lys Asn Thr Gln Pro Ile Met Asn Thr Asn Gly Ser
385                 390                 395                 400

Tyr Phe Val Tyr Ser Lys Leu Asn Val Gln Lys Ser Asn Trp Glu Ala
                405                 410                 415

Gly Asn Thr Phe Thr Cys Ser Val Leu His Glu Gly Leu His Asn His
                420                 425                 430

His Thr Glu Lys Ser Leu Ser His Ser Pro Gly Lys
                435                 440

<210> SEQ ID NO 12
<211> LENGTH: 213
<212> TYPE: PRT
<213> ORGANISM: Artificial Sequence
<220> FEATURE:
<223> OTHER INFORMATION: muCD37-1B11-2 full length light chain

<400> SEQUENCE: 12

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Gly Val Ser Asn Asp
                20                  25                  30

Val Asp Trp Tyr Gln Gln Lys Pro Gly Gln Ser Pro Lys Leu Leu Ile
            35                  40                  45

Tyr Tyr Ala Ser Asn Arg Tyr Thr Gly Val Pro Asp Arg Phe Thr Gly
50                  55                  60

Ser Gly Tyr Gly Thr Asp Phe Thr Phe Ser Ile Ser Thr Val Gln Ala
65                  70                  75                  80

Glu Asp Leu Ala Val Tyr Phe Cys His Gln Asp Tyr Thr Ser Pro Thr
                85                  90                  95

Phe Gly Gly Gly Thr Lys Leu Glu Ile Lys Arg Ala Asp Ala Ala Pro
            100                 105                 110

Thr Val Ser Ile Phe Pro Pro Ser Ser Glu Gln Leu Thr Ser Gly Gly
            115                 120                 125

Ala Ser Val Val Cys Phe Leu Asn Asn Phe Tyr Pro Lys Asp Ile Asn
130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
            195                 200                 205

Asn Arg Asn Glu Cys
    210

<210> SEQ ID NO 13
<211> LENGTH: 376
<212> TYPE: DNA
<213> ORGANISM: Artificial Sequence
<220> FEATURE:
<223> OTHER INFORMATION: muCD37-1B11-2 VH

<400> SEQUENCE: 13
```

```
gaggttcaac tgctgcagtc tggacctgag ctggtgaagc tggggcttc  agtgaagata    60 tcctgcaagg cttctggtta ctcatttact ggctacttta tgaactgggt gatacagagc   120
catggaaagg ccttgagtg gattggacgt attaatcctt acaatggtga taccttctac   180
aaccagaagt tcaagggcaa ggccacattg actgtagaca atcctctac  acagcccac    240 atggagctcc tgagcctgac atctgaggac tctgccgtct attattgtgg atcccggggg   300
atagtggctt cctctaggtt cttcgatgtc tggggcgcag ggacctcggt catcgtctcc   360
tcagccaaaa cgacac                                                   376
```

<210> SEQ ID NO 14  
<211> LENGTH: 327  
<212> TYPE: DNA  
<213> ORGANISM: Artificial Sequence  
<220> FEATURE:  
<223> OTHER INFORMATION: muCD37-1B11-2 VL

<400> SEQUENCE: 14

```
agtattgtga tgacccagac tcccaaattc ctgcttgtat cagcaggaga cagggttacc    60
ataacctgca aggccagtca gggtgtgagt aatgatgtag attggtacca acagaagcca   120
gggcagtctc ctaaactgct gatatactat gcatccaatc gctacactgg agtccctgat   180
cgcttcactg gcagtggata tgggacggat ttcactttca gcatcagcac tgtgcaggct   240
gaagacctgg cagtttattt ctgtcaccag gattatacct ctccgacgtt cggtggaggc   300
accaagctgg aaatcaaacg ggctgat                                       327
```

<210> SEQ ID NO 15  
<211> LENGTH: 164  
<212> TYPE: PRT  
<213> ORGANISM: Artificial Sequence  
<220> FEATURE:  
<223> OTHER INFORMATION: hCD37-LEL

<400> SEQUENCE: 15

```
Thr Met Glu Leu Leu Ile Ser Thr Gln Arg Ala Gln Leu Glu Arg Ser
1               5                   10                  15

Leu Arg Asp Val Val Glu Lys Thr Ile Gln Lys Tyr Gly Thr Asn Pro
            20                  25                  30

Glu Glu Thr Ala Ala Glu Glu Ser Trp Asp Tyr Val Gln Phe Gln Leu
        35                  40                  45

Arg Cys Cys Gly Trp His Tyr Pro Gln Asp Trp Phe Gln Val Leu Ile
    50                  55                  60

Leu Arg Gly Asn Gly Ser Glu Ala His Arg Val Pro Cys Ser Cys Tyr
65                  70                  75                  80

Asn Leu Ser Ala Thr Asn Asp Ser Thr Ile Leu Asp Lys Val Ile Leu
                85                  90                  95

Pro Gln Leu Ser Arg Leu Gly His Leu Ala Arg Ser Arg His Ser Ala
            100                 105                 110

Asp Ile Cys Ala Val Pro Ala Glu Ser His Ile Tyr Arg Glu Gly Cys
        115                 120                 125

Ala Gln Gly Leu Gln Lys Trp Leu His Asn Asn Leu Ser Phe Leu Glu
    130                 135                 140

Gln Lys Leu Ile Ser Glu Glu Asp Leu Asn Ser Ala Val Asp His His
145                 150                 155                 160

His His His His
```

```
<210> SEQ ID NO 16
<211> LENGTH: 368
<212> TYPE: PRT
<213> ORGANISM: Artificial Sequence
<220> FEATURE:
<223> OTHER INFORMATION: hCD37-ECD-Fc

<400> SEQUENCE: 16
```

| | | | | | | | | | | | | | | | |
|---|---|---|---|---|---|---|---|---|---|---|---|---|---|---|---|
| Gly | Pro | Glu | Phe | Leu | Ile | Ser | Thr | Gln | Arg | Ala | Gln | Leu | Glu | Arg | Ser |
| 1 | | | | 5 | | | | | 10 | | | | | 15 | |
| Leu | Arg | Asp | Val | Val | Glu | Lys | Thr | Ile | Gln | Lys | Tyr | Gly | Thr | Asn | Pro |
| | | | 20 | | | | | 25 | | | | | 30 | | |
| Glu | Glu | Thr | Ala | Ala | Glu | Glu | Ser | Trp | Asp | Tyr | Val | Gln | Phe | Gln | Leu |
| | | | 35 | | | | | 40 | | | | | 45 | | |
| Arg | Cys | Cys | Gly | Trp | His | Tyr | Pro | Gln | Asp | Trp | Phe | Gln | Val | Leu | Ile |
| | 50 | | | | | 55 | | | | | 60 | | | | |
| Leu | Arg | Gly | Asn | Gly | Ser | Glu | Ala | His | Arg | Val | Pro | Cys | Ser | Cys | Tyr |
| 65 | | | | | 70 | | | | | 75 | | | | | 80 |
| Asn | Leu | Ser | Ala | Thr | Asn | Asp | Ser | Thr | Ile | Leu | Asp | Lys | Val | Ile | Leu |
| | | | | 85 | | | | | 90 | | | | | 95 | |
| Pro | Gln | Leu | Ser | Arg | Leu | Gly | His | Leu | Ala | Arg | Ser | Arg | His | Ser | Ala |
| | | | 100 | | | | | 105 | | | | | 110 | | |
| Asp | Ile | Cys | Ala | Val | Pro | Ala | Glu | Ser | His | Ile | Tyr | Arg | Glu | Gly | Cys |
| | | 115 | | | | | 120 | | | | | 125 | | | |
| Ala | Gln | Gly | Leu | Gln | Gly | Ser | Glu | Pro | Arg | Gly | Pro | Thr | Ile | Lys | Pro |
| | 130 | | | | | 135 | | | | | 140 | | | | |
| Cys | Pro | Pro | Cys | Lys | Cys | Pro | Ala | Pro | Asn | Leu | Leu | Gly | Gly | Pro | Ser |
| 145 | | | | | 150 | | | | | 155 | | | | | 160 |
| Val | Phe | Ile | Phe | Pro | Pro | Lys | Ile | Lys | Asp | Val | Leu | Met | Ile | Ser | Leu |
| | | | | 165 | | | | | 170 | | | | | 175 | |
| Ser | Pro | Ile | Val | Thr | Cys | Val | Val | Asp | Val | Ser | Glu | Asp | Asp | Pro | |
| | | | 180 | | | | | 185 | | | | | 190 | | |
| Asp | Val | Gln | Ile | Ser | Trp | Phe | Val | Asn | Asn | Val | Glu | Val | His | Thr | Ala |
| | | 195 | | | | | 200 | | | | | 205 | | | |
| Gln | Thr | Gln | Thr | His | Arg | Glu | Asp | Tyr | Asn | Ser | Thr | Leu | Arg | Val | Val |
| | 210 | | | | | 215 | | | | | 220 | | | | |
| Ser | Ala | Leu | Pro | Ile | Gln | His | Gln | Asp | Trp | Met | Ser | Gly | Lys | Glu | Phe |
| 225 | | | | | 230 | | | | | 235 | | | | | 240 |
| Lys | Cys | Lys | Val | Asn | Asn | Lys | Asp | Leu | Pro | Ala | Pro | Ile | Glu | Arg | Thr |
| | | | | 245 | | | | | 250 | | | | | 255 | |
| Ile | Ser | Lys | Pro | Lys | Gly | Ser | Val | Arg | Ala | Pro | Gln | Val | Tyr | Val | Leu |
| | | | 260 | | | | | 265 | | | | | 270 | | |
| Pro | Pro | Pro | Glu | Glu | Glu | Met | Thr | Lys | Lys | Gln | Val | Thr | Leu | Thr | Cys |
| | | 275 | | | | | 280 | | | | | 285 | | | |
| Met | Val | Thr | Asp | Phe | Met | Pro | Glu | Asp | Ile | Tyr | Val | Glu | Trp | Thr | Asn |
| | 290 | | | | | 295 | | | | | 300 | | | | |
| Asn | Gly | Lys | Thr | Glu | Leu | Asn | Tyr | Lys | Asn | Thr | Glu | Pro | Val | Leu | Asp |
| 305 | | | | | 310 | | | | | 315 | | | | | 320 |
| Ser | Asp | Gly | Ser | Tyr | Phe | Met | Tyr | Ser | Lys | Leu | Arg | Val | Glu | Lys | Lys |
| | | | | 325 | | | | | 330 | | | | | 335 | |
| Asn | Trp | Val | Glu | Arg | Asn | Ser | Tyr | Ser | Cys | Ser | Val | Val | His | Glu | Gly |
| | | | 340 | | | | | 345 | | | | | 350 | | |
| Leu | His | Asn | His | His | Thr | Thr | Lys | Ser | Phe | Ser | Arg | Thr | Pro | Gly | Lys |
| | | 355 | | | | | 360 | | | | | 365 | | | |

<210> SEQ ID NO 17
<211> LENGTH: 361
<212> TYPE: PRT
<213> ORGANISM: Artificial Sequence
<220> FEATURE:
<223> OTHER INFORMATION: hCD37-Fc-LAGA

<400> SEQUENCE: 17

```
Gly Pro Glu Phe Leu Ile Ser Thr Gln Arg Ala Gln Leu Glu Arg Ser
1               5                   10                  15

Leu Arg Asp Val Val Glu Lys Thr Ile Gln Lys Tyr Gly Thr Asn Pro
            20                  25                  30

Glu Glu Thr Ala Ala Glu Glu Ser Trp Asp Tyr Val Gln Phe Gln Leu
        35                  40                  45

Arg Cys Cys Gly Trp His Tyr Pro Gln Asp Trp Phe Gln Val Leu Ile
    50                  55                  60

Leu Arg Gly Asn Gly Ser Glu Ala His Arg Val Pro Cys Ser Cys Tyr
65                  70                  75                  80

Asn Leu Ser Ala Thr Asn Asp Ser Thr Ile Leu Asp Lys Val Ile Leu
                85                  90                  95

Pro Gln Leu Ser Arg Leu Gly His Leu Ala Arg Ser Arg His Ser Ala
            100                 105                 110

Asp Ile Cys Ala Val Pro Ala Glu Ser His Ile Tyr Arg Glu Gly Cys
        115                 120                 125

Ala Gln Gly Leu Gln Gly Ser Asp Lys Thr His Thr Cys Pro Pro Cys
    130                 135                 140

Pro Ala Pro Glu Leu Ala Gly Ala Pro Ser Val Phe Leu Phe Pro Pro
145                 150                 155                 160

Lys Pro Lys Asp Thr Leu Met Ile Ser Arg Thr Pro Glu Val Thr Cys
                165                 170                 175

Val Val Val Asp Val Ser His Glu Asp Pro Glu Val Lys Phe Asn Trp
            180                 185                 190

Tyr Val Asp Gly Val Glu Val His Asn Ala Lys Thr Lys Pro Arg Glu
        195                 200                 205

Glu Gln Tyr Asn Ser Thr Tyr Arg Val Val Ser Val Leu Thr Val Leu
    210                 215                 220

His Gln Asp Trp Leu Asn Gly Lys Glu Tyr Lys Cys Lys Val Ser Asn
225                 230                 235                 240

Lys Ala Leu Pro Ala Pro Ile Glu Lys Thr Ile Ser Lys Ala Lys Gly
                245                 250                 255

Gln Pro Arg Glu Pro Gln Val Tyr Thr Leu Pro Pro Ser Arg Asp Glu
            260                 265                 270

Leu Thr Lys Asn Gln Val Ser Leu Thr Cys Leu Val Lys Gly Phe Tyr
        275                 280                 285

Pro Ser Asp Ile Ala Val Glu Trp Glu Ser Asn Gly Gln Pro Glu Asn
    290                 295                 300

Asn Tyr Lys Thr Thr Pro Pro Val Leu Asp Ser Asp Gly Ser Phe Phe
305                 310                 315                 320

Leu Tyr Ser Lys Leu Thr Val Asp Lys Ser Arg Trp Gln Gln Gly Asn
                325                 330                 335

Val Phe Ser Cys Ser Val Met His Glu Ala Leu His Asn His Tyr Thr
            340                 345                 350

Gln Lys Ser Leu Ser Leu Ser Pro Gly
        355                 360
```

<210> SEQ ID NO 18
<211> LENGTH: 340
<212> TYPE: PRT
<213> ORGANISM: Artificial Sequence
<220> FEATURE:
<223> OTHER INFORMATION: hCD37-ECD-S2-Fc

<400> SEQUENCE: 18

```
Gly Pro Glu Phe Leu Ile Ser Ala Ala Glu Ser Trp Asp Tyr Val
1               5                   10                  15

Gln Phe Gln Leu Arg Cys Cys Gly Trp His Tyr Pro Gln Asp Trp Phe
                20                  25                  30

Gln Val Leu Ile Leu Arg Gly Asn Gly Ser Glu Ala His Arg Val Pro
            35                  40                  45

Cys Ser Cys Tyr Asn Leu Ser Ala Thr Asn Asp Ser Thr Ile Leu Asp
        50                  55                  60

Lys Val Ile Leu Pro Gln Leu Ser Arg Leu Gly His Leu Ala Arg Ser
65                  70                  75                  80

Arg His Ser Ala Asp Ile Cys Ala Val Pro Ala Glu Ser His Ile Tyr
                85                  90                  95

Arg Glu Gly Cys Ala Gln Gly Leu Gln Gly Ser Glu Pro Arg Gly Pro
            100                 105                 110

Thr Ile Lys Pro Cys Pro Pro Cys Lys Cys Pro Ala Pro Asn Leu Leu
        115                 120                 125

Gly Gly Pro Ser Val Phe Ile Phe Pro Pro Lys Ile Lys Asp Val Leu
        130                 135                 140

Met Ile Ser Leu Ser Pro Ile Val Thr Cys Val Val Val Asp Val Ser
145                 150                 155                 160

Glu Asp Asp Pro Asp Val Gln Ile Ser Trp Phe Val Asn Asn Val Glu
                165                 170                 175

Val His Thr Ala Gln Thr Gln Thr His Arg Glu Asp Tyr Asn Ser Thr
            180                 185                 190

Leu Arg Val Val Ser Ala Leu Pro Ile Gln His Gln Asp Trp Met Ser
        195                 200                 205

Gly Lys Glu Phe Lys Cys Lys Val Asn Asn Lys Asp Leu Pro Ala Pro
    210                 215                 220

Ile Glu Arg Thr Ile Ser Lys Pro Lys Gly Ser Val Arg Ala Pro Gln
225                 230                 235                 240

Val Tyr Val Leu Pro Pro Pro Glu Glu Glu Met Thr Lys Lys Gln Val
                245                 250                 255

Thr Leu Thr Cys Met Val Thr Asp Phe Met Pro Glu Asp Ile Tyr Val
            260                 265                 270

Glu Trp Thr Asn Asn Gly Lys Thr Glu Leu Asn Tyr Lys Asn Thr Glu
        275                 280                 285

Pro Val Leu Asp Ser Asp Gly Ser Tyr Phe Met Tyr Ser Lys Leu Arg
    290                 295                 300

Val Glu Lys Lys Asn Trp Val Glu Arg Asn Ser Tyr Ser Cys Ser Val
305                 310                 315                 320

Val His Glu Gly Leu His Asn His His Thr Thr Lys Ser Phe Ser Arg
                325                 330                 335

Thr Pro Gly Lys
            340
```

<210> SEQ ID NO 19
<211> LENGTH: 129
<212> TYPE: PRT

<213> ORGANISM: Artificial Sequence
<220> FEATURE:
<223> OTHER INFORMATION: hCD37

<400> SEQUENCE: 19

```
Leu Ile Ser Thr Gln Arg Ala Gln Leu Glu Arg Ser Leu Arg Asp Val
1               5                   10                  15

Val Glu Lys Thr Ile Gln Lys Tyr Gly Thr Asn Pro Glu Glu Thr Ala
            20                  25                  30

Ala Glu Glu Ser Trp Asp Tyr Val Gln Phe Gln Leu Arg Cys Cys Gly
        35                  40                  45

Trp His Tyr Pro Gln Asp Trp Phe Gln Val Leu Ile Leu Arg Gly Asn
    50                  55                  60

Gly Ser Glu Ala His Arg Val Pro Cys Ser Cys Tyr Asn Leu Ser Ala
65                  70                  75                  80

Thr Asn Asp Ser Thr Ile Leu Asp Lys Val Ile Leu Pro Gln Leu Ser
                85                  90                  95

Arg Leu Gly His Leu Ala Arg Ser Arg His Ser Ala Asp Ile Cys Ala
            100                 105                 110

Val Pro Ala Glu Ser His Ile Tyr Arg Glu Gly Cys Ala Gln Gly Leu
        115                 120                 125

Gln
```

<210> SEQ ID NO 20
<211> LENGTH: 136
<212> TYPE: PRT
<213> ORGANISM: Artificial Sequence
<220> FEATURE:
<223> OTHER INFORMATION: hCD37

<400> SEQUENCE: 20

```
Leu Ile Ser Thr Gln Arg Ala Gln Leu Glu Arg Ser Leu Arg Asp Val
1               5                   10                  15

Val Glu Lys Thr Ile Gln Lys Tyr Gly Thr Asn Pro Glu Glu Thr Ala
            20                  25                  30

Ala Glu Glu Ser Trp Asp Tyr Val Gln Phe Gln Leu Arg Cys Cys Gly
        35                  40                  45

Trp His Tyr Pro Gln Asp Trp Phe Gln Val Leu Ile Leu Arg Gly Asn
    50                  55                  60

Gly Ser Glu Ala His Arg Val Pro Cys Ser Cys Tyr Asn Leu Ser Ala
65                  70                  75                  80

Thr Asn Asp Ser Thr Ile Leu Asp Lys Val Ile Leu Pro Gln Leu Ser
                85                  90                  95

Arg Leu Gly His Leu Ala Arg Ser Arg His Ser Ala Asp Ile Cys Ala
            100                 105                 110

Val Pro Ala Glu Ser His Ile Tyr Arg Glu Gly Cys Ala Gln Gly Leu
        115                 120                 125

Gln Lys Trp Leu His Asn Asn Leu
    130                 135
```

<210> SEQ ID NO 21
<211> LENGTH: 101
<212> TYPE: PRT
<213> ORGANISM: Artificial Sequence
<220> FEATURE:
<223> OTHER INFORMATION: hCD37

<400> SEQUENCE: 21

-continued

```
Leu Ile Ser Ala Ala Glu Glu Ser Trp Asp Tyr Val Gln Phe Gln Leu
1               5                   10                  15

Arg Cys Cys Gly Trp His Tyr Pro Gln Asp Trp Phe Gln Val Leu Ile
            20                  25                  30

Leu Arg Gly Asn Gly Ser Glu Ala His Arg Val Pro Cys Ser Cys Tyr
        35                  40                  45

Asn Leu Ser Ala Thr Asn Asp Ser Thr Ile Leu Asp Lys Val Ile Leu
50                  55                  60

Pro Gln Leu Ser Arg Leu Gly His Leu Ala Arg Ser Arg His Ser Ala
65                  70                  75                  80

Asp Ile Cys Ala Val Pro Ala Glu Ser His Ile Tyr Arg Glu Gly Cys
                85                  90                  95

Ala Gln Gly Leu Gln
            100
```

<210> SEQ ID NO 22
<211> LENGTH: 5
<212> TYPE: PRT
<213> ORGANISM: Artificial Sequence
<220> FEATURE:
<223> OTHER INFORMATION: huCD37-3 VH-CDR1

<400> SEQUENCE: 22

```
Thr Ser Gly Val Ser
1               5
```

<210> SEQ ID NO 23
<211> LENGTH: 9
<212> TYPE: PRT
<213> ORGANISM: Artificial Sequence
<220> FEATURE:
<223> OTHER INFORMATION: huCD37-3 VH-CDR2

<400> SEQUENCE: 23

```
Val Ile Trp Gly Asp Gly Ser Thr Asn
1               5
```

<210> SEQ ID NO 24
<211> LENGTH: 7
<212> TYPE: PRT
<213> ORGANISM: Artificial Sequence
<220> FEATURE:
<223> OTHER INFORMATION: huCD37-3 VH-CDR3

<400> SEQUENCE: 24

```
Gly Gly Tyr Ser Leu Ala His
1               5
```

<210> SEQ ID NO 25
<211> LENGTH: 11
<212> TYPE: PRT
<213> ORGANISM: Artificial Sequence
<220> FEATURE:
<223> OTHER INFORMATION: huCD37-3 VL-CDR1

<400> SEQUENCE: 25

```
Arg Ala Ser Glu Asn Ile Arg Ser Asn Leu Ala
1               5                   10
```

<210> SEQ ID NO 26
<211> LENGTH: 7
<212> TYPE: PRT
<213> ORGANISM: Artificial Sequence
<220> FEATURE:

```
<223> OTHER INFORMATION: huCD37-3 VL-CDR2

<400> SEQUENCE: 26

Val Ala Thr Asn Leu Ala Asp
1               5

<210> SEQ ID NO 27
<211> LENGTH: 9
<212> TYPE: PRT
<213> ORGANISM: Artificial Sequence
<220> FEATURE:
<223> OTHER INFORMATION: huCD37-3 VL-CDR3

<400> SEQUENCE: 27

Gln His Tyr Trp Gly Thr Thr Trp Thr
1               5

<210> SEQ ID NO 28
<211> LENGTH: 115
<212> TYPE: PRT
<213> ORGANISM: Artificial Sequence
<220> FEATURE:
<223> OTHER INFORMATION: huCD37-3 VH v. 1.0

<400> SEQUENCE: 28

Gln Val Gln Val Gln Glu Ser Gly Pro Gly Leu Val Ala Pro Ser Gln
1               5                   10                  15

Thr Leu Ser Ile Thr Cys Thr Val Ser Gly Phe Ser Leu Thr Thr Ser
                20                  25                  30

Gly Val Ser Trp Val Arg Gln Pro Pro Gly Lys Gly Leu Glu Trp Leu
            35                  40                  45

Gly Val Ile Trp Gly Asp Gly Ser Thr Asn Tyr His Pro Ser Leu Lys
        50                  55                  60

Ser Arg Leu Ser Ile Lys Lys Asp His Ser Lys Ser Gln Val Phe Leu
65                  70                  75                  80

Lys Leu Asn Ser Leu Thr Ala Ala Asp Thr Ala Thr Tyr Tyr Cys Ala
                85                  90                  95

Lys Gly Gly Tyr Ser Leu Ala His Trp Gly Gln Gly Thr Leu Val Thr
            100                 105                 110

Val Ser Ser
        115

<210> SEQ ID NO 29
<211> LENGTH: 108
<212> TYPE: PRT
<213> ORGANISM: Artificial Sequence
<220> FEATURE:
<223> OTHER INFORMATION: huCD37-3 VL

<400> SEQUENCE: 29

Asp Ile Gln Met Thr Gln Ser Pro Ser Ser Leu Ser Val Ser Val Gly
1               5                   10                  15

Glu Arg Val Thr Ile Thr Cys Arg Ala Ser Glu Asn Ile Arg Ser Asn
                20                  25                  30

Leu Ala Trp Tyr Gln Gln Lys Pro Gly Lys Ser Pro Lys Leu Leu Val
            35                  40                  45

Asn Val Ala Thr Asn Leu Ala Asp Gly Val Pro Ser Arg Phe Ser Gly
        50                  55                  60

Ser Gly Ser Gly Thr Asp Tyr Ser Leu Lys Ile Asn Ser Leu Gln Pro
65                  70                  75                  80
```

Glu Asp Phe Gly Thr Tyr Tyr Cys Gln His Tyr Trp Gly Thr Thr Trp
                85                  90                  95

Thr Phe Gly Gln Gly Thr Lys Leu Glu Ile Lys Arg
            100                 105

<210> SEQ ID NO 30
<211> LENGTH: 444
<212> TYPE: PRT
<213> ORGANISM: Artificial Sequence
<220> FEATURE:
<223> OTHER INFORMATION: huCD37-3 Heavy Chain (HC) v. 1.0

<400> SEQUENCE: 30

Gln Val Gln Val Gln Glu Ser Gly Pro Gly Leu Val Ala Pro Ser Gln
1               5                   10                  15

Thr Leu Ser Ile Thr Cys Thr Val Ser Gly Phe Ser Leu Thr Thr Ser
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Pro Ser Leu Lys
    50                  55                  60

Ser Arg Leu Ser Ile Lys Lys Asp His Ser Lys Ser Gln Val Phe Leu
65                  70                  75                  80

Lys Leu Asn Ser Leu Thr Ala Ala Asp Thr Ala Thr Tyr Tyr Cys Ala
                85                  90                  95

Lys Gly Gly Tyr Ser Leu Ala His Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
            435                 440

<210> SEQ ID NO 31
<211> LENGTH: 214
<212> TYPE: PRT
<213> ORGANISM: Artificial Sequence
<220> FEATURE:
<223> OTHER INFORMATION: huCD37-3 Light Chain

<400> SEQUENCE: 31

Asp Ile Gln Met Thr Gln Ser Pro Ser Ser Leu Ser Val Ser Val Gly
1               5                   10                  15

Glu Arg Val Thr Ile Thr Cys Arg Ala Ser Glu Asn Ile Arg Ser Asn
            20                  25                  30

Leu Ala Trp Tyr Gln Gln Lys Pro Gly Lys Ser Pro Lys Leu Leu Val
        35                  40                  45

Asn Val Ala Thr Asn Leu Ala Asp Gly Val Pro Ser Arg Phe Ser Gly
    50                  55                  60

Ser Gly Ser Gly Thr Asp Tyr Ser Leu Lys Ile Asn Ser Leu Gln Pro
65                  70                  75                  80

Glu Asp Phe Gly Thr Tyr Tyr Cys Gln His Tyr Trp Gly Thr Thr Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 32
<211> LENGTH: 115
<212> TYPE: PRT
<213> ORGANISM: Artificial Sequence
<220> FEATURE:

<223> OTHER INFORMATION: huCD37-3 VH v. 1.1

<400> SEQUENCE: 32

Gln Val Gln Val Gln Glu Ser Gly Pro Gly Leu Val Ala Pro Ser Gln
1               5                   10                  15

Thr Leu Ser Ile Thr Cys Thr Val Ser Gly Phe Ser Leu Thr Thr Ser
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Ser Ser Leu Lys
    50                  55                  60

Ser Arg Leu Ser Ile Lys Lys Asp His Ser Lys Ser Gln Val Phe Leu
65                  70                  75                  80

Lys Leu Asn Ser Leu Thr Ala Ala Asp Thr Ala Thr Tyr Tyr Cys Ala
                85                  90                  95

Lys Gly Gly Tyr Ser Leu Ala His Trp Gly Gln Gly Thr Leu Val Thr
            100                 105                 110

Val Ser Ser
        115

<210> SEQ ID NO 33
<211> LENGTH: 444
<212> TYPE: PRT
<213> ORGANISM: Artificial Sequence
<220> FEATURE:
<223> OTHER INFORMATION: huCD37-3 Heavy Chain (HC) v. 1.1

<400> SEQUENCE: 33

Gln Val Gln Val Gln Glu Ser Gly Pro Gly Leu Val Ala Pro Ser Gln
1               5                   10                  15

Thr Leu Ser Ile Thr Cys Thr Val Ser Gly Phe Ser Leu Thr Thr Ser
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Ser Ser Leu Lys
    50                  55                  60

Ser Arg Leu Ser Ile Lys Lys Asp His Ser Lys Ser Gln Val Phe Leu
65                  70                  75                  80

Lys Leu Asn Ser Leu Thr Ala Ala Asp Thr Ala Thr Tyr Tyr Cys Ala
                85                  90                  95

Lys Gly Gly Tyr Ser Leu Ala His Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

```
Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
            290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
            435                 440

<210> SEQ ID NO 34
<211> LENGTH: 10
<212> TYPE: PRT
<213> ORGANISM: Artificial Sequence
<220> FEATURE:
<223> OTHER INFORMATION: muCD37-1B11-2 VH-CDR2 (AbM)

<400> SEQUENCE: 34

Arg Ile Asn Pro Tyr Asn Gly Asp Thr Phe
1               5                   10
```